US010233474B2

(12) United States Patent
Foster et al.

(10) Patent No.: US 10,233,474 B2
(45) Date of Patent: Mar. 19, 2019

(54) MATERIALS AND METHODS FOR PRODUCING 6-CARBON MONOMERS

(71) Applicant: INVISTA North America S.á.r.l., Wilmington, DE (US)

(72) Inventors: Alexander Brett Foster, Yarm (GB); Mariusz Kamionka, Cleveland (GB); Nadia Fatma Kadi, Cleveland (GB); Adriana Leonora Botes, Rosedale East (GB); Alex Van Eck Conradie, Eaglescliffe (GB)

(73) Assignee: INVISTA North America S.á.r.l., Wilmington, DE (US)

( * ) Notice: Subject to any disclaimer, the term of this patent is extended or adjusted under 35 U.S.C. 154(b) by 110 days.

(21) Appl. No.: 14/977,004

(22) Filed: Dec. 21, 2015

(65) Prior Publication Data

US 2016/0222425 A1 Aug. 4, 2016

Related U.S. Application Data

(60) Provisional application No. 62/095,537, filed on Dec. 22, 2014.

(51) Int. Cl.

| | |
|---|---|
| *C07H 1/00* | (2006.01) |
| *C12N 9/10* | (2006.01) |
| *C12P 7/24* | (2006.01) |
| *C12P 7/26* | (2006.01) |
| *C12P 7/42* | (2006.01) |
| *C12P 13/00* | (2006.01) |
| *C12P 19/32* | (2006.01) |
| *C07H 19/207* | (2006.01) |

(52) U.S. Cl.
CPC ............... *C12P 19/32* (2013.01); *C07H 1/00* (2013.01); *C07H 19/207* (2013.01); *C12N 9/1029* (2013.01); *C12P 7/24* (2013.01); *C12P 7/26* (2013.01); *C12P 7/42* (2013.01); *C12P 13/001* (2013.01); *C12P 13/005* (2013.01); *C12Y 203/01* (2013.01)

(58) Field of Classification Search
CPC combination set(s) only.
See application file for complete search history.

(56) References Cited

PUBLICATIONS

Saito, et al., "Metabolite Profiling Reveals YihU as a Novel Hydroxybutyrate Dehydrogenase for Alternative Succinic Semialdehyde Metabolism in *Escherichia coli*", Journal of Biological Chemistry, vol. 284, Issue 24, Jun. 12, 2009, pp. 16442-16452.
Samsonova, et al., "Molecular cloning and characterization of *Escherichia coli* K12 ygjG gene", BMC Microbiology, vol. 3, No. 2, Jan. 31, 2003, 10 pages.

Sanders, et al., "Characterization of the Human ω-oxidation Pathway for ω-hydroxy-very-long-chain Fatty Acids", The FASEB Journal, vol. 22, Jun. 2008, pp. 2064-2071.
Sanders, et al., "Evidence for Two Enzymatic Pathways for ω-oxidation of Docosanoic Acid in Rat Liver Microsomes", Journal of Lipid Research, ASBMB, vol. 46, 2005, pp. 1001-1008.
Satoh, et al., "Enzyme-catalyzed poly(3-hydroxybutyrate) synthesis from acetate with CoA recycling and NADPH Regeneration in Vitro", Journal of Bioscience and Bioengineering, vol. 95, Issue 4, 2003, pp. 335-341.
Scheller, et al., "Generation of the Soluble and Functional Cytosolic Domain of Microsomal Cytochrome P450 52A3", Journal of Biological Chemistry, vol. 269, No. 17, 1994, pp. 12779-12783.
Seedorf, et al., "The Genome of Clostridium Kluyveri, a Strict Anaerobe with Unique Metabolic Features", PNAS, vol. 105, No. 6, Feb. 12, 2008, pp. 2128-2133.
Shen, et al., "Driving Forces Enable High-Titer Anaerobic 1-Butanol Synthesis in *Escherichia coli*", Applied and Environmental Microbiology, vol. 77, No. 9, May 2011, pp. 2905-2915.
Slater, et al., "Multiple β-Ketothiolases Mediate Poly(β-Hydroxyalkanoate) Copolymer Synthesis in Ralstonia eutropha", Journal of Bacteriology, vol. 180 No. 8, Apr. 1998, pp. 1979-1987.
Suzuki, et al., "GriC and GriD Constitute a Carboxylic Acid Reductase Involved in Grixazone Biosynthesis in Streptomyces griseus", Journal of Antibiotics, vol. 60, No. 6, Jun. 5, 2007, pp. 380-387.
Venkitasubramanian, et al., "Aldehyde Oxidoreductase as a Biocatalyst: Reductions of Vanillic Acid", Enzyme and Microbial Technology, vol. 42, Issue 2, Jan. 2008, pp. 130-137.
Wee, et al., "Biotechnological Production of Lactic Acid and Its Recent Applications", Food Technology and Biotechnology, vol. 44, No. 2, 2006, pp. 163-172.
Woolridge, et al., "Efflux of the Natural Polyamine Spermidine Facilitated by the Bacillus Subtilis Multidrug Transporter Blt", The Journal of Biological Chemistry, vol. 272, No. 14, 1997, pp. 8864-8866.
Yang, et al., "Value-added Uses for Crude Glycerol—a Byproduct of Biodiesel Production", Biotechnology for Biofuels, vol. 5, No. 13, Mar. 14, 2012, 10 pages.
Yonaha, et al., "4-Aminobutyrate : 2-oxoglutarate Aminotransferase of Streptomyces Griseus : Purification and Properties", European Journal of Biochemistry, 146, FEBS, 1985, pp. 101-106.

(Continued)

*Primary Examiner* — Kagnew H Gebreyesus
(74) *Attorney, Agent, or Firm* — William J. Simmons; Thomas H. Jenkins

(57) ABSTRACT

This document describes materials and methods for, for example, producing 6-hydroxyhexanoic acid using a β-ketothiolase or synthase and an alcohol O-acetyltransferase to form a 6-acetyloxy-3-oxohexanoyl-CoA intermediate. This document describes biochemical pathways for producing 6-hydroxyhexanoic acid using a β-ketothiolase or synthase and an alcohol O-acetyltransferase to form a 6-acetyloxy-3-oxohexanoyl-CoA intermediate. 6-hydroxyhexanoic acid can be enzymatically converted to adipic acid, caprolactam, 6-aminohexanoic acid, hexamethylenediamine or 1,6-hexanediol. This document also describes recombinant hosts producing 6-hydroxyhexanoic acid as well as adipic acid, caprolactam, 6-aminohexanoic acid, hexamethylenediamine and 1,6-hexanediol.

26 Claims, 25 Drawing Sheets
Specification includes a Sequence Listing.

(56) References Cited

PUBLICATIONS

Zhuang, et al., "Divergence of Function in the Hot Dog Fold Enzyme Superfamily: The Bacterial Thioesterase YciA†", Biochemistry, vol. 47, No. 9, Feb. 2, 2008, pp. 2789-2796.

Musser, Michael Tuttle, "Adipic Acid", Ullmann's Encyclopedia of Industrial Chemistry, Jun. 15, 2000.

Anton, et al., "Polyamides Fibers", Encyclopedia of Polymer Science and Technology, John Wiley & Sons, Inc., 2001.

Barker, et al., "Enzymatic Reactions in the Degradation of 5-Aminovalerate by Clostridium Aminovalericum", Journal of Biological Chemistry, vol. 262, No. 19, 1987, pp. 8994-9003.

Bartsch, et al., "Molecular Analysis of Two Genes of the *Escherichia coli* Gab Cluster: Nucleotide Sequence of the Glutamate:Succinic Semialdehyde Transaminase Gene (gabT) and Characterization of the Succinic Semialdehyde Dehydrogenase Gene (gabD)", Journal of Bacteriology, vol. 172, No. 12, Dec. 1990, pp. 7035-7042.

Becker, et al., "Metabolic Flux Engineering of l-lysine Production in Corynebacterium Glutamicum—Over Expression and Modification of G6P Dehydrogenase", Journal of Biotechnology, vol. 132, Issue 2, Oct. 31, 2007, pp. 99-109.

Bellmann, et al., "Expression Control and Specificity of the Basic Amino Acid Exporter LysE of Corynebacterium Glutamicum", Microbiology, vol. 147, 2001, pp. 1765-1774.

Bond-Watts, et al., "Biochemical and Structural Characterization of the trans-Enoyl-CoA Reductase from Treponema Denticola", Biochemistry, vol. 51, No. 34, 2012, pp. 6827-6837.

Brigham, et al., "Engineering Ralstonia eutropha for Production of Isobutanol from CO2, H2, and O2", Advanced Biofuels and Bioproducts, Chapter 39, Jan. 2013, pp. 1065-1090.

Budde, et al., "Roles of Multiple Acetoacetyl Coenzyme A Reductases in Polyhydroxybutyrate Biosynthesis in Ralstonia eutropha H16", Journal of Bacterialogy, vol. 192 No. 20, Oct. 2010, pp. 5319-5328.

Bugg, et al., "The Emerging Role for Bacteria in Lignin Degradation and Bio-product Formation", Current Opinion in Biotechnology, vol. 22, Issue 3, Jun. 2011, pp. 394-400.

Cantu, et al., "Thioesterases: A New Perspective Based on Their Primary and Tertiary Structures", Protein Science, vol. 19, Issue 7, May 17, 2010, pp. 1281-1295.

Dellomonaco, et al., "Engineered Reversal of the β-oxidation Cycle for the Synthesis of Fuels and Chemicals", Nature, vol. 476, Aug. 18, 2011, pp. 355-359.

Elkins, et al., "Substrate Specificity of the RND-Type Multidrug Efflux Pumps AcrB and AcrD of *Escherichia coli* Is Determined Predominately by Two Large Periplasmic Loops", Journal of Bactiriology, vol. 184, No. 23, Dec. 2002, pp. 6490-6499.

Fukui, et al., "Expression and Characterization of (R)-Specific Enoyl Coenzyme A Hydratase Involved in Polyhydroxyalkanoate Biosynthesis by Aeromonas Caviae", Journal of Bacterialogy, vol. 180, No. 3, Feb. 1998, pp. 667-673.

Gloerich, et al., "Peroxisomal Trans-2-enoyl-CoA Reductase is Involved in Phytol Degradation", FEES Letters, vol. 580, 2006, pp. 2092-2096.

Guerrillot, et al., "Purification and Characterization of Two Aldehyde Dehydrogenases from Pseudomonas Aeruginosa", European Journal of Biochemestry, vol. 81, 1977, pp. 185-192.

Haywood, et al., "Characterization of Two 3-Ketothiolases Possessing Differing Substrate Specificities in the Polyhydroxyalkanoate Synthesizing Organism Alcaligenes Eutrophus", FEMS Microbiology Letters, vol. 52, Issues 1-2, Jul. 1988, pp. 91-96.

Hermann, Thomas, "Industrial Production of Amino Acids by Coryneform Bacteria", Journal of Biotechnology, vol. 104, Issues 1-3, Sep. 4, 2003, pp. 155-172.

Herzog, et al., "Hexamethylenediamine", Ullmann's Encyclopedia of Industrial Chemistry, Jan. 15, 2012.

Huhn, et al., "Identification of the Membrane Protein SucE and its Role in Succinate Transport in Corynebacterium Glutamicum", Applied Microbiology and Biotechnology, vol. 89, No. 2, 2011, pp. 327-335.

Inui, et al., "Fatty Acid Synthesis in Mitochondria of Euglena Gracilis", European Journal of Biochemistry, vol. 142, Issue 1, Jul. 1984, pp. 121-126.

Iwaki, et al., "Cloning and Characterization of a Gene Cluster Involved in Cyclopentanol Metabolism in Comamonas sp. Strain NCIMB 9872 and Biotransformations Effected by *Escherichia coli*-Expressed Cyclopentanone 1,2-Monooxygenase", Applied and Environmental Microbiology, vol. 68, No. 11, 2002, pp. 5671-5684.

Iwaki, et al., "Identification of a Transcriptional Activator (ChnR) and a 6-Oxohexanoate Dehydrogenase (ChnE) in the Cyclohexanol Catabolic Pathway in Acinetobacter sp. Strain NCIMB 9871 and Localization of the Genes That Encode Them", Applied and Environmental Microbiology, vol. 65, No. 11, 1999, pp. 5158-5162.

Jarboe, Laura R., "YqhD: A Broad-substrate Range Aldehyde Reductase with Various Applications in Production of Biorenewable Fuels and Chemicals", Applied Microbiology and Biotechnology, vol. 89 Issue 2, Jan. 2011, pp. 249-257.

Jaremko, et al., "The Initial Metabolic Conversion of Levulinic Acid in Cupriavidus Necator", Journal of Biotechnology, vol. 155, Issue 3, Sep. 20, 2011, pp. 293-298.

Kaulmann, et al., "Substrate Spectrum of ω-transaminase from Chromobacterium Violaceum DSM30191 and its Potential for Biocatalysis", Enzyme and Microbial Technology, vol. 41, No. 5, Oct. 2007, pp. 628-637.

Kim, Ki-Han, "Purification and Properties of a mine α-Ketoglutarate Transaminase from *Escherichia coli*", The Journal of Biological Chemistry, vol. 239, No. 3, 1964, pp. 783-786.

Kopke, et al., "2,3-Butanediol Production by Acetogenic Bacteria, an Alternative Route to Chemical Synthesis, Using Industrial Waste Gas", Applied and Environmental Microbiology, vol. 77, No. 15, Aug. 2011, pp. 5467-5475.

Larroy, et al., "Characterization of the Saccharomyces cerevisiae YMR318C (ADH6) Gene Product as a Broad Specificity NADPH-dependent Alcohol Dehydrogenase: Relevance in Aldehyde Reduction", Biochemistry Journal, vol. 361, 2002, pp. 163-172.

Lee, et al., "Metabolic Engineering of Pentose Phosphate Pathway in Ralstoniaeutropha for Enhanced Biosynthesis of Poly-β-Hydroxybutyrate", Biotechnology Progress, vol. 19, Issue 5, 2003, pp. 1444-1449.

Lee, et al., "Synthesis of Pure meso-2,3-Butanediol from Crude Glycerol Using an Engineered Metabolic Pathway in *Escherichia coli*", Applied Biochemistry and Biotechnology, vol. 166, Issue 7, Apr. 2012, pp. 1801-1813.

Li, et al., Biodegradation, 22, 2011, pp. 1215-1225.

Lim, et al., "Amplification of the NADPH-Related Genes zwf and gnd for the Oddball Biosynthesis of PHB in an *E. coli* Transformant Harboring a Cloned phbCAB Operon", Journal of Bioscience and Bioengineering, vol. 93, Issue 6, 2002, pp. 543-549.

Liu, et al., Microbiology, 155, 2009, pp. 2078-2085.

Liu, et al., "Production and Characterization of Medium-chain-length Polyhydroxyalkanoate with High 3-hydroxytetradecanoate Monomer Content by fadB and fadA Knockout Mutant of Pseudomonas Putida KT2442", Applied Microbiology and Biotechnology, vol. 76, Issue 5, Oct. 2007, pp. 1153-1159.

Lopez-Sanchez, et al., "Tetralin-Induced and ThnR-Regulated Aldehyde Dehydrogenase and β-Oxidation Genes in Sphingomonas macrogolitabida Strain TFA", Applied Environmental Microbialogy, vol. 76, No. 1, 2010, pp. 110-118.

Lutke-Eversloh, et al., "Biochemical and Molecular Characterization of a Succinate Semialdehyde Dehydrogenase Involved in the Catabolism of 4-Hydroxybutyric Acid in Ralstonia Eutropha", FEMS Microbiology Letters, vol. 181, 1999, pp. 63-71.

Martin, et al., "High-titer Production of Monomeric Hydroxyvalerates From Levulinic Acid in Pseudomonas Putida", Journal of Biotechnology, vol. 139, Issue 1, Jan. 1, 2009, pp. 61-67.

Meijnen, et al., "Improved p-hydroxyBenzoate Production by Engineered Pseudomonas Putida S12 by Using a Mixed-substrate Feeding Strategy", Applied Microbiology and Biotechnology, vol. 90, Feb. 2, 2011, pp. 885-893.

Naggert, et al., "Cloning, Sequencing, and Characterization of *Escherichia coli* Thioesterase 11", Journal of Biological Chemistry, vol. 266, No. 17, 1991, pp. 11044-11050.

Neyfakh, Alexander A., "The Multidrug Efflux Transporter of Bacillus Subtilis is a Structural and Functional Homolog of the

(56) References Cited

PUBLICATIONS

*Staphylococcus* NorA Protein", Antimicrobial Agents and Chemotherapy, vol. 36, No. 2, Feb. 1992, pp. 484-485.

Ng, et al., "Quinolone Resistance Mediated by norA: Physiologic Characterization and Relationship to flqB, a Quinolone Resistance Locus on the *Staphylococcus aureus* Chromosome", Antimicrobial Agents Chemotherapy, vol. 38, No. 6, 1994, pp. 1345-1355.

Nishimaki, et al., "Studies on the Metabolism of Unsaturated Fatty Acids XIV. Purification and Properties of NADPH-Dependent trans-2-Enoyl-CoA Reductase of *Escherichia coli* K-12", The Journal of Biochemistry, vol. 95, No. 5, 1984, pp. 1315-1321.

Nogales, Juan, et al., "Characterization of the Last Step of the Aerobic Phenylacetic Acid Degradation Pathway", Microbrology, vol. 153, Feb. 2007, pp. 357-365.

Nomura, et al., "Expression of 3-Ketoacyl-Acyl Carrier Protein Reductase (fabG) Genes Enhances Production of Polyhydroxyalkanoate Copolymer from Glucose in Recombinant *Escherichia coli* JM109", Applied and Environmental Microbialogy, vol. 71, No. 8, Aug. 2005, pp. 4297-4306.

Ohashi, et al., "Continuous Production of Lactic Acid from Molasses by Perfusion Culture of Lactococcus Lactis Using a Stirred Ceramic Membrane Reactor", Journal of Bioscience and Bioengineering, vol. 87, Issue 5, 1999, pp. 647-654.

Papanikolaou, et al., "Citric Acid Production by Yarrowia Lipolytica Cultivated on Olive-Mill Wastewater-Based Media", Bioresource Technology, vol. 99, Issue 7, May 2008, pp. 2419-2428.

Perez-Pantoja, et al., "Metabolic Reconstruction of Aromatic Compounds Degradation from the Genome of the Amazing Pollutant-Degrading Bacterium Cupriavidus Necator JMP134", FEMS Microbiology Reviews, vol. 32, 2008, pp. 736-794.

Prybylski, et al., "Third-Generation Feed Stocks for the Clean and Sustainable Biotechnological Production of Bulk Chemicals: Synthesis of 2-Hydroxyisobutyric Acid", Energy, Sustainability and Society, vol. 2, No. 11, Jul. 16, 2012, 9 pages.

Ramsay, et al., "Use of a Nylon Manufacturing Waste as an Industrial Fermentation Substrate", Applied and Environmental Microbiology, vol. 52, No. 1, Jul. 1986, pp. 152-156.

Ritz, et al., "Caprolactam", Ullmann's Encyclopedia of Industrial Chemistry, Jun. 15, 2000.

FIGURE 6

| SEQ ID NO | Organism | GENBANK reference | Amino acid sequence |
|---|---|---|---|
| 1 | Cupriavidus necator | AAC38322.1 | MTREVVVSGVRTAIGTFGGSLKDVAPAELGALVVREALARAQVSGDDVGHVVFGNVIQTEPRDMYLGRVAA VNGGVTIINAPALTVNRLCGSGLQAIVSAAQTILLGDTDVAIGGGAESMSRAPYLAPAARWGARMGDAGLVD MMLGALHDPFHRIHMGVTAENVAKEYDISRAQQDEAALESHRRASAAIKAGYFKDQIVPVVSKGRKGDVTFD TDEHVRHDATIDDMTKLRPVFVKENGTVTAGNASGLNDAAAAVVMMERAEAERRGLKPLARLVSYGHAGVD PKAMGIGPVPATKJALERAGLQVSDLDVIEANEAFAAQACAVTKALGLDPAKVNPNGSGISLGHPIGATGALITV KALHELNRVQGRYALVTMCIGGGQGIAAIFERI |
| 2 | Mycobacterium marinum | ACC40567.1 | MSPITREERLERRIQDLYANDPQFAAAKPATAITAAIERPGLPLPQIIETVMTGYADRPALAQRSVEFVTDAGTG HTTLRLLPHFETISYGELWDRISALADVLSTEQTVKPGDRVCLLGFNSVDYATIDMTLARLGAVAVPLQTSAAITQ LQPIVAETQPTMIAASVDALADATELALSGQTATRVLVFDHHRQVDAHRAAVESARERLAGSAVVETLAEAIAR GDVPRGASAGSAPGTDVSDDSLALLIYTSGSTGAPKGAMYPRRNVATFWRKRTWFEGGYEPSITLNFMPMSH VMGRQILYGTLCNGGTAYFVAKSDLSTLFEDLALVRPTELTFVPRVWDMVFDEFQSEVDRRLVDGADRVALEA QVKAEIRNDVLGGRYTSALTGSAPISDEMKAWVEELLDMHLVEGYGSTEAGMILIDGAIRRPAVLDYKLVDVPD LGYFLTDRPHPRGELLVKTDSLFPGYYQRAEVTADVFDADGFYRTGDIMAEVGPEQFVYLDRRNNVLKLSQGEF VTVSKLEAVFGDSPLVRQIYIYGNSARAYLLAVIVPTQEALDAVPVEELKARLGDSLRQSGADAPVLVTVCRAAAALLGGSASD TTPWTLENGLLTGIRKLARPQLKKHYGELLEQIYTDLAHGQADELRSLRQSGADAPVLVTVCRAAAALLGGSASD VQPDAHFTDLGGDSLSALSFTNLLHEIFDIEVPVGVIVSPANDLQALADYVEAARKPGSSRPTFASVHGASNGQV TEVHAGDLSLDKFIDAATLAEAPRLPAANTQVRTVLLTGATGFLGRYLALEWLERMDLVDGKLICLVRAKSDTEA RARLDKTFDSGDPELLAHYRALAGDHLEVLAGDKGEADLGLDRQTWQRLADTVDLIVDPAALVNHVLPYSQLF GPNALGTAELLRLALTSKIPKPYSYTSTIGVADQIPPSAFTEDADIRVISATRAVDDSYANGYSNSKWAGEVLLREA HDLCGLPVAVFRCDMILADTTWAGQLNVPDMFTRMILSLAATGIAPGSFYELAADGARQAHYDGLPVEFIAE AISTILGAQSQDGFHTYHVMNPYDDGIGLDEFVDWLNESGCPIQRIADYGDWLQRFETALRALPDRQRHSSLLP LLHNYRQPERPVRGSIAPTDRFRAAVQEAKIGPDKIPHVGAPIIVKYVVSDLRLLGLL |

FIGURE 6 (Continued)

| SEQ ID NO | Organism | GENBANK reference | Amino acid sequence |
|---|---|---|---|
| 3 | Mycobacterium smegmatis | ABK71854.1 | MTSDVHDATDGVTETALDDEQSTRRIAELYATDPEFAAAAPLPAVVDAAHKPGLRLAEILQTLFTGYGDRPALG YRARELATDEGGRTVTRLLPREDTLTYAQVMWSRVQAVAAALRHNFAQPIYPGDAVATIGFASPDYLTLDLVCAY LGLVSVPLQHNAPVSRLAPILAEVEPRILTVSAEYLDLAVESVRDVNSVSQLVVFDHHPEVDDHRDALARAREQL AGSKGIAVTTLDAIADEGAGLPAEPIYTADHDQRLAMILYTSGSTGAPKGAMYTEAMVARLWTMSFITGDPTPVI NVNFMPLNHLGGRIPISTAVQNGGTSYFVPESDMSTLFEDLALVRPTELGLVPRVADMLYQHHLATVQRLVTQ GADELTAEKQAGAELREQVLGGRVITGFVSTAPLAAEMRAFLDITLGAHIVDGYGLTETGAVTRDGVIVRPPVID YKLIDVPELGYFSTDKPYPRGELLVRSQTLTPGYYKRPEVTASVFDRDGYYHTGDVMAETAPDHLVYVDRRNNV LKLAQGEFVAVANLEAVFSGAAVLRVQIFVYGNSERSFLLAVVPTPEALEQYDPAALKAALADSLQRTARDAELQ SYEVPADFIVETEPFSAANGLLSGVGKLLRPNLKDRYGQRLEQMYADIAATQANQLRELRRAAATQPVIDTLTQ AAATILGTGSEVASDAHFTDLGGDSLSALTLSNLLSDFFGFEVPGTIVNPATNLAQLAQHIEAQRTAGDRRPSF TTVHGADATEIRASELTLDKFIDAETLRAAPGLPKVTTEPRTVLLSGANGWLGRFLTLQMLERLAPVGGTLTIVR GRDDAAARARLTQAYDTDPELSRFAELADRHLRVVAGDIGDPNLGLTPEIWHRLAAEVDLVVHPAALVNHVL PYRQLFGPNVVGTAEVIKLALTERIKPVTYLSTVSVAMGIPDFEEDGDIRTVSPVRPLDGGYANGYGNSKWAGE VLLREAHDLCGLPVATFRSDMILAHPRYRGQVNVPDMFTRLLLSLLLTGVAPRSFYIGDGERPRAHYPGLTVDFV AEAVTTLGAQQREGVSYDVMNPHDDGISLDVFVDWLRAGHPIDRVDDYDDWVRRFETALTALPEKRRAQT VLPLLHAFRAPQAPLRGAPEPTEVHAAVRTAKVGPGDIPHLDEALIDKYIRDLREFGLI |
| 4 | Segniliparus rugosus | EFV11917.1 | MGDGEERAKRFFQRIGELSATDPQFAAAAPDPAVVEAVSDPSLSFTRYLDTLMRGYAERPALAHRVGAGYETIS YGELWARVGAIAAAWQADGLAPGFVATVGFTSPDYVAVDLAAARSGLVSVPLQAGASLAQLVGILEETEPKV LAASASSLEGAVACALAAPSVQRLVVFDLRGPDASESAADERRGALADAEEQLARAGRAVVVETILADLAARGE ALPEAPLFEPAEGEDPLALLIYTSGSTGAPKGAMYSQRLVSQLWGRTPVVPGMPNISLHYMPLSHSYGRAVLAG ALSAGGTAHFTANSDLSTLFEDIALARPTFLAVPRVCEMLFQESQRGQDVAELRERVLGGRLLVAVCGSAPLSP EMRAFMEEVLGFPLLDGYGSTEALGVMRNGIIQRPPVIDYKLLVDVPELGYRTTDKPYPRGELCIRSTLSGYYKR PEITAEVFDAQGYYKTGDVMAEIAPDHLVYVDRSKNVLKLSQGEFVAVAKLEAAYGTSPYVKQIFVYGNSERSFL LAVVVPNAEVLGARDQEEAKPLIAASLQKIAKEAGLQSYEVPRDFLIETEPFTTQNGLLSEVGKLLRPKLKARYGE ALEARYDEIAHGQADELRALRDGAGQRPVVETVVRAAVAISGSEGAEVGPEANFADLGGDSLSALSLANLLHDV FEVEVPVRIIGPTASLAGIAKHIEAERAGASAPTAASVHGAGATRIRASELTLEKFLPEDLLAAAKGLPAADQVRT VLLTGANGWLGRFLALEQLERLARSGQDGGKLICLVRGKDAAAARRIEETLGTDPALAARFAELAEGRLLEVVP GDVGEPKFGLDDAAWDRLAEEVDVIVHPAALVNHVLPYHQLFGPNVVGTAEIIRLAITAKRKPVTYLSTVAVAA GVEPSSFEEDGDIRAVVPERPLGDGYANGYGNSKWAGEVILREAHELVGLPVAVFRSDMILAHTRYTGQLNVP DQFTRLVLSLLATGIAPKSFYQQGAAGERCQRAHYDGIPVDFTAEAITTLGAEPSWFDGGAGFRSFDVFNPHHD GVGLDEFVDWLIEAGHPISRIODHKEWFARFETAVRGLPEAQRQHSLLPLLRAYSFPHPPVDGSVVPTGKFQGA VKAAQVGSDHDVPHLGKALIVKYADDLKALGLL |

FIGURE 6 (Continued)

| SEQ ID NO | Organism | GENBANK reference | Amino acid sequence |
|---|---|---|---|
| 5 | Mycobacterium massiliense | EIV11143.1 | MTNETNPQQEQLSRRIESLRESDPQFRAAQPDPAVAEQVLRPGLHLSEAIAALMTGYAERPALGERARELVIDQ DGRTTLRLLPRFDTTYGELWSRTTSVAAAWHHDATHPVKAGDLVATLGFTSIDYTVLDLAIMILGGVAVPLQT SAPASQWTTILAEAEPNTLAVSIELIGAAMESVRATPSIKQVVVFDYTPEVDDQREAFEAASTQLAGTGIALETLD AVIARGAALPAAPLYAPSAGDDPLALLIYTSGSTGAPKGAMHSENIVRRWWIREDVMAGTENLPMIGLNFMP MSHIMGRGTLTSTLSTGGTGYFAASSDMSTLFEDMELIRPTALALVPRVCDMVFQRFQTEVDRRLASGDTASA EAVAAEVKADIRDNLFGGRVSAVMVGSAPLSEELGEFIESCFELNLTDGYSTEAGMVFRDGIVQRPPVIDYKLV DVPELGYFSTDKPHPRGELLLKTDGMFLGYYKRPEVTASVFDADGFYMTGDIVAELAHDNIEIIDRRNNVLKLSQ GEFVAVATLEAEYANSPVVHQIYVYGSSERSYILAVVPTPEAVAAAKGDAAALKTTIADSLQDIAKEIQLQSYEV PRDFIIEPQPFTQGNGLLTGIAKLARPNLKAHYGPRLEQMYAEIAEQQAAELRALHGVDPDKPALETVLKAAQAL LGVSSAELAADAHFTDLGGDSLSALSFSDLLRDIFAVEVPVGVIVSAANDLGGVAKFVDEQRHSGGTRPTAETV HGAGHTEIRAADLTLDKFIDEATLHAAPSLPKAAGIPHTVLLTGSNGYLGHYLALEWLERLDKTDGKLIVVRGKN AEAAYGRLEEAFDTGDTELLAHFRSLADKHLEVLAGDIGDPNLGLDADTWQRLADTVDVIVHPAALVNHVLPY NQLFGPNVVGTAEIIKLAITTKIKPVTYLSTVAVAAYVDPTTFDEESDIRLISAVRPIDDGYANGYGNAKWAGEVLL REAHDLCGLPVAVFRSDMILAHSRYTGQLNVPDQFTRLILSLIATGIAPGSFYQAQTTGERPLAHYDGLPGDFTA EAITTLGTQVPEGSEGFVTYDCVNPHADGISLDNFVDWLIEAGYPIARIDNYTEWFTRFDTAIRGLSEKQKQHSLL PLLHAFEQPSAAENHGVVPAKRFQHAVQAAGIGPVGQDGTTDIPHLSRRLIVKYAKDLEQLGLL |
| 6 | Segniliparus rotundus | ADG98140.1 | MTQSHTQGPQASAAHSRLARRAAELLATDPQAAATLPDPEVVRQATRPGLRLAERVDAILSGYADRPALGQRS FQTVKDPITGRSSVELLPTFDTITYRELRERATAIASDLAHHPQAPAKPGDFLASIGFISVDYVAIDIAGVFAGLTAV PLQTGATLATLTAITAETAPTLFAASIEHLPTAVDAVLATPSVRRLLVFDYRAGSDEDREAVEAAKRKIADAGSSVL VDVLDEVIARGKSAPKAPLPPATDAGDDSLLIYTSGSTGTPKGAMYPERNVAHFWGGVWAAAFDEDAAPP VPAINITFLPLSHVASRLSLMPPTLARGGLMHFVAKSDLSTLFEDLKLARPTNLFLVPRRVVEMLYQHYQSELDRRG VQDGTREAEAVKDDLRTGLLGGRILTAGFGSAPLSAELAGFIESLLQIHLVDGYGSTEAGPVWRDGYLVKPPVTD YKLIDVPELGYFSTDSPHPRGELAIKTQTILPGYYKRPETTAEVFDEDGFYLTGDVVAQIGPEQFAYVDRRKNVLKL SQGEFVTLAKLEAAYSSSPLVRQLFVYGSSERSYILLAVIVPTPDALKKFGVGEAAKAALGESLQKIARDEGLQSYEV PRDFIIETDPFTVENGLLSDARKSLRPKLKEHYGERLEAMYKELADGQANELRDIRRGVQQRPTLETVRRAAAA MLGASAAEIKPDAHFTDLGGDSLSALTFSNFLHDLFEVDPVGVIVSAANTLGSVAEHIDAQLAGGRARPTFAT VHGKGSTTIKASDLTLDKFIDEQTLEAAKHLPKPADPPRTVLLTGANGWLGRFLALEWLERLAPAGGKLITIVRGK DAAQAKARLDAAYESGDPKLAGHYQDLAATTLEVLAGDFSEPRLGLDEATWNRLADEVDFISHPGALVNHVLP YNQLFGPNVAGVAEIIKLAITTRIKPVTYLSTVSVAAGVEPSALDEDGDIRTVSAERSVDEGYANGYGNSKWGGE VLLREAHDRTGLPVRVFRSDMILAHQKYTGQVNATDQFTRLVQSLLATGLAPKSFYELDAQGNRQAHYDGIP VDFTAESITTLGDGLEGYRSYNVFNPHRDGVGLDEFVDWLIEAGHPITRIDDYDQWLSRFETSLRGLPESKRQA SVLPLLHAFARPGPAVDGSPFRNTVFRTDVQKAKIGAEHDIPHLGKALVLKYADDIKQLGLL |

FIGURE 6 (Continued)

| SEQ ID NO | Organism | GENBANK reference | Amino acid sequence |
|---|---|---|---|
| 7 | Chromobacterium violaceum | AAQ59697.1 | MQKQRTTSQWRELDAAHHLHPFTDTASLNQAGARVMTRGEGVYLWDSEGNKIIDGMAGLWCVNVGYGRK DFAEAARRQMEELPFYNTFFKTTHPAVVELSSLLAEVTPAGFDRVFYTNSGSESVDTMIRMVRRYWDVQGKPE KKTLIGRWNGYHGSTIGGASLGGMKYMHEQGDLPIPGMAHIEQPWWYKHGKDMTPDEFGVVAARWLEEKI LEIGADKVAAFVGEPIQGAGGVIVPPATYWPEIERICRKYDVLLVADEVICGFGRTGEWFGHQHFGFQPDLFTA AKGLSSGYLPIGAVFVGKRVAEGLIAGGDFNHGFTYSGHPVCAAVAHANVAALRDEGIVQRVKDDIGPYMQKR WRETFSRFEHVDDVRGVGMVQAFTLVKNKAKRELFPDFGEIGTLCRDIFFRNNLIMRACGDHIVSAPPLVMTR AEVDEMLAVAERCLEEFEQTLKARGLA |
| 8 | Pseudomonas aeruginosa | AAG08191.1 | MNARLHATSPLGDADLVRADQAHYMHGYHVFDDHRVNGSLNIAAGDGAYIYDTAGNRYLDAVGGMWCTNI GLGREEMARTVAEQTRLLAYSNPFCDMANPRAIELCRKLAELAPGDLDHVFLTTGGSTAVDTAIRLMHYQNC RGKRAKKHVITRINAYHGSTFLGMSLGGKSADRPAEFDFLDERIHHLACPYYYRAPEGLGEAEFLDGLVDEFERKI LELGADRVGAFISEPVFGSGGVIVPPAGYHRRMWELCQRYDVLYISDEVVTSFGRLGHFFASQAVFGVQPDILT AKGLTSGYQPLGACIFSRRIWEVIAEPDKGRCFSHGFTYSGHPVACAAALKNIEIIEREGLLAHADEVGRYFEERL QSLRDLPIVGDVRGMRFMACVEFVADKASKALFPESLNIGEWVHLRAQKRGLLVRPIVHLNVMSPPLILTREQV DTVVRVLRESIEETVEDLVRAGHR |
| 9 | Pseudomonas syringae | AAV39893.1 | MSANNPQTLEWQALSSEHHLAPFSDYKQLKEKGPRIITRAEGVYLWDSEGNKILDGMSGLWCVAIGYGREELA DAASKQMRELPYYNLFFQTAHPPVLELAKAISDIAPEGMNHVFFTGSGSEGNDTMLRMVRHYWALKGQPNK KTIISRVNGYHGSTVAGASLGGMTYMHEQGDLPIPGVVHIPQPYVWFGEGGDMTPDEFGIWAAEQLEKKILELG VENVGAFIAEPIQGAGGVIVPPDSYWPKIEILSRYDILFAADEVICGFGRTSEWFGSDFYGLRPDMMTIAKGLTS GYVPMGGLIVRDEIVAVLNEGGDFNHGFTYSGHPVAAAVALENIRILREEKIVERVRSETAPYLQKRLRELSDHPL VGEVRGVGLLGAIELVKDKTTRERYTDKGAGMICRTFCFDNGLIMRAVGDTMIIAPPLVISFAQIDELVEKARTCL DLTLAVLQG |
| 10 | Rhodobacter sphaeroides | ABA81135.1 | MTRNDATNAAGAVGAAMRDHILLPAQEMAKLGKSAQPVLTHAEGIYVHTEDGRRLIDGPAGMWCAQVGYG RREIVDAMAHQAMVLPYASPWYMATSPAARLAEKIATLTPGDLNRIFFTGGSTAVDSALRFSEFYNNVLGRP QKKRIIVRYDGYHGSTALTAACTGRTGNWPNFDIAQDRISFLSSPNPRHAGNRSQEAFLDDLVQEFEDRIESLGP DTIAAFLAEPILASGGVIIPPAGYHARFKAICEKHDILYISDEVTGFGRCGEWFASEKVFGVVPDIITFAKGVTSGY VPLGGLAISEAVLARISGENAKGSWFTNGYTYSNQPVACAAALANIELMEREGIVDQAREMADYFAAALASLR DLPGVAETRSVGLVGCVQCLLDPTRADGTAEDKAFTLKIDERCFELGLIVRPLGDLCVISPPLIISRAQIDEMVAIM RQAITEVSAAHGLTAKEPAAV |

FIGURE 6 (Continued)

| SEQ ID NO | Organism | GENBANK reference | Amino acid sequence |
|---|---|---|---|
| 11 | Escherichia coli | AAA57874.1 | MNRLPSSASALACSAHALNLJEKRTLDHEEMKALNREVIEYFKEHVNPGFLEYRKSVTAGGDYGAVEWQAGSL NTLVDTQGGQEFIDCLGGFGIFNVGHRNPVVVSAVQNQLAKQPLHSQELLDPLRAMLAKTLAALTPGKLKYSFFC NSGTESVEAALKLAKAYQSPRGKFTFIATSGAFHGKSLGALSATAKSTFRKPFMPLLPGFRHVPFGNIEAMRTAL NECCKTGDDVAAVILEPIQGEGGVILPPPGYLTAVRKLCDEFGALMILDEVQTGMGRTGKMFACEHENVQPDIL CLAKALGGGVMPIGATIATEEVFSSVLFDNPFLHTTTFGGNPLACAAALATINVLLEQNLPAQAEQKGDMLLDGF RQLAREYPDLVQEARGKGMLMAIEFVDNEIGYNFASEMFRQRVLVAGTLNNAKTIRIEPPLTLTIEQCELVIKAA RKALAAMRVSVEEA |
| 12 | Vibrio fluvialis | AEA39183.1 | MNKPQSWEARAETYSLYGFTDMPSLHQRGTVVVTHGEGPYIVDVNGRRYLDANSGLWNMVAGFDHKGLID AAKAQYERFPGYHAFFGRMSDQTVMLSEKLVEVSPFDSGRVFYTNSGSEANDTMVKMLWFLHAAEGKPQKR KILTRWNAYHGVTAVSASMTGKPYNSVFGLPLPGFVHLTCPHYWRYGEEGETEEQFVARLARELEETIQREGAD TIAGFFAEPVMGAGGVIPPAKGYFQAILPILRKYDIPVISDEVICGFGRTGNTWGCVTYDFTPDAIISSKNLTAGFF PMGAVILGPELSKRLETAIEAIEEFPHGFTASGHPVGCAIALKAIDVVMNEGLAENVRRLAPRFEERLKHIAERPNI GEYRGIGFMIWALEAVKDKASKTPFDGNLSVSERIANTCTDLGLICRPLGQSVVLCPPFILTEAQMDEMFDKLEK ALDKVFAEVA |
| 13 | Bacillus subtilis | CAA44858.1 | MKIYGIYMDRPLSQEENERFMSFISPEKREKCRRFYHKEDAHRTLLGDVLVRSVISRQYQLDKSDIRFSTQEYGKP CIPDLPDAHFNISHSGRWVICAFDSQPIGIDIEKTKPISLEIAKRFFSKTEYSDLLAKDKDEQTDYFYHLWSMKESFI KQEGKGLSLPLDSFSVRLHQDGQVSIELPDSHSPCYIKTYEVDPGYKMAVCAAHPDFPEDITMVSYEELL |
| 14 | Nocardia sp. NRRL 5646 | ABI83656.1 | MIETILPAGVESAELLEYPEDLKAHPAEEHLIAKSVEKRRRDFIGARHCARLALAELGEPPVAIGKGERGAPIWPR GVVGSLTHCDGYRAAAVAHKMRFRSIGIDAEPHATLPEGVLDSVSLPPEREWLKTTDSALHLDRLLFCAKEATYK AWWPLTARWLGFEEAHTFEIEDGSADSGMGTFHSELLVPGQTNDGGTPLLSFDGRWLIADGFILTAIAYA |
| 15 | Pseudomonas fluorescens | AAB60168 | MSTFVAKDGTQIYFKDWGSGKPVLFSHGWLLDADMWEYQMEYLSSRGYRTIAFDRRGFGRSDQPWTGNDY DTFADDIAQLIEHLDLKEVTLVGFSMGGGDVARYIARHGSARVAGLVLLGAVTPLFGQKPDYPQGVPLDVFARF KTELLKDRAQFISDFNAPFYGINKGQVVSQGVQTQTLQIALLASLKATVDCVTAFAETDFRPDMAKIDVPTLVIH GDGDQIVPFETTGKVAAELIKGAELKVYKDAPHGFAVTHACQLNEDILAFLKR |
| 16 | Escherichia coli | AAC74479.1 | MREAFICDGIRTPIGRYGGALSSVRADDLAAIPLRELLVRNPRLDAECIDDVILGCANQAGEDNRNVARMATLLA GLPQSVSGTTINRLCGSGLDALGFAARAIKAGDGDLLIAGGVESMSRAPFVMGKAASAFSRQAEMFDTTIGWR FVNPLMAQQFGTDSMPETAENVAELLKISREDQDSFALRSQQRTAKAQSSGILAEEIVPVVLKNKKGVVTEIQH DEHLRPETTLEQLRGLKAPFRANGVITAGNASGVNDGAAAAILIASEQMAAAQGLTPRARIVAMATAGVEPRLM GLGPVPATRRVLERAGLSIHDMDVIELNEAFAAQALGVLRELGLPDDAPHVNPNGGAIALGHPLGMSGARLAL AASHELHRRNGRYALCTMCIGVGQGIAMILERV |

FIGURE 6 (Continued)

| SEQ ID NO | Organism | GENBANK reference | Amino acid sequence |
|---|---|---|---|
| 17 | Saccharomyces cerevisiae | CAA85138.1 | MSEVSKWPAINPFHWGYNGTVSHIVGENGSIKLHLKDNKEQVDFDEFANKYVPTLKNGAQFKLSPYLFTGILQT LYLGAADFSKKFPVFYGREIVKFSDGGVCTADWLIDSWKKDYEFDQSTTSFDKKKFDKDEKATHPEGWPRLQPR TRYLKDNELEELRLEVDLPLVVILHGLAGGSHEPIIRSLAENLSRSGRFQVVVLNTRGCARSKITTRNLFTAYHTMDI REFLQREKQRHPDRKLYAVGCSFGATMLANYLGEEGDKSPLSAAATLCNPWDLLSAIRMSQDWWSRTLFSK NIAQFLTRTVQVNMGELGVPNGSLPDHPPTVKNPSFYMFTPENLIKAKSFKSTREFDEVYTAPALGFPNAMEYY KAASSINRVDTIRVPTLVINSRDDPVVGPDQPYSIVEKNPRILYCRTDLGGHLAYLDKDNNSWATKAIAEFFTKFD ELVV |
| 18 | Escherichia coli | CAA33612.1 | MNNIWWQTKGQGNVHLVLLHGWGLNAEVWRCIDEELSSHFTLHLVDLPGFGRSRGFGALSLADMAEAVLQ QAPDKAIWLGWSLGGLVASQIALTHPERVQALVTVASSPCFSARDEWPGIKPDVLAGFQQQLSDDFQRTVERF LALQTMGTETARQDARALKKTVLALPMPEVDVLNGGLEILKTVDLRQPLQNVSMPFLRLYGYLDGLVPRKVVP MLDKLWPHSESYIFAKAAHAPFISHPAEFCHLLVALKQRV |
| 19 | Clostridium aminobutyricum | CAB60036.2 | MDWKKIYEDRTCTADEAVKSIKSGDRVLFAHCVAEPPVLVEAMVANAAAYKNVTVSHMVTLGKGEYSKPEYK ENFTFEGWFTSPSTRGSIAEGHGQFVPVFFHEVPSLIRKDIFHVDVFMVMVSPPDHNGFCCVGVSSDYTMQAI KSAKIVLAEVNDQVPVVYGDTFVHVSEIDKFVETSHPLPEIGLPKIGEVEAAIGKHCASLIEDGSTLQLGIGAIPDA VLSQLKDKKHLGIHSEMISDGVVDLYEAGVIDCSQKSIDKGKMAITFLMGTKRLYDFAANNPKVELKPVDYINHP SVVAQCSKMVCINACLQVDFMGQIVSDSIGTKQFSGVGGQVDFVRGASMSIDGKGKAIIAMPSVAKKDGSM ISKIVPFIDHGAAVTTSRNDADYVVTEYGIAEMKGKSLQDRARALINIAHPDFKDELKAEFEKRFNAAF |
| 20 | Salmonella typhimurium | CAC48239.1 | MQNPYTVADYLLDRLAGCGIGHLFGVPGDYNLQFLDHVIDHPTLRWVGCANELNAAYAADGYARMSGAGAL LTTFGVGELSAINGIAGSYAEYVPVLHIVGAPCSAAQQRGELMHHTLGDGDFRHFYRMSQAISAASAILDEQNA CFEIDRVLGEMLAARRPGYIMLPADVAKKTAIPPTQALALPVHEAQSGVETAFRYHARQCLMNSRRIALLADFL AGRFGLRPLLQRWMAETPIAHATLLMGKGLFDEQHPNFVGTYSAGASSKEVRQAIEDADRVICVGTRFVDTLT AGFTQQLPAERTLEIQPYASRIGETWFNLPMAQAVSTLRELCLECAFAPPPTRSAGQPVRIDKGELTQESFWQT LQQYLKPGDIILVDQGTAAFGAAAALSLPDGAEVVLQPLWGSIGYSLPAAFGAQTACPDRRVILIGDGAAQLTIQ EMGSMLRDGQAPVLILLNNDGYTVERAIHGAAQRYNDIASWNWTQJPPALLNAAQQAECWRVTQAIQLAEVL ERLARPQRLSFIEVMLPKADLPELLRTVTRALEARNGG |

FIGURE 6 (Continued)

| SEQ ID NO | Organism | GENBANK reference | Amino acid sequence |
|---|---|---|---|
| 21 | Mycobacterium smegmatis | ABK74238.1 | MSSSPSPFGQNEWLVEEMYRKFRDDPSSVDPSWHEFLVDYSPEPTTDSASNGRTTTAAPVTPPTPAPAPAPEP KAAPKPAAKTEAKPAKPAKSATPAKGDESQILRGAAAAVVKNMNASLEVPTATSVRAIPAKLMIDNRVVINNHL KRTRGGKISFTHLLGYAIVQAVKKFPNMNRHFAVVDGKPTAITPAHTNLGLAIDLQGKDGNRSLVVAAIKRCET MRFGQFIAAYEDIVRRARDGKLTAEDFSGVTISLTNPGTLGTVHSVPRLMQGQGAIIGAGAMEYPAEFQGASE ERIADLGIGKLITLTSTYDHRIIQGAESGDFLRTIHQLLLDDDFFDEIFRELGIPYEPVRWRTDNPDSIEDKNARVIEL IAAYRNRGHGMADIDPLRLDNTRFRSHPDLDVNSHGLTLWDLDREFKVDGFAGVQRKKLRDILSVLRDAYCRH VGVEYTHILEPEQQRWIQERVETKHDKPTVAEQKYILSKLNAAEAEFTLQTKYVGQKRFSLEGAETVIPMMDA VIDQCAEHGLDEVVIAMPHRGRLNVLANIVGKPYYSQJFSEFEGNLNPSQAHGSGDVKYHLGATGTYIQMFGDN DIEVSLTANPSHLEAVDPVLEGLVRAKQDLLDTGEEGSDNRFSVVPLMLHGDAAFAGQGVVAETLNLALLRGYR TGGTIHIVVNNQIGFTTAPTDSRSSEYCTDVAKMIGAPIFHVNGDDPEACAWVARLAVDFRQAFKKDVVIDML CYRRGHNEGDDPSMTQPYMYDVIDTKRGSRKAYTEALIGRGDISMKEAEDALRDYQGQLERVFNEVRELEKH EIEPSESVEADQQIPSKLATAVDKAMLQRIGDAHLALPEGFTVHPRVRPVLEKRREMAYEGRIDWAFAELLALGS LIAEGKLVRLSGQDTQRGTFTQRHAVIVDRKTGEEFTPLQLLATNPDGTPTGGKFLVYNSALSEFAAVGFEYGYS VGNPDAMVLWEAQFGDFVNGAQSIIDEFISSGEAKWGQLSDVVLLPHGHEGQPDHTSGRIERFLQLWAEG SMTIAMPSTPANYFHLLRRHGKDGIQRPLIVFTPKSMLRNKAAVSDIRDFTESKFRSVLEEPMYTDGEGDRNKV TRLLLTSGKIYYELAARKAKENREDVAIVRIEQLAPLPRRRLAETLDRYPNVKEKFWVQEEPANQGAWPSFGLTL PEILPDHFTGLKRISRRAMSAPSSGSSKVHAVEQQEILDTAFG |
| 22 | Lactococcus lactis subsp. lactis | ADA65057.1 | MYTVGDYLLDRLHELGIEEIFGVPGDYNLQFLDQIISRKDMKWVGNANELNASYMADGYARTKAAAFLTTFG VGELSAVNGLAGSYAENLPVVEIVGSPTSKVQNEGKFVHHTLADGDFKHFMKMHEPVTAARTLLTAENATVEI DRVLSALLKERKPVYINLPVDVAAAKAEKPSLPLKKENPTSNTSDQEILNKIQESLKNAKKPIVITGHEIISFGLENTV TQFISKTKLPITTLNFGKSSVDETLPSFLGIYNGKLSEPNLKEFVESADFHLMLGVKLTDSSTGAFTHHLNENKMISL NIDEGKIFNESIQNFDFESLISSLLDLSGIEYKGKYHDKKQEDFVPSNALLSQDRLWQAVENLTQSNETIVAEQGTS FFGASSIFLKPKSHFIGQPLWGSIGYTFPAALGSQIADKESRHLLFIGDGSLQLTVQELGLAIREKINPICFHNNDGY TVEREIHGPNQSYNDIPMWNYSKLPESFGATEERVVSKIVRTENEFVSVMKEAQADPNRMYWIELVLAKEDAP KVLKKMGKLFAEQNKS |
| 23 | Treponema denticola | AAS11092.1 | MIVKPMVRNNICLNAHPQGCKKGVEDQIEYTKKRITAEVKAGAKAPKNVLVLGCSNGYGLASRITAAFGYGAAT IGVSFEKAGSETKYGTPGWYNNLAFDEAAKREGLYSVTIDGDAFSDEIKAQVIEEAKKKGJKFDLIVYSLASPVRTD PDTGIMHKSVLPKFGKTFGKTVDPFTGKTVDPTGELKEISAEPANDEEAAATVKVMGGEDWERWIKQLSKEGLLEEGCIT LAYSYIGPEATOALYRKGTIGKAKEHLEATAHRLNKENPSIRAFVSVNKGLVTRASAVIPVIPLYLASLFKVMKEKG NHEGCIEQITRLYAERLYRKDGTIPVDEENRIRIDDWELEEDVQKAVSALMEKVTGENAESLTDLAGYRHDFLAS NGFDVEGINYEAEVERFDRI |

FIGURE 6 (Continued)

| SEQ ID NO | Organism | GENBANK reference | Amino acid sequence |
|---|---|---|---|
| 24 | Euglena gracilis | AAW66853.1 | MSCPASPSAAVSAGALCLCVATVLLATGSNPTALSTASTRSPTSLVRGVDRGLMRPTTAAALLTMREVPQMA EGFSGEATSAWAAAGPQWAAPLVAASSALALWWWAARRSVRRPLAALAELPTAVTHLAPPMAMFTTAK VIQPKIRGFICTTTHPIGCEKRVQEEIAYARAHPPTSPGPKRVLVIGCSTGYGLSTRITAAFGYQAATLGVFLAGPP TKGRPAAAGWYNTVAFEKAALEAGLYARSLNGDAFDSTTKARTVEAIKRDLGTVDLVVYSIAAPKRTDPATGVL HKACLKPIGATYTNRTVNTDKAEVTDVSIEPASPEEIADTVKVMGGEDWELWIQALSEAGVLAEGAKTVAYSYI GPEMTWPVYWSGTIGEAKKDVEKAAKRITQQYGCPAYPVVAKALVTQASSAIPVVPLYICLLYRVMEKGTHE GCIEQMVRLLTKLYPENGAPIVDEAGRVRVDDWEMAEDVQQAVKDLWSQVSTANLKDISDFAGYQTEFLRL FGFGIDGVDYDQPVDVEADLPSAAQQ |
| 25 | Sphaerochaeta pleomorpha | AEV29304.1 | MIITKKVLRNVSLTAHPQGCAQYVQDQIDWVQAHAHASLDSRYQKCDDLKLPRRILVLGGSTGYGLSSRIVGAF GSGSDTINVSFEREPSQTKTATPGWYNTMAFEKRAKEAGLKAESIFGDAFSDETKQKTGALIKSLFGQVDLVIYSL ASPLRTDPKTGTTYRSVLKPLGKPFSALSVDMDCDVVKMATIEPAEGTQAEETVHVMGGEDWALWIEYLMQE NLLAEGAMTVSYSYIGPKITYPVYVREGTIGKAKEDLEKTAAELTKKLQQIQGKAYVSVNKALVTRASAVIPVVPLY MAILYQVMKERDLHEHCTEQIYRLFTEKLFSGKQIPTDDEGRVRVDDWEMQDDIQAEVERRWALQKEGEPLK DADIEGVRKEYDQJHGFGFDSIDYEKDVDPRDIY |
| 26 | Burkholderia mallei | AAU49089.1 | MIIKPRVRGFICV FIGURE 6 (Continued)

| SEQ ID NO | Organism | GENBANK reference | Amino acid sequence |
|---|---|---|---|
| 28 | Flavobacterium johnsoniae | ABQ06478.1 | MIIEPRMRGFICLTAHPAGCEQNVKNQJEYIKSKGAIAGAKKVLVIGASTGFGLASRITSAFGSDAATIGVFFEKPP VEGKTASPGWYNSAAFEKEAHKAGLYAKSINGDAFSNEIKRETLDLIKADLGQVDLVIYSLASPVRTNPNTGVTH RSVLKPIGQTFTNKTVDFHTGNVSEVSIAPANEEDIENTVAVMGGEDWAMWIDALKNENLLAEGATTIAYSYIG PELTEAVYRKGTIGRAKDHLEATAFTITDTLKSLGGKAYVSVNKALVTQASSAIPVIPLYISLLYKIMKEEGIHEGCIE QIQRLFQDRLYNGSEVPVDEKGRIRIDDWEMREDVQAKVAALWKEATTETLPSIGDLAGYRNDFLNLFGFEFA GVDYKADTNEVVNIESIK |

US 10,233,474 B2

MATERIALS AND METHODS FOR PRODUCING 6-CARBON MONOMERS

RELATED APPLICATIONS

This application claims priority from U.S. Provisional application Ser. No. 62/095,537, filed Dec. 22, 2014, the entire contents of which are incorporated by reference herein in their entirety.

FIELD OF THE INVENTION

This invention relates to methods for biosynthesizing 6-acetyloxy-3-oxohexanoyl-CoA using one or more polypeptides having alcohol O-acetyltransferase and a β-ketothiolase or synthase activity, and enzymatically converting 6-acetyloxy-3-oxohexanoyl-CoA to 6-hydroxyhexanoic acid using one or more polypeptides having 3-hydroxyacyl-CoA dehydrogenase, 3-oxoacyl-CoA reductase, enoyl-CoA hydratase, trans-2-enoyl-CoA reductase, esterase, CoA transferase, thioesterase activity, or using recombinant host cells expressing one or more of such enzymes. This invention also relates to methods for converting 6-hydroxyhexanoic acid to one or more of adipic acid, 6-aminohexanoic acid, hexamethylenediamine, caprolactam, and 1,6-hexanediol using one or more isolated enzymes such as dehydrogenases, reductases, hydratases, thioesterases, monooxygenases, and transaminases or using recombinant host cells expressing one or more such enzymes.

BACKGROUND

Nylons are polyamides that are generally synthesized by the condensation polymerization of a diamine with a dicarboxylic acid. Similarly, Nylons also may be produced by the condensation polymerization of lactams. A ubiquitous nylon is Nylon 6,6, which is produced by reaction of hexamethylenediamine (HMD) and adipic acid. Nylon 6 can be produced by a ring opening polymerization of caprolactam. Therefore, adipic acid, hexamethylenediamine and caprolactam are important intermediates in the production of Nylons (Anton & Baird, Polyamides Fibers, Encyclopedia of Polymer Science and Technology, 2001).

Industrially, adipic acid and caprolactam are produced via air oxidation of cyclohexane. The air oxidation of cyclohexane produces, in a series of steps, a mixture of cyclohexanone (K) and cyclohexanol (A), designated as KA oil. Nitric acid oxidation of KA oil produces adipic acid (Musser, Adipic acid, Ullmann's Encyclopedia of Industrial Chemistry, 2000). Caprolactam is produced from cyclohexanone via its oxime and subsequent acid rearrangement (Fuchs, Kieczka and Moran, Caprolactam, Ullmann's Encyclopedia of Industrial Chemistry, 2000)

Industrially, hexamethylenediamine (HMD) is produced by hydrocyanation of C6 building block to adiponitrile, followed by hydrogenation to HMD (Herzog and Smiley, Hexamethylenediamine, Ullmann's Encyclopedia of Industrial Chemistry, 2012).

Given a reliance on petrochemical feedstocks; biotechnology offers an alternative approach via biocatalysis. Biocatalysis is the use of biological catalysts, such as enzymes, to perform biochemical transformations of organic compounds.

Both bioderived feedstocks and petrochemical feedstocks are viable starting materials for the biocatalysis processes.

SUMMARY

Against the background, it is clear that there is a need for sustainable methods for producing one or more of adipic acid, caprolactam, 6-aminohexanoic acid, 6-hydroxyhexanoic acid, hexamethylenediamine, and 1,6-hexanediol, where the methods are biocatalyst based. This document is based at least in part on the discovery that it is possible to construct biochemical pathways for using, inter alia, an alcohol O-acetyltransferase and a β-ketothiolase or synthase to produce 6-hydroxyhexanoate, which can be converted in one or more enzymatic steps to adipic acid, 6-aminohexanoic acid, hexamethylenediamine, caprolactam, or 1,6-hexanediol. Adipic acid and adipate, 6-hydroxyhexanoic acid and 6-hydroxyhexanoate, and 6-aminohexanoic and 6-aminohexanoate are used interchangeably herein to refer to the compound in any of its neutral or ionized forms, including any salt forms thereof. It is understood by those skilled in the art that the specific form will depend on pH.

In the face of the optimality principle, it surprisingly has been discovered that appropriate non-natural pathways, feedstocks, host microorganisms, attenuation strategies to the host's biochemical network, and cultivation strategies may be combined to efficiently produce 6-hydroxyhexanoate as a C6 building block, or convert 6-hydroxyhexanoate to other C6 building blocks such as adipic acid, 6-aminohexanoic acid, hexamethylenediamine, caprolactam, or 1,6-hexanediol.

In some embodiments, a terminal carboxyl group can be enzymatically formed using a thioesterase, a CoA transferase, an esterase, an aldehyde dehydrogenase, a 6-oxohexanoate dehydrogenase, a 7-oxoheptanoate dehydrogenase, or a monooxgenase (e.g., in combination with an oxidoreductase and ferredoxin). See FIG. 1 and FIG. 2.

In some embodiments, a terminal amine group can be enzymatically formed using a ω-transaminase or a deacylase. See FIG. 4. The ω-transaminase can have at least 70% sequence identity to any one of the amino acid sequences set forth in SEQ ID NOs. 7-12.

In some embodiments, a terminal hydroxyl group can be enzymatically formed using an alcohol dehydrogenase. See FIG. 1 and FIG. 5.

In one aspect, this document features a method of producing 4-acetyloxybutyryl-CoA from 4-hydroxybutyrate in one or more enzymatic steps using an alcohol O-acetyltransferase. The alcohol O-acetyltransferase can have at least 70% sequence identity to the amino acid sequence set forth in SEQ ID NO: 17.

In one aspect, this document features a method of producing 6-acetyloxy-3-oxohexanoyl-CoA. The method includes enzymatically converting 4-acetyloxybutyryl-CoA to 6-acetyloxy-3-oxohexanoyl-CoA using a β-ketothiolase classified under EC. 2.3.1.- (e.g., EC 2.3.1.16 or EC 2.3.1.174). The β-ketothiolase can have at least 70% sequence identity to the amino acid sequence set forth in SEQ ID NO:1 or SEQ ID NO:16. The method can include enzymatically converting 6-acetyloxy-3-oxohexanoyl-CoA to 6-hydroxyhexanoate using a 3-hydroxyacyl-CoA dehydrogenase or a 3-oxoacyl-CoA reductase, an enoyl-CoA hydratase, a trans-2-enoyl-CoA reductase, an esterase, and a thioesterase or a CoA transferase. The 3-hydroxyacyl-CoA dehydrogenase or 3-oxoacyl-CoA reductase can be classified under EC 1.1.1.35, EC 1.1.1.36, EC 1.1.1.100, or EC 1.1.1.157. The enoyl-CoA hydratase can be classified under EC 4.2.1.17 or EC 4.2.1.119. The trans-2-enoyl-CoA reductase can be classified under EC 1.3.1.38, EC 1.3.1.44, or EC 1.3.1.8. The trans-2-enoyl-CoA reductase can have at least 70% sequence identity to the amino acid sequence set forth in SEQ ID NO: 23-28.

In one aspect, this document features a method for biosynthesizing 6-hydroxyhexanoate. The method includes enzymatically synthesizing 6-acetyloxy-3-oxohexanoyl-CoA from 4-acetyloxybutyryl-CoA using a β-ketothiolase or synthase classified under EC. 2.3.1.- (e.g., EC 2.3.1.16, EC 2.3.1.41, EC 2.3.1.174, EC 2.3.1.179, or EC 2.3.1.180) and enzymatically converting 6-acetyloxy-3-oxohexanoyl-CoA to 6-hydroxyhexanoate. The β-ketothiolase can have at least 70% sequence identity to the amino acid sequence set forth in SEQ ID NO:1 or SEQ ID NO:16. In some cases, 6-acetyloxy-3-oxohexanoyl-CoA can be converted to 6-acetyloxy-3-hydroxyhexanoyl-CoA using a 3-hydroxyacyl-CoA dehydrogenase or a 3-oxoacyl-CoA reductase, 6-acetyloxy-3-hydroxyhexanoyl-CoA can be converted to 6-acetyloxyhex-2-enoyl-CoA using an enoyl-CoA hydratase, 6-acetyloxyhex-2-enoyl-CoA can be converted to 6-acetyloxyhexanoyl-CoA using a trans-2-enoyl-CoA reductase, 6-acetyloxyhexanoyl-CoA can be converted to 6-acetyloxyhexanoic acid using a thioesterase or a CoA transferase, and 6-acetyloxyhexanoic acid can be converted to 6-hydroxyhexanoate using an esterase.

In some cases, 6-acetyloxy-3-oxohexanoyl-CoA can be converted to 6-acetyloxy-3-hydroxyhexanoyl-CoA using a 3-hydroxyacyl-CoA dehydrogenase or a 3-oxoacyl-CoA reductase, 6-acetyloxy-3-hydroxyhexanoyl-CoA can be converted to 6-acetyloxyhex-2-enoyl-CoA using an enoyl-CoA hydratase, 6-acetyloxyhex-2-enoyl-CoA can be converted to 6-acetyloxyhexanoyl-CoA using a trans-2-enoyl-CoA reductase, 6-acetyloxyhexanoyl-CoA can be converted to 6-hydroxyhexanoyl-CoA using an esterase, and 6-hydroxyhexanoyl-CoA can be converted to 6-hydroxyhexanoate using a thioesterase or a CoA transferase.

Any of the methods further can include enzymatically converting 6-hydroxyhexanoate to adipic acid, 6-aminohexanoate, caprolactam, hexamethylenediamine, or 1,6-hexanediol in one or more steps.

For example, 6-hydroxyhexanoate can be enzymatically converted to adipic acid using one or more of a monooxygenase, an alcohol dehydrogenase, a 4-hydroxybutanoate dehydrogenase, a 5-hydroxyvalerate dehydrogenase, a 6-hydroxyhexanoate dehydrogenase, a 7-oxoheptanoate dehydrogenase, a 6-oxohexanoate dehydrogenase, a 5-oxovalerate dehydrogenase, or an aldehyde dehydrogenase.

For example, 6-hydroxyhexanoate can be converted to 6-aminohexanoate using one or more of an alcohol dehydrogenase, a 6-hydroxyhexanoate dehydrogenase, a 5-hydroxypentanoate dehydrogenase, a 4-hydroxybutyrate dehydrogenase, and a ω-transaminase. The ω-transaminase can have at least 70% sequence identity to any one of the amino acid sequences set forth in SEQ ID NO. 7-12.

For example, 6-hydroxyhexanoate can be converted to caprolactam using one or more of an alcohol dehydrogenase, a 6-hydroxyhexanoate dehydrogenase, a 5-hydroxypentanoate dehydrogenase, a 4-hydroxybutyrate dehydrogenase, a ω-transaminase, and an amidohydrolase. The ω-transaminase can have at least 70% sequence identity to any one of the amino acid sequences set forth in SEQ ID NO. 7-12.

For example, 6-hydroxyhexanoate can be converted to hexamethylenediamine using one or more of a carboxylate reductase, a ω-transaminase, an alcohol dehydrogenase, an N-acetyltransferase, and an acetylputrescine deacylase. The co-transaminase can have at least 70% sequence identity to any one of the amino acid sequences set forth in SEQ ID NO. 7-12. The carboxylate reductase can have at least 70% sequence identity to any one of the amino acid sequences set forth in SEQ D NO. 2-6.

For example, 6-hydroxyhexanoate can be converted to 1,6-hexanediol using a carboxylate reductase and an alcohol dehydrogenase. The carboxylate reductase can have at least 70% sequence identity to any one of the amino acid sequences set forth in SEQ D NO. 2-6.

In any of the methods, 4-acetyloxybutyryl-CoA can be enzymatically produced from 2-oxoglutarate. For example, 4-acetyloxybutyryl-CoA can be enzymatically produced from 2-oxoglutarate using one or more of a glutamate synthase; a 2-oxoglutarate decarboxylase; a branch chain decarboxylase; a glutamate decarboxylase; a ω-transaminase; a CoA transferase, a CoA ligase, an acetyltransferase (e.g., an alcohol O-acetyltransferase) and an alcohol dehydrogenase.

In any of the methods described herein, adipic acid can be produced by forming the second terminal functional group in adipate semialdehyde (also known as 6-oxohexanoate) using (i) an aldehyde dehydrogenase classified under EC 1.2.1.3, (ii) a 6-oxohexanoate dehydrogenase classified under EC 1.2.1.63 such as that encoded by ChnE or a 7-oxoheptanoate dehydrogenase classified under EC 1.2.1.- (e.g., the gene product of ThnG) or iii) a monooxgenase in the cytochrome P450 family.

In any of the methods described herein, 6-aminohexanoic acid can be produced by forming the second terminal functional group in adipate semialdehyde using a co-transaminase classified under EC 2.61.18, EC 2.6.1.19, EC 2.6.1.29, EC 2.6.1.48, or EC 2.6.1.82.

In any of the methods described herein, caprolactam can be produced from 6-aminohexanoic acid using an amidohydrolase classified under EC 3.5.2.-. The amide bond associated with caprolactam is produced from a terminal carboxyl group and terminal amine group of 6-aminohexanoate.

In any of the methods described herein, hexamethylenediamine can be produced by forming a second terminal functional group in (i) 6-aminohexanal using a co-transaminase classified under EC 2.61.18, EC 2.6.1.19, EC 2.6.1.29, EC 2.6.1.48 or EC 2.6.1.82 or in (ii) N6-acetyl-1,6-diaminohexane using a deacylase classified, for example, under EC 3.5.1.17.

In any of the methods described herein, 1,6 hexanediol can be produced by forming the second terminal functional group in 6-hydroxyhexanal using an alcohol dehydrogenase classified under EC 1.1.1.- (e.g., EC 1.1.1.1, 1.1.1.2, 1.1.1.21, or 1.1.1.184) such as that encoded by YMR318C, YqhD or CAA81612.1.

In some embodiments, the biological feedstock can be or can derive from, monosaccharides, disaccharides, lignocellulose, hemicellulose, cellulose, lignin, levulinic acid and formic acid, triglycerides, glycerol, fatty acids, agricultural waste, condensed distillers' solubles, or municipal waste.

In some embodiments, the non-biological feedstock can be or can derive from natural gas, syngas, $CO_2/H_2$, methanol, ethanol, benzoate, non-volatile residue (NVR) or a caustic wash waste stream from cyclohexane oxidation processes, or terephthalic acid/isophthalic acid mixture waste streams.

In some embodiments, the host microorganism's tolerance to high concentrations of one or more C6 building blocks is improved through continuous cultivation in a selective environment.

In some embodiments, the host microorganism's biochemical network is attenuated or augmented to (1) ensure the intracellular availability of acetyl-CoA and 4-hydroxybutyryl-CoA, (2) create an NADH or NADPH imbalance that may only be balanced via the formation of one or more C6 building blocks, (3) prevent degradation of central metabolites, central precursors leading to and including C6 building blocks and (4) ensure efficient efflux from the cell.

In some embodiments, a cultivation strategy is used to achieve anaerobic, micro-aerobic, or aerobic cultivation conditions.

In some embodiments, the cultivation strategy includes limiting nutrients, such as limiting nitrogen, phosphate or oxygen.

In some embodiments, one or more C6 building blocks are produced by a single type of microorganism, e.g., a recombinant host containing one or more exogenous nucleic acids, using, for example, a fermentation strategy.

In another aspect, this document features a recombinant host that includes at least one exogenous nucleic acid encoding (i) an acetyltransferase (e.g., an alcohol O-acetyltransferase); (ii) a β-ketothiolase or synthase, (iii) a thioesterase or a CoA transferase, (v) an esterase and one or more of (vi) a 3-hydroxyacyl-CoA dehydrogenase or a 3-oxoacyl-CoA reductase, (vii) an enoyl-CoA hydratase, and (viii) a trans-2-enoyl-CoA reductase, the host producing 6-hydroxyhexanoate.

A host producing 6-hydroxyhexanoate further can include one or more of the following exogenous enzymes: a monooxygenase, an alcohol dehydrogenase, a 4-hydroxybutanoate dehydrogenase, a 5-hydroxyvalerate dehydrogenase, a 6-hydroxyhexanoate dehydrogenase, a 7-oxoheptanoate dehydrogenase, a 6-oxohexanoate dehydrogenase, a 5-oxovalerate dehydrogenase, or an aldehyde dehydrogenase, the host further producing adipic acid.

A host producing 6-hydroxyhexanoate further can include one or more of the following exogenous enzymes: a monooxygenase, a transaminase, a 6-hydroxyhexanoate dehydrogenase, a 5-hydroxypentanoate dehydrogenase, a 4-hydroxybutyrate dehydrogenase, and an alcohol dehydrogenase, the host further producing 6-aminohexanoate. Such a host further can include an exogenous amidohydrolase, the host further producing caprolactam.

A host producing 6-hydroxyhexanoate further can include one or more of the following exogenous enzymes: a carboxylate reductase, a ω-transaminase, a deacylase, a N-acetyl transferase, or an alcohol dehydrogenase, said host further producing hexamethylenediamine.

A host producing 6-hydroxyhexanoate further can include an exogenous carboxylate reductase and an exogenous alcohol dehydrogenase, the host further producing 1,6-hexanediol.

Any of the recombinant hosts described herein further can include one or more of the following exogenous enzymes: a glutamate synthase; a 2-oxoglutarate decarboxylase; a branch-chain decarboxylase; a glutamate decarboxylase; a ω-transaminase; a CoA-ligase; a CoA-transferase; an acetyltransferase, and an alcohol dehydrogenase.

Any of the recombinant hosts can be a prokaryote such as a prokaryote from a genus selected from the group consisting of *Escherichia; Clostridia; Corynebacteria; Cupriavidus; Pseudomonas; Delftia; Bacilluss; Lactobacillus; Lactococcus*; and *Rhodococcus*. For example, the prokaryote can be selected from the group consisting of *Escherichia coli, Clostridium ljungdahlii, Clostridium autoethanogenum, Clostridium kluyveri, Corynebacterium glutamicum, Cupriavidus necator, Cupriavidus metallidurans. Pseudomonas fluorescens, Pseudomonas putida, Pseudomonas oleavorans, Delftia acidovorans, Bacillus subtillis, Lactobacillus delbrueckii, Lactococcus lactis*, and *Rhodococcus equi*. Such prokaryotes also can be sources of genes for constructing recombinant host cells described herein that are capable of producing C6 building blocks.

Any of the recombinant hosts can be a eukaryote such as a eukaryote from a genus selected from the group consisting of *Aspergillus, Saccharomyces, Pichia, Yarrowia, Issatchenkia, Debaryomyces, Arxula*, and *Kluyveromyces*. For example, the eukaryote can be selected from the group consisting of *Aspergillus niger, Saccharomyces cerevisiae, Pichia pastoris, Yarrowia lipolytica, Issathenkia orientalis, Debaryomyces hansenii, Arxula adenoinivorans*, and *Kluyveromyces lactis*. Such eukaryotes also can be sources of genes for constructing recombinant host cells described herein that are capable of producing C6 building blocks.

Any of the recombinant hosts described herein further can include attenuation of one or more of the following enzymes: a polyhydroxyalkanoate synthase, an acetyl-CoA thioesterase, a phosphotransacetylase forming acetate, an acetate kinase, a lactate dehydrogenase, a menaquinol-fumarate oxidoreductase, an alcohol dehydrogenase forming ethanol, a triose phosphate isomerase, a pyruvate decarboxylase, a glucose-6-phosphate isomerase, NADH-consuming transhydrogenase, an NADH-specific glutamate dehydrogenase, a NADH/NADPH-utilizing glutamate dehydrogenase, a pimeloyl-CoA dehydrogenase; an acyl-CoA dehydrogenase accepting C6 building blocks and central precursors as substrates; a butyryl-CoA dehydrogenase; or an adipyl-CoA synthetase.

Any of the recombinant hosts described herein further can overexpress one or more genes encoding: an acetyl-CoA synthetase, a 6-phosphogluconate dehydrogenase; a transketolase; a puridine nucleotide transhydrogenase; a glyceraldehyde-3P-dehydrogenase; a malic enzyme; a glucose-6-phosphate dehydrogenase; a glucose dehydrogenase; a fructose 1,6 diphosphatase; a L-alanine dehydrogenase; a L-glutamate dehydrogenase; a formate dehydrogenase; a L-glutamine synthetase; a diamine transporter; a dicarboxylate transporter; and/or a multidrug transporter.

This document also features a biochemical network comprising a β-ketothiolase or synthase classified under EC. 2.3.1.-, 4-acetyloxybutyryl-CoA, and 6-acetyloxy-3-oxohexanoyl-CoA, wherein the β-ketothiolase or synthase enzymatically converts 4-acetyloxybutyryl-CoA to 6-acetyloxy-3-oxohexanoyl-CoA. The biochemical network further can include a 3-hydroxyacyl-CoA dehydrogenase or a 3-oxoacyl-CoA reductase, an enoyl-CoA hydratase, a trans-2-enoyl-CoA reductase, an esterase, and a thioesterase or a CoA transferase, wherein the 3-hydroxyacyl-CoA dehydrogenase or the 3-oxoacyl-CoA reductase, the enoyl-CoA hydratase, the trans-2-enoyl-CoA reductase, the esterase, and the thioesterase or the CoA transferase enzymatically convert 6-acetyloxy-3-oxohexanoyl-CoA to 6-hydroxyhexanoate.

This document also features a means for producing 6-acetyloxy-3-oxohexanoyl-CoA, wherein the means enzymatically convert 4-acetyloxybutyryl-CoA to 6-acetyloxy-3-oxohexanoyl-CoA. The means can include a β-ketothiolase or synthase classified under EC. 2.3.1.-. The means further can include means for enzymatically converting 6-acetyloxy-3-oxohexanoyl-CoA to 6-hydroxyhexanoate. The means can include a 3-hydroxyacyl-CoA dehydrogenase or a 3-oxoacyl-CoA reductase, an enoyl-CoA hydratase, a trans-2-enoyl-CoA reductase, an esterase, and a thioesterase or a CoA transferase.

This document also features a step for obtaining 6-acetyloxy-3-oxohexanoyl-CoA using a β-ketothiolase or synthase classified under EC. 2.3.1.-.

In another aspect, this document features a composition comprising 4-acetyloxybutyryl-CoA, bio 6-acetyloxy-3-oxohexanoyl-CoA, and a β-ketothiolase or synthase classified under EC. 2.3.1.-. The composition can be acellular or cellular.

In another aspect, this document features a composition comprising bio 6-acetyloxy-3-oxohexanoyl-CoA. The composition can be acellular or cellular.

In another aspect, this document features a bio 6-acetyloxy-3-oxohexanoyl-CoA produced by the method of enzymatically converting 4-acetyloxybutyryl-CoA to 6-acetyloxy-3-oxohexanoyl-CoA using a β-ketothiolase or synthase classified under EC. 2.3.1.-.

Many of the enzymes described herein catalyze reversible reactions, and the reaction of interest may be the reverse of the described reaction. The schematic pathways shown in FIGS. 1 to 5 illustrate the reaction of interest for each of the intermediates.

In one aspect, this document features a method for producing a bioderived six carbon compound. The method for producing a bioderived six carbon compound can include culturing or growing a recombinant host as described herein under conditions and for a sufficient period of time to produce the bioderived six carbon compound, wherein, optionally, the bioderived six carbon compound is selected from the group consisting of adipic acid, 6-aminohexanoic acid, hexamethylenediamine, caprolactam, or 1,6-hexanediol, and combinations thereof.

In one aspect, this document features composition comprising a bioderived six carbon compound as described herein and a compound other than the bioderived six carbon compound, wherein the bioderived six carbon compound is selected from the group consisting of adipic acid, 6-aminohexanoic acid, hexamethylenediamine, caprolactam, or 1,6-hexanediol, and combinations thereof. For example, the bioderived six carbon compound is a cellular portion of a host cell or an organism.

This document also features a biobased polymer comprising the bioderived adipic acid, 6-aminohexanoic acid, hexamethylenediamine, caprolactam, or 1,6-hexanediol, and combinations thereof.

This document also features a biobased resin comprising the bioderived adipic acid, 6-aminohexanoic acid, hexamethylenediamine, caprolactam, or 1,6-hexanediol, and combinations thereof, as well as a molded product obtained by molding a biobased resin.

In another aspect, this document features a process for producing a biobased polymer that includes chemically reacting the bioderived adipic acid, 6-aminohexanoic acid, hexamethylenediamine, caprolactam, or 1,6-hexanediol, with itself or another compound in a polymer producing reaction.

In another aspect, this document features a process for producing a biobased resin that includes chemically reacting the bioderived adipic acid, 6-aminohexanoic acid, hexamethylenediamine, caprolactam, or 1,6-hexanediol, with itself or another compound in a resin producing reaction.

Also, described herein is a means for obtaining adipic acid, 6-aminohexanoic acid, hexamethylenediamine, caprolactam, or 1,6-hexanediol using one or more polypeptides having β-ketothiolase, 3-hydroxyacyl-CoA dehydrogenase, 3-oxoacyl-CoA reductase, enoyl-CoA hydratase, trans-2-enoyl-CoA reductase, thioesterase or a CoA transferase, monooxygenase, alcohol dehydrogenase, 4-hydroxybutanoate dehydrogenase, 5-hydroxyvalerate dehydrogenase, 6-hydroxyhexanoate dehydrogenase, 7-oxoheptanoate dehydrogenase, 6-oxohexanoate dehydrogenase, 5-oxovalerate dehydrogenase, aldehyde dehydrogenase, ω-transaminase, amidohydrolase, co-transaminase or deacylase activity.

In another aspect, this document features a composition comprising one or more polypeptides having β-ketothiolase, 3-hydroxyacyl-CoA dehydrogenase, 3-oxoacyl-CoA reductase, enoyl-CoA hydratase, trans-2-enoyl-CoA reductase, thioesterase or a CoA transferase, monooxygenase, alcohol dehydrogenase, 4-hydroxybutanoate dehydrogenase, 5-hydroxyvalerate dehydrogenase, 6-hydroxyhexanoate dehydrogenase, 7-oxoheptanoate dehydrogenase, 6-oxohexanoate dehydrogenase, 5-oxovalerate dehydrogenase, aldehyde dehydrogenase, ω-transaminase, amidohydrolase, co-transaminase or deacylase activity and at least one of adipic acid, 6-aminohexanoic acid, hexamethylenediamine, caprolactam, or 1,6-hexanediol. The composition can be cellular.

In a another aspect, the disclosure provides a non-naturally occurring organism comprising at least one exogenous nucleic acid encoding at least one polypeptide having the activity of at least one enzyme depicted in any one of FIGS. 1 to 5.

In a another aspect, the disclosure provides a nucleic acid construct or expression vector comprising (a) (a) a polynucleotide encoding a polypeptide having the activity of a β-ketothiolase, wherein the polynucleotide is operably linked to one or more heterologous control sequences that direct production of the polypeptide and wherein the polypeptide having the activity of a β-ketothiolase is selected from the group consisting of a polypeptide having at least 70% sequence identity to the polypeptide of SEQ ID NO: 1 or SEQ ID NO: 16; or (b) a polynucleotide encoding a polypeptide having the activity of a trans-2-enoyl-CoA reductase, wherein the polynucleotide is operably linked to one or more heterologous control sequences that direct production of the polypeptide and wherein the polypeptide having the activity of a trans-2-enoyl-CoA reductase is selected from the group consisting of a polypeptide having at least 70% sequence identity to the polypeptide of SEQ ID NO: 23, SEQ ID NO: 24, SEQ ID NO: 25, SEQ ID NO: 26, SEQ ID NO: 27 or SEQ ID NO: 28; or (c) a polynucleotide encoding a polypeptide having the activity of ω-transaminase, wherein the polynucleotide is operably linked to one or more heterologous control sequences that direct production of the polypeptide and wherein the polypeptide having the activity of ω-transaminase is selected from the group consisting of a polypeptide having at least 70% sequence identity to the polypeptide of SEQ ID NO: 7, SEQ ID NO: 8, SEQ ID NO: 9, SEQ ID NO: 10, SEQ ID NO: 11, or SEQ ID NO: 12; or (d) a polynucleotide encoding a polypeptide having the activity of a phosphopantetheinyl transferase, wherein the polynucleotide is operably linked to one or more heterologous control sequences that direct production of the polypeptide and wherein the polypeptide having phosphopantetheinyl transferase is selected from the group consisting of a polypeptide having at least 70% sequence identity to the polypeptide of SEQ ID NO: 13 or 14; (e) a polynucleotide encoding a polypeptide having the activity of an alcohol-O-acetyltransferase, wherein the polynucleotide is operably linked to one or more heterologous control sequences that direct production of the polypeptide and wherein the polypeptide having the activity of an alcohol-O-acetyltransferase is selected from the group consisting of a polypeptide having at least 70% sequence identity to the polypeptide of SEQ ID NO: 17; (f) a polynucleotide encoding a polypeptide having the activity of a carboxylate reductase, wherein the polynucleotide is operably linked to one or more heterologous control sequences that direct production of the polypeptide and wherein the polypeptide having the activity of a carboxylate reductase is selected from the group consisting of a polypeptide having at least 70% sequence identity to the polypeptide of SEQ ID NO:2, SEQ ID NO: 3, SEQ ID NO: 4, SEQ ID NO: 5, or SEQ ID NO: 6; or (g) a polynucleotide encoding a polypeptide having the activity of a esterase, wherein the polynucleotide is operably linked to one or more heterologous control sequences that direct production of the polypeptide and wherein the polypeptide having the activity of a esterase is selected from the group consisting of a polypeptide having at least 70% sequence identity to the polypeptide of SEQ ID NO: 15; (h) a polynucleotide encoding a polypeptide having the activity of a pimeloyl-[acp] methyl ester esterase, wherein the polynucleotide is operably linked to one or more heterologous control sequences that direct production of the polypeptide and wherein the polypeptide having the activity of a pimeloyl-[acp] methyl ester esterase is selected from the group consisting of a polypeptide having at least 70% sequence identity to the polypeptide of SEQ ID NO: 18; or (i) a polynucleotide encoding a polypeptide having the activity of a CoA-transferase, wherein the polynucleotide is operably linked to one or more heterologous control sequences that direct production of the polypeptide and wherein the polypeptide having the activity of a CoA-transferase is selected from the group consisting of a polypeptide having at least 70% sequence identity to the polypeptide of SEQ ID NO: 19; or (j) a polynucleotide encoding a polypeptide having the activity of a decarboxylase, wherein the polynucleotide is operably linked to one or more heterologous control sequences that direct production of the polypeptide and wherein the polypeptide having the activity of a decarboxylase is selected from the group consisting of a polypeptide having at least 70% sequence identity to the polypeptide of SEQ ID NO: 20, SEQ ID NO: 21, or SEQ ID NO: 22. The disclosure further provides a composition comprising the nucleic acid construct or expression vector as recited above.

One of skill in the art understands that compounds containing carboxylic acid groups (including, but not limited to, organic monoacids, hydroxyacids, aminoacids, and dicarboxylic acids) are formed or converted to their ionic salt form when an acidic proton present in the parent compound either is replaced by a metal ion, e.g., an alkali metal ion, an alkaline earth ion, or an aluminum ion; or coordinates with an organic base. Acceptable organic bases include, but are not limited to, ethanolamine, diethanolamine, triethanolamine, tromethamine, N-methylglucamine, and the like. Acceptable inorganic bases include, but are not limited to, aluminum hydroxide, calcium hydroxide, potassium hydroxide, sodium carbonate, sodium hydroxide, and the like. A salt of the present invention is isolated as a salt or converted to the free acid by reducing the pH to below the pKa, through addition of acid or treatment with an acidic ion exchange resin.

One of skill in the art understands that compounds containing amine groups (including, but not limited to, organic amines, aminoacids, and diamines) are formed or converted to their ionic salt form, for example, by addition of an acidic proton to the amine to form the ammonium salt, formed with inorganic acids such as hydrochloric acid, hydrobromic acid, sulfuric acid, nitric acid, phosphoric acid, and the like; or formed with organic acids including, but not limited to, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. Acceptable inorganic bases include, but are not limited to, aluminum hydroxide, calcium hydroxide, potassium hydroxide, sodium carbonate, sodium hydroxide, and the like. A salt of the present invention is isolated as a salt or converted to the free amine by raising the pH to above the pKb through addition of base or treatment with a basic ion exchange resin.

One of skill in the art understands that compounds containing both amine groups and carboxylic acid groups (including, but not limited to, aminoacids) are formed or converted to their ionic salt form by either 1) acid addition salts, formed with inorganic acids including, but not limited to, hydrochloric acid, hydrobromic acid, sulfuric acid, nitric acid, phosphoric acid, and the like; or formed with organic acids including, but not limited to, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. Acceptable inorganic bases include, but are not limited to, aluminum hydroxide, calcium hydroxide, potassium hydroxide, sodium carbonate, sodium hydroxide, and the like, or 2) when an acidic proton present in the parent compound either is replaced by a metal ion, e.g., an alkali metal ion, an alkaline earth ion, or an aluminum ion; or coordinates with an organic base. Acceptable organic bases include, but are not limited to, ethanolamine, diethanolamine, triethanolamine, tromethamine, N-methylglucamine, and the like. Acceptable inorganic bases include, but are not limited to, aluminum hydroxide, calcium hydroxide, potassium hydroxide, sodium carbonate, sodium hydroxide, and the like. A salt can of the present invention is isolated as a salt or converted to the free acid by reducing the pH to below the pKa through addition of acid or treatment with an acidic ion exchange resin.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims. The word "comprising" in the claims may be replaced by "consisting essentially of" or with "consisting of," according to standard practice in patent law.

DESCRIPTION OF DRAWINGS

FIG. 6 contains the amino acid sequences of a *Cupriavidus necator* β-ketothiolase (see GenBank Accession No. AAC38322.1, SEQ ID NO: 1), a *Mycobacterium marinum* carboxylate reductase (see Genbank Accession No. ACC40567.1, SEQ ID NO: 2), a *Mycobacterium smegmatis* carboxylate reductase (see Genbank Accession No. ABK71854.1, SEQ ID NO: 3), a *Segniliparus rugosus* carboxylate reductase (see Genbank Accession No. EFV11917.1, SEQ ID NO: 4), a *Mycobacterium massiliense* carboxylate reductase (see Genbank Accession No. EIV11143.1, SEQ ID NO: 5), a *Segniliparus rotundus* carboxylate reductase (see Genbank Accession No. ADG98140.1, SEQ ID NO: 6), a *Chromobacterium violaceum* ω-transaminase (see Genbank Accession No. AAQ59697.1, SEQ ID NO: 7), a *Pseudomonas aeruginosa* ω-transaminase (see Genbank Accession No. AAG08191.1, SEQ ID NO: 8), a *Pseudomonas syringae* ω-transaminase (see Genbank Accession No. AAY39893.1, SEQ ID NO: 9), a *Rhodobacter sphaeroides* ω-transaminase (see Genbank Accession No. ABA81135.1, SEQ ID NO: 10), an *Escherichia coli* ω-transaminase (see Genbank Accession No. AAA57874.1, SEQ ID NO: 11), a *Vibrio fluvialis* ω-transaminase (See Genbank Accession No. AEA39183.1, SEQ ID NO: 12), a *Bacillus subtilis* phosphopantetheinyl transferase (see Genbank Accession No. CAA44858.1, SEQ ID NO: 13), a *Nocardia* sp. NRRL 5646 phosphopantetheinyl transferase (see Genbank Accession No. ABI83656.1, SEQ ID NO: 14), a *Pseudomonas fluorescens* carboxyl esterase (Genbank Accession No. AAB60168; SEQ ID NO: 15), an *Escherichia coli* β-ketothiolase (see GenBank Accession No. AAC74479.1, SEQ ID NO: 16), a *Saccharomyces cerevisiae* alcohol O-acetyltransferase (see Genbank Accession No. CAA85138.1, SEQ ID NO: 17), an *Escherichia coli* pimeloyl-[acp] methyl ester esterase (see Genbank Accession No. CAA33612.1, SEQ ID NO: 18), a *Clostridium aminobutyricum* 4-hydroxybutyrate CoA-transferase (see Genbank Accession No. CAB60036.2, SEQ ID NO: 19), a *Salmonella typhimurium* indolepyruvate decarboxylase (see Genbank Accession No. CAC48239.1, SEQ ID NO: 20), a *Mycobacterium smegmatis* 2-oxoglutarate decarboxylase (see Genbank Accession No ABK74238.1, SEQ ID NO: 21), a *Lactococcus lactis* subsp. *Lactis* α-ketoisovalerate decarboxylase (see Genbank Accession No ADA65057.1, SEQ ID NO: 22), a *Treponema denticola* enoyl-CoA reductase (see Genbank Accession No AAS11092.1, SEQ ID NO: 23), an *Euglena gracilis* enoyl-CoA reductase (see Genbank Accession No AAW66853.1, SEQ ID NO: 24), a *Sphaerochaeta pleomorpha* enoyl-CoA reductase (see Genbank Accession No AEV29304.1, SEQ ID NO: 25), a *Burkholderia mallei* enoyl-CoA reductase (see Genbank Accession No AAU49089.1, SEQ ID NO: 26), a *Xanthomonas oryzae* pv. *oryzae* enoyl-CoA reductase (see Genbank Accession No BAE66781.1, SEQ ID NO: 27) and a *Flavobacterium johnsoniae* enoyl-CoA reductase (see Genbank Accession No ABQ06478.1, SEQ ID NO: 28).

DETAILED DESCRIPTION

Figure 1:
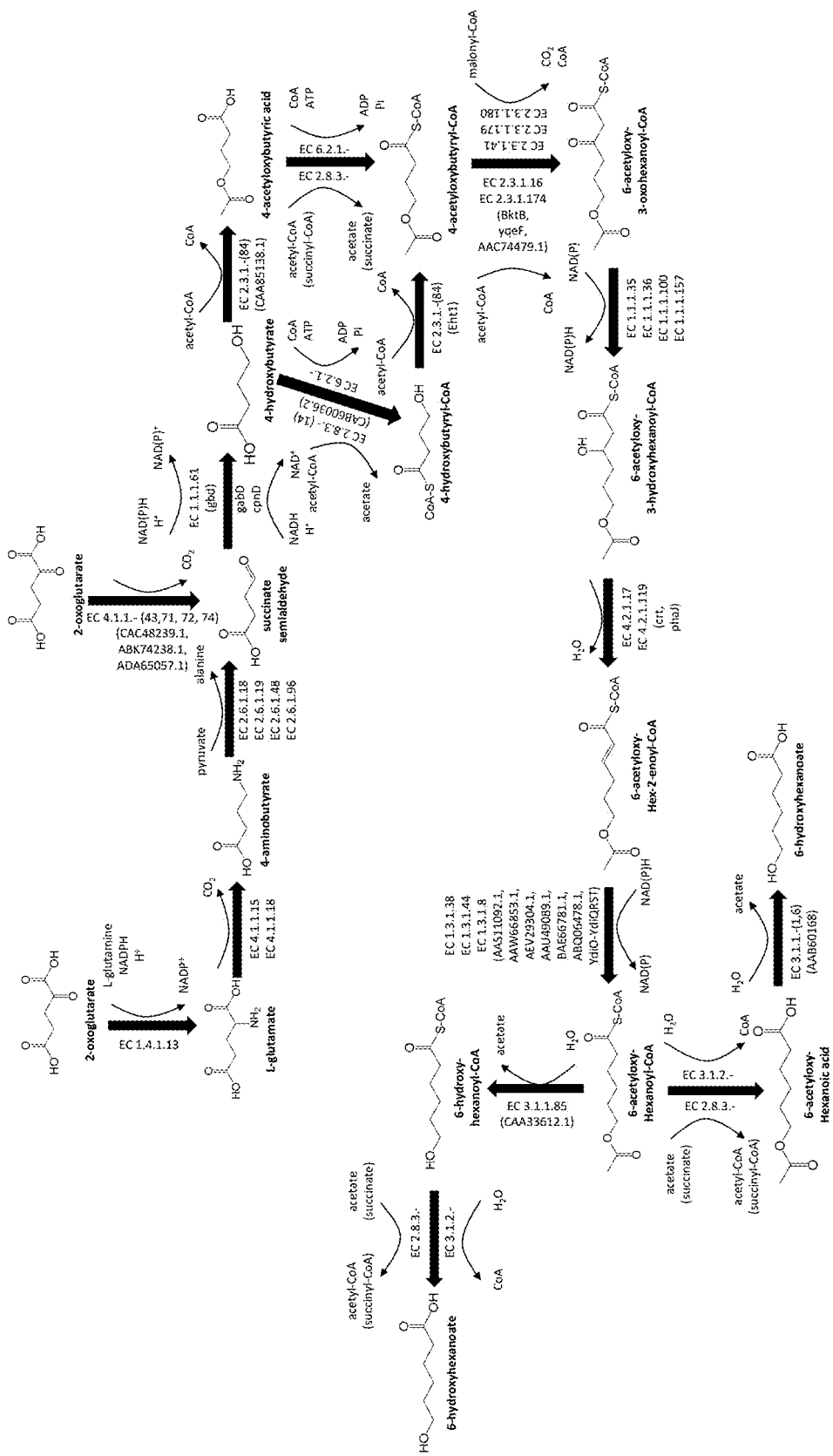
FIG. 1 is a schematic of exemplary biochemical pathways leading to 6-hydroxyhexanoate using 2-oxo-glutarate as a central metabolite.

In general, this document provides enzymes, non-natural pathways, cultivation strategies, feedstocks, host microorganisms and attenuations to the host's biochemical network, for producing 6-hydroxyhexanoate or one or more of adipic acid, caprolactam, 6-aminohexanoic acid, hexamethylenediamine or 1,6-hexanediol, all of which are referred to as C6 building blocks herein. As used herein, the term "central precursor" is used to denote any metabolite in any metabolic pathway shown herein leading to the synthesis of a C6 building block. The term "central metabolite" is used herein to denote a metabolite that is produced in all microorganisms to support growth.

Host microorganisms described herein can include endogenous pathways that can be manipulated such that 6-hydroxyhexanoate or one or more other C6 building blocks can be produced. In an endogenous pathway, the host microorganism naturally expresses all of the enzymes catalyzing the reactions within the pathway. A host microorganism containing an engineered pathway does not naturally express all of the enzymes catalyzing the reactions within the pathway but has been engineered such that all of the enzymes within the pathway are expressed in the host.

The term "exogenous" as used herein with reference to a nucleic acid (or a protein) and a host refers to a nucleic acid that does not occur in (and cannot be obtained from) a cell of that particular type as it is found in nature or a protein encoded by such a nucleic acid. Thus, a non-naturally-occurring nucleic acid is considered to be exogenous to a host once in the host. It is important to note that non-naturally-occurring nucleic acids can contain nucleic acid subsequences or fragments of nucleic acid sequences that are found in nature provided the nucleic acid as a whole does not exist in nature. For example, a nucleic acid molecule containing a genomic DNA sequence within an expression vector is non-naturally-occurring nucleic acid, and thus is exogenous to a host cell once introduced into the host, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid. A nucleic acid that is naturally-occurring can be exogenous to a particular host microorganism. For example, an entire chromosome isolated from a cell of yeast x is an exogenous nucleic acid with respect to a cell of yeast y once that chromosome is introduced into a cell of yeast y.

In contrast, the term "endogenous" as used herein with reference to a nucleic acid (e.g., a gene) (or a protein) and a host refers to a nucleic acid (or protein) that does occur in (and can be obtained from) that particular host as it is found in nature. Moreover, a cell "endogenously expressing" a nucleic acid (or protein) expresses that nucleic acid (or protein) as does a host of the same particular type as it is found in nature. Moreover, a host "endogenously producing" or that "endogenously produces" a nucleic acid, protein, or other compound produces that nucleic acid, protein, or compound as does a host of the same particular type as it is found in nature.

For example, depending on the host and the compounds produced by the host, one or more of the following enzymes may be expressed in the host in addition to a β-ketothiolase or synthase: a 3-hydroxyacyl-CoA dehydrogenase, a 3-oxoacyl-CoA reductase, an enoyl-CoA hydratase, a trans-2-enoyl-CoA reductase, a thioesterase, a CoA transferase, an aldehyde dehydrogenase, a monooxygenase, an alcohol dehydrogenase, a 6-oxohexanoate dehydrogenase, a 7-oxoheptanoate dehydrogenase, a co transaminase, a 6-hydroxyhexanoate dehydrogenase, a 5-hydroxypentanoate dehydrogenase, a 4-hydroxybutyrate dehydrogenase, a carboxylate reductase, a deacylase, an N-acetyl transferase, a ω-transaminase, an amidohydrolase, a glutamate synthase; a 2-oxoglutarate decarboxylase, a branch-chain decarboxylase, a glutamate decarboxylase, an esterase, or an alcohol O-acetyltransferase. In recombinant hosts expressing a carboxylate reductase, a phosphopantetheinyl transferase also can be expressed as it enhances activity of the carboxylate reductase. In recombinant hosts expressing a monooxygenase, an electron transfer chain protein such as an oxidoreductase or ferredoxin polypeptide also can be expressed.

For example, a recombinant host can include an exogenous alcohol O-acetyltransferase and produce 4-acetyloxybutyric acid or 4-acetyloxybutyryl-CoA, either of which can be converted to 6-hydroxyhexanoate.

For example, a recombinant host can include an exogenous β-ketothiolase or synthase and produce 6-acetyloxy-3-oxohexanoyl-CoA, which can be converted to 6-hydroxyhexanoate.

For example, a recombinant host can include an exogenous alcohol O-acetyltransferase and an exogenous β-ketothiolase or synthase and produce 6-acetyloxy-3-oxohexanoyl-CoA, which can be converted to 6-hydroxyhexanoate.

For example, a recombinant host can include an exogenous alcohol O-acetyltransferase, an exogenous CoA-ligase or an exogenous CoA-transferase, and an exogenous β-ketothiolase or synthase and produce 6-acetyloxy-3-oxohexanoyl-CoA, which can be converted to 6-hydroxyhexanoate.

For example, a recombinant host can include an exogenous alcohol O-acetyltransferase, an exogenous CoA-ligase or an exogenous CoA-transferase, and an exogenous β-ketothiolase or synthase, and one or more of the following exogenous enzymes: 3-hydroxyacyl-CoA dehydrogenase or a 3-oxoacyl-CoA reductase, an enoyl-CoA hydratase, a trans-2-enoyl-CoA reductase, an exogenous thioesterase or an exogenous CoA transferase, and an esterase, and produce 6-hydroxyhexanoate. It will be appreciated that an exogenous CoA transferase or an exogenous CoA ligase can be used to convert 4-hydroxybutyrate to 4-hydroxybutyryl-CoA or 4-acetyloxybutyric acid to 4-acetyloxybutyryl-CoA, and that an exogenous CoA transferase or a thioesterase can be used to convert 6-hydroxyhexanoyl-CoA to 6-hydroxyhexanoate, or 6-acetyloxy-hexanoyl-CoA to 6-acetyloxyhexanoic acid. Accordingly, it will be appreciated that a host may comprise a single type of exogenous CoA transferase or there may be two or more exogenous CoA transferases.

For example, a recombinant host can include an exogenous alcohol O-acetyltransferase, an exogenous CoA-ligase or an exogenous CoA-transferase, an exogenous β-ketothiolase or synthase, an exogenous thioesterase or CoA-transferase, an enoyl-CoA hydratase, an exogenous trans-2-enoyl-CoA reductase, an exogenous 3-hydroxyacyl-CoA dehydrogenase or an exogenous 3-oxoacyl-CoA reductase, and an exogenous esterase, and produce 6-hydroxyhexanoate.

For example, a recombinant host producing 6-hydroxyhexanoate can include one or more of the following exogenous enzymes: a monooxygenase, an alcohol dehydrogenase, a 4-hydroxybutyrate dehydrogenase, a 5-hydroxypentanoate dehydrogenase, a 6-hydroxyhexanoate dehydrogenase, a 7-oxoheptanoate dehydrogenase, a 5-oxovalerate dehydrogenase, a 6-oxohexanoate dehydrogenase, or an aldehyde dehydrogenase, and further produce adipic acid. For example, a recombinant host producing 6-hydroxyhexanoate can include an exogenous monooxygenase and produce adipic acid. For example, a recombinant host producing 6-hydroxyhexanoate can include an exogenous 6-hydroxyhexanoate dehydrogenase and an aldehyde dehydrogenase and produce adipic acid. For example, a recombinant host producing 6-hydroxyhexanoate can include an exogenous alcohol dehydrogenase and one of the following exogenous enzymes: a 5-oxovalerate dehydrogenase, a 6-oxohexanoate dehydrogenase, or a 7-oxoheptanoate dehydrogenase, and produce adipic acid.

For example, a recombinant host producing 6-hydroxyhexanoate can include one or more of the following exogenous enzymes: an alcohol dehydrogenase, a 6-hydroxyhexanoate dehydrogenase, or a transaminase, and further produce 6-aminohexanoate. For example, a recombinant host producing 6-hydroxyhexanoate can include an exogenous alcohol dehydrogenase and an exogenous transaminase and produce 6-aminohexanoate. For example, a recombinant host producing 6-hydroxyhexanoate can include an exogenous 6-hydroxyhexanoate dehydrogenase and an exogenous transaminase and produce 6-aminohexanoate. Any of such hosts further can include an exogenous amidohydrolase and further produce caprolactam.

For example, a recombinant host producing 6-hydroxyhexanoate can include one or more of the following exogenous enzymes: a carboxylate reductase, a ω-transaminase, a deacylase, an N-acetyl transferase, or an alcohol dehydrogenase, and produce hexamethylenediamine. For example, a recombinant host producing 6-hydroxyhexanoate can include an exogenous carboxylate reductase, an exogenous alcohol dehydrogenase, and one or more exogenous transaminases (e.g., one transaminase or two different transaminases), and produce hexamethylenediamine. For example, a recombinant host producing 6-hydroxyhexanoate can include an exogenous carboxylate reductase and one or more exogenous transaminases (e.g., one transaminase or two different transaminases) and produce hexamethylenediamine. For example, a recombinant host producing 6-hydroxyhexanoate can include an exogenous alcohol dehydrogenase, an exogenous carboxylate reductase, and one or more exogenous transaminases (e.g., one transaminase, or two or three different transaminases) and produce hexamethylenediamine. For example, a recombinant host producing 6-hydroxyhexanoate can include an exogenous alcohol dehydrogenase, an exogenous N-acetyl transferase, a carboxylate reductase, a deacylase, and one or more exogenous transaminases (e.g., one transaminase or two different transaminases) and produce hexamethylenediamine.

For example, a recombinant host producing 6-hydroxyhexanoate can include one or more of the following exogenous enzymes: a carboxylate reductase and an alcohol dehydrogenase, and further produce 1,6-hexanediol.

In any of the recombinant hosts, the recombinant host also can include one or more (e.g., one, two, three, or four or more) of the following exogenous enzymes used to convert 2-oxoglutarate to 4-hydroxybutyryl-CoA: a glutamate synthase; a 2-oxoglutarate decarboxylase; a branch-chain decarboxylase; a glutamate decarboxylase; a CoA-ligase; a CoA-transferase; a ω-transaminase; a phenylpyruvate decarboxylase, an indolepyruvate decarboxylase, and a dehydrogenase. For example, a recombinant host can include an exogenous glutamate synthase, a glutamate decarboxylase; a CoA-ligase or a CoA-transferase; a ω-transaminase; and a dehydrogenase. For example, a recombinant host can include an exogenous 2-oxoglutarate decarboxylase, a branch-chain decarboxylase, a phenylpyruvate decarboxylase, or an indolepyruvate decarboxylase; an exogenous CoA-ligase or an exogenous CoA-transferase; and an exogenous dehydrogenase.

Within an engineered pathway, the enzymes can be from a single source, i.e., from one species or genera, or can be from multiple sources, i.e., different species or genera. Nucleic acids encoding the enzymes described herein have been identified from various organisms and are readily available in publicly available databases such as GenBank or EMBL.

As used herein, references to a particular enzyme (e.g. β-ketothiolase) means a polypeptide having the activity of the particular enzyme (e.g. a polypeptide a β-ketothiolase activity).

Any of the enzymes described herein that can be used for production of one or more C6 building blocks can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of the corresponding wild-type enzyme. It will be appreciated that the sequence identity can be determined on the basis of the mature enzyme (e.g., with any signal sequence removed) or on the basis of the immature enzyme (e.g., with any signal sequence included). It also will be appreciated that the initial methionine residue may or may not be present on any of the enzyme sequences described herein.

For example, a β-ketothiolase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Cupriavidus necator* (see GenBank Accession No. AAC38322.1, SEQ ID NO: 1) or an *Escherichia coli* (see GenBank Accession No. AAC74479.1, SEQ ID NO: 16) β-ketothiolase. See FIG. 6.

For example, a carboxylate reductase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Mycobacterium marinum* (see Genbank Accession No. ACC40567.1, SEQ ID NO: 2), a *Mycobacterium smegmatis* (see Genbank Accession No. ABK71854.1, SEQ ID NO: 3), a *Segniliparus rugosus* (see Genbank Accession No. EFV11917.1, SEQ ID NO: 4), a *Mycobacterium massiliense* (see Genbank Accession No. EIV11143.1, SEQ ID NO: 5), or a *Segniliparus rotundus* (see Genbank Accession No. ADG98140.1, SEQ ID NO: 6) carboxylate reductase. See, FIG. 6.

For example, a ω-transaminase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Chromobacterium violaceum* (see Genbank Accession No. AAQ59697.1, SEQ ID NO: 7), a *Pseudomonas aeruginosa* (see Genbank Accession No. AAG08191.1, SEQ ID NO: 8), a *Pseudomonas syringae* (see Genbank Accession No. AAY39893.1, SEQ ID NO: 9), a *Rhodobacter sphaeroides* (see Genbank Accession No. ABA81135.1, SEQ ID NO: 10), an *Escherichia coli* (see Genbank Accession No. AAA57874.1, SEQ ID NO: 11), or a *Vibrio fluvialis* (see Genbank Accession No. AEA39183.1, SEQ ID NO: 12)

ω-transaminase. Some of these ω-transaminases are diamine ω-transaminases. See, FIG. 6.

For example, a phosphopantetheinyl transferase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Bacillus subtilis* phosphopantetheinyl transferase (see Genbank Accession No. CAA44858.1, SEQ ID NO: 13) or a *Nocardia* sp. NRRL 5646 phosphopantetheinyl transferase (see Genbank Accession No. ABI83656.1, SEQ ID NO: 14). See, FIG. 6.

For example, an esterase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Pseudomonas fluorescens* carboxyl esterase (Genbank Accession No. AAB60168; SEQ ID NO: 15). See, FIG. 6.

For example, an alcohol O-acetyltransferase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Saccharomyces cerevisiae* alcohol O-acetyltransferase (Genbank Accession No. CAA85138.1; SEQ ID NO: 17). See, FIG. 6.

For example, a pimeloyl-[acp] methyl ester esterase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of an *Escherichia coli* pimeloyl-[acp] methyl ester esterase (see Genbank Accession No. CAA33612.1, SEQ ID NO: 18). See. FIG. 6.

For example, a CoA-transferase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Clostridium aminobutyricum* 4-hydroxybutyrate CoA-transferase (see Genbank Accession No. CAB60036.2, SEQ ID NO: 19). See. FIG. 6.

For example, a decarboxylase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Salmonella typhimurium* (see Genbank Accession No. CAC48239.1, SEQ ID NO: 20), a *Mycobacterium smegmatis* (see Genbank Accession No ABK74238.1, SEQ ID NO: 21), or a *Lactococcus lactis* subsp. *Lactis* decarboxylase (see Genbank Accession No ADA65057.1, SEQ ID NO: 22). See, FIG. 6.

For example, an enoyl-CoA reductase described herein can have at least 70% sequence identity (homology) (e.g., at least 75%, 80%, 85%, 90%, 91%, 92%, 93%, 94%, 95%, 96%, 97%, 98%, 99%, or 100%) to the amino acid sequence of a *Treponema denticola* (see Genbank Accession No AAS11092.1, SEQ ID NO: 23), an *Euglena gracilis* (see Genbank Accession No AAW66853.1, SEQ ID NO: 24), a *Sphaerochaeta pleomorpha* (see Genbank Accession No AEV29304.1, SEQ ID NO: 25), a *Burkholderia mallei* (see Genbank Accession No AAU49089.1, SEQ ID NO: 26), a *Xanthomonas oryzae* pv. *oryzae* (see Genbank Accession No BAE66781.1, SEQ ID NO: 27) and a *Flavobacterium johnsoniae* enoyl-CoA reductase (see Genbank Accession No ABQ06478.1, SEQ ID NO: 28). See, FIG. 6.

The percent identity (homology) between two amino acid sequences can be determined as follows. First, the amino acid sequences are aligned using the BLAST 2 Sequences (B12seq) program from the stand-alone version of BLASTZ containing BLASTP version 2.0.14. This stand-alone version of BLASTZ can be obtained from Fish & Richardson's web site (e.g., www.fr.com/blast/) or the U.S. government's National Center for Biotechnology Information web site (www.ncbi.nlm.nih.gov). Instructions explaining how to use the B12seq program can be found in the readme file accompanying BLASTZ. B12seq performs a comparison between two amino acid sequences using the BLASTP algorithm. To compare two amino acid sequences, the options of B12seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\B12seq -i c:\seq1.txt -j c:\seq2.txt -p blastp -o c:\output.txt. If the two compared sequences share homology (identity), then the designated output file will present those regions of homology as aligned sequences. If the two compared sequences do not share homology (identity), then the designated output file will not present aligned sequences. Similar procedures can be following for nucleic acid sequences except that blastn is used.

Once aligned, the number of matches is determined by counting the number of positions where an identical amino acid residue is presented in both sequences. The percent identity (homology) is determined by dividing the number of matches by the length of the full-length polypeptide amino acid sequence followed by multiplying the resulting value by 100. It is noted that the percent identity (homology) value is rounded to the nearest tenth. For example, 78.11, 78.12, 78.13, and 78.14 is rounded down to 78.1, while 78.15, 78.16, 78.17, 78.18, and 78.19 is rounded up to 78.2. It also is noted that the length value will always be an integer.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given enzyme can be modified such that optimal expression in a particular species (e.g., bacteria or fungus) is obtained, using appropriate codon bias tables for that species.

Functional fragments of any of the enzymes described herein can also be used in the methods of the document. The term "functional fragment" as used herein refers to a peptide fragment of a protein that has at least 25% (e.g., at least: 30%; 40%; 50%; 60%; 70%; 75%; 80%; 85%; 90%; 95%; 98%; 99%; 100%; or even greater than 100%) of the activity of the corresponding mature, full-length, wild-type protein. The functional fragment can generally, but not always, be comprised of a continuous region of the protein, wherein the region has functional activity.

This document also provides (i) functional variants of the enzymes used in the methods of the document and (ii) functional variants of the functional fragments described above. Functional variants of the enzymes and functional fragments can contain additions, deletions, or substitutions relative to the corresponding wild-type sequences. Enzymes with substitutions will generally have not more than 50 (e.g., not more than one, two, three, four, five, six, seven, eight, nine, ten, 12, 15, 20, 25, 30, 35, 40, or 50) amino acid substitutions (e.g., conservative substitutions). This applies to any of the enzymes described herein and functional fragments. A conservative substitution is a substitution of one amino acid for another with similar characteristics.

Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The nonpolar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic or acidic groups by another member of the same group can be deemed a conservative substitution. By contrast, a nonconservative substitution is a substitution of one amino acid for another with dissimilar characteristics.

Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids. Additions (addition variants) include fusion proteins containing: (a) any of the enzymes described herein or a fragment thereof; and (b) internal or terminal (C or N) irrelevant or heterologous amino acid sequences. In the context of such fusion proteins, the term "heterologous amino acid sequences" refers to an amino acid sequence other than (a). A heterologous sequence can be, for example a sequence used for purification of the recombinant protein (e.g., FLAG, polyhistidine (e.g., hexahistidine), hemagglutinin (HA), glutathione-S-transferase (GST), or maltose binding protein (MBP)). Heterologous sequences also can be proteins useful as detectable markers, for example, luciferase, green fluorescent protein (GFP), or chloramphenicol acetyl transferase (CAT). In some embodiments, the fusion protein contains a signal sequence from another protein. In certain host cells (e.g., yeast host cells), expression and/or secretion of the target protein can be increased through use of a heterologous signal sequence. In some embodiments, the fusion protein can contain a carrier (e.g., KLH) useful, e.g., in eliciting an immune response for antibody generation) or ER or Golgi apparatus retention signals. Heterologous sequences can be of varying length and in some cases can be a longer sequences than the full-length target proteins to which the heterologous sequences are attached.

Engineered hosts can naturally express none or some (e.g., one or more, two or more, three or more, four or more, five or more, or six or more) of the enzymes of the pathways described herein. Thus, a pathway within an engineered host can include all exogenous enzymes, or can include both endogenous and exogenous enzymes. Endogenous genes of the engineered hosts also can be disrupted to prevent the formation of undesirable metabolites or prevent the loss of intermediates in the pathway through other enzymes acting on such intermediates. Engineered hosts can be referred to as recombinant hosts or recombinant host cells. As described herein recombinant hosts can include nucleic acids encoding one or more of a β-ketothiolase, an esterase, an O-acetyl-transferase, a CoA transferase, a CoA ligase, a dehydrogenase, a synthase, a decarboxylase, a reductase, a hydratase, a thioesterase, a monooxygenase, a thioesterase, amidohydrolase, and transaminase as described herein.

In addition, the production of C6 building blocks can be performed in vitro using the isolated enzymes described herein, using a lysate (e.g., a cell lysate) from a host microorganism as a source of the enzymes, or using a plurality of lysates from different host microorganisms as the source of the enzymes.

The reactions of the pathways described herein can be performed in one or more host strains (a) naturally expressing one or more relevant enzymes, (b) genetically engineered to express one or more relevant enzymes, or (c) naturally expressing one or more relevant enzymes and genetically engineered to express one or more relevant enzymes. Alternatively, relevant enzymes can be extracted from of the above types of host cells and used in a purified or semi-purified form. Moreover, such extracts include lysates (e.g. cell lysates) that can be used as sources of relevant enzymes. In the methods provided by the document, all the steps can be performed in host cells, all the steps can be performed using extracted enzymes, or some of the steps can be performed in cells and others can be performed using extracted enzymes.

Enzymes Generating 6-Hydroxyhexanoate

As depicted in FIG. 1, 6-hydroxyhexanaote can be biosynthesized from 2-oxoglutarate through the intermediate 6-acetyloxy-3-oxohexanoyl-CoA, which can be produced from 4-acetyloxybutyryl-CoA using a β-ketothiolase or synthase. 4-acetyloxybutyryl-CoA can be produced from 4-hydroxybutyryl-CoA using an alcohol O-acetyltransferase or produced from 4-hydroxybutyrate using an alcohol O-acetyltransferase and either a CoA-ligase classified under, for example, EC 6.2.1- (e.g., EC 6.2.1.40) or a CoA-transferase classified under, for example, EC 2.8.3.-. 6-acetyloxy-3-oxohexanoyl-CoA can be converted to 6-hydroxyhexanoate using a 3-hydroxyacyl-CoA dehydrogenase, 3-oxoacyl-CoA dehydrogenase, acetoacetyl-CoA reductase, or 3-oxoacyl-CoA reductase; an enoyl-CoA hydratase; a trans-2-enoyl-CoA reductase; an esterase; and a thioesterase or a CoA transferase.

In some embodiments, a β-ketothiolase or synthase can be classified under EC 2.3.1.- such as 2.3.1.16, EC 2.3.1.41, EC 2.3.1.174, EC 2.3.1.179, or EC 2.3.1.180. For example, a β-ketothiolase may be classified under EC 2.3.1.16, such as the gene product of bktB or yqeF or may be classified under EC 2.3.1.174 such as the gene product of paaJ. The β-ketothiolase encoded by bktB from *Cupriavidus necator* accepts acetyl-CoA and butanoyl-CoA as substrates, forming a CoA-activated C6 aliphatic backbone (see, e.g., Haywood et al., *FEMS Microbiology Letters*, 1988, 52:91-96; Slater et al., *J. Bacteriol.*, 1998, 180(8):1979-1987). The β-ketothiolase encoded by yqeF accepts long chain substrates (Dellomonaco et al., *Nature*, 2011, 476, 355). The β-ketothiolase encoded by paaJ from *Escherichia coli* accepts succinyl-CoA and acetyl-CoA as substrates, forming a CoA-activated backbone (Nogales et al., *Microbiology*, 2007, 153, 357-365). See, for example, SEQ ID NO: 1 and SEQ ID NO: 16 in FIG. 6.

In some embodiments, an alcohol O-acetyltransferase can be classified under EC 2.3.1.-. For example, an alcohol O-acetyltransferase can be classified under EC 2.3.1.84 such as the gene product of Eht1 (SEQ ID NO: 17).

In some embodiments, a 3-hydroxyacyl-CoA dehydrogenase or 3-oxoacyl-CoA dehydrogenase can be classified under EC 1.1.1.-. For example, the 3-hydroxyacyl-CoA dehydrogenase can be classified under EC 1.1.1.35, such as the gene product of fadB; classified under EC 1.1.1.157, such as the gene product of hbd (also can be referred to as a 3-hydroxybutyryl-CoA dehydrogenase); or classified under EC 1.1.1.36, such as the acetoacetyl-CoA reductase gene product of phaB (Liu & Chen, Appl. Microbiol. Biotechnol., 2007, 76(5):1153-1159; Shen et al., *Appl. Environ.*

Microbiol., 2011, 77(9):2905-2915; Budde et al., *J. Bacteriol.*, 2010, 192(20):5319-5328).

In some embodiments, a 3-oxoacyl-CoA reductase can be classified under EC 1.1.1.100, such as the gene product of fabG (Budde et al., *J. Bacteriol.*, 2010, 192(20):5319-5328; Nomura et al., *Appl. Environ. Microbiol.*, 2005, 71(8):4297-4306).

In some embodiments, an enoyl-CoA hydratase can be classified under EC 4.2.1.17, such as the gene product of crt, or classified under EC 4.2.1.119, such as the gene product of phaJ (Shen et al., 2011, supra; Fukui et al., *J. Bacteriol.*, 1998, 180(3):667-673).

In some embodiments, a trans-2-enoyl-CoA reductase can be classified under EC 1.3.1.38 or EC 1.3.1.44, such as the gene product of Egter (SEQ ID NO: 24) (Nishimaki et al., *J. Biochem.*, 1984, 95:1315-1321; Shen et al., 2011, supra) or tdter (SEQ ID NO: 25) (Bond-Watts et al., *Biochemistry*, 2012, 51:6827-6837), YdiO-YdiQRST (Dellomonaco et al., *Nature*, 2011, 476, 355), or EC 1.3.1.8 (Inui et al., *Eur. J. Biochem.*, 1984, 142, 121-126). Similarly, an enoyl-CoA reductase can be encoded by SEQ ID NO: 25-28.

In some embodiments, the terminal carboxyl group leading to the synthesis of 6-hydroxyhexanoate is enzymatically formed in 6-hydroxyhexanoyl-CoA by a thioesterase classified under EC 3.1.2.-, resulting in the production of 6-hydroxyhexanoate. The thioesterase can be the gene product of YciA or Acot13 (Cantu et al., *Protein Science*, 2010, 19, 1281-1295; Zhuang et al., *Biochemistry*, 2008, 47(9): 2789-2796; Naggert et al., *J. Biol. Chem.*, 1991, 266(17): 11044-11050).

In some embodiments, the terminal carboxyl group leading to the synthesis of 6-hydroxyhexanoate is enzymatically formed in 6-hydroxyhexanoyl-CoA by a CoA-transferase classified under, for example, EC 2.8.3- such as the gene product of cat2 from *Clostridium kluyveri*, abfT (SEQ ID NO: 19) from *Clostridium aminobutyricum* or the 5-hydroxypentanoate CoA-transferase from *Clostridium viride*.

In some embodiments, the terminal carboxyl group leading to the synthesis of 6-hydroxyhexanoate is enzymatically formed in 6-acetyloxy-hexanoic acid by an esterase classified, for example, under EC 3.1.1.1- such as a carboxyl esterase classified under EC 3.1.1.1 (e.g., the gene product of EstC) or an acetylesterase classified under EC 3.1.1.6. For example, an esterase can be the gene product of estC from *Burkholderia gladioli* or from *Pseudomonas fluorescens* (SEQ ID NO: 15). See FIG. 1, and FIG. 6.

Figure 2:
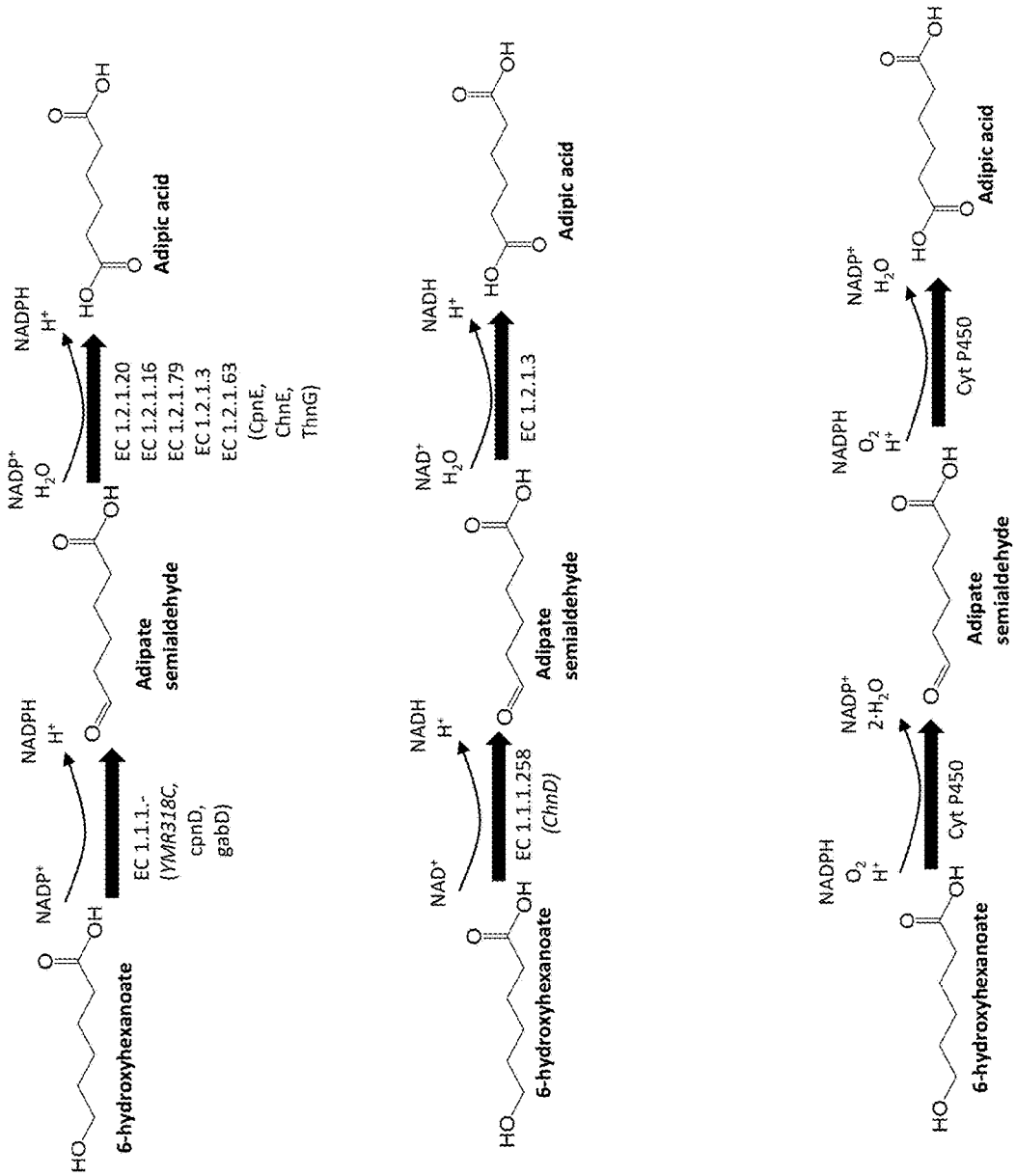
FIG. 2 is a schematic of exemplary biochemical pathways leading to adipic acid using 6-hydroxyhexanoate as a central precursor.

Enzymes Generating the Terminal Carboxyl Groups in the Biosynthesis of Adipic Acid As depicted in FIG. 2, the terminal carboxyl group leading to the production of adipic acid can be enzymatically formed using an aldehyde dehydrogenase, a 5-oxovalerate dehydrogenase, a 6-oxohexanoate dehydrogenase, a 7-oxoheptanoate dehydrogenase, or a monooxygenase.

In some embodiments, the second terminal carboxyl group leading to the synthesis of adipic acid can be enzymatically formed in adipate semialdehyde by an aldehyde dehydrogenase classified under EC 1.2.1.3 (Guerrillot & Vandecasteele, *Eur. J. Biochem.*, 1977, 81, 185-192). See, FIG. 2.

In some embodiments, the second terminal carboxyl group leading to the synthesis of adipic acid is enzymatically formed in adipate semialdehyde by EC 1.2.1.- such as a 5-oxovalerate dehydrogenase classified, for example, under EC 1.2.1.20, such as the gene product of CpnE, a 6-oxohexanoate dehydrogenase classified, for example, EC 1.2.1.63 such as the gene product of ChnE from *Acinetobacter sp.*, or a 7-oxoheptanoate dehydrogenase such as the gene product of ThnG from *Sphingomonas macrogolitabida* (Iwaki et al., *Appl. Environ. Microbiol.*, 1999, 65(11), 5158-5162; Lopez-Sanchez et al., *Appl. Environ. Microbiol.*, 2010, 76(1), 110-118)). See, FIG. 2.

In some embodiments, the second terminal carboxyl group leading to the synthesis of adipic acid is enzymatically formed in adipate semialdehyde by a monooxygenase in the cytochrome P450 family such as CYP4F3B (see, e.g., Sanders et al., *J. Lipid Research*, 2005, 46(5):1001-1008; Sanders et al., *The FASEB Journal*, 2008, 22(6):2064-2071). See, FIG. 2.

Figure 3:
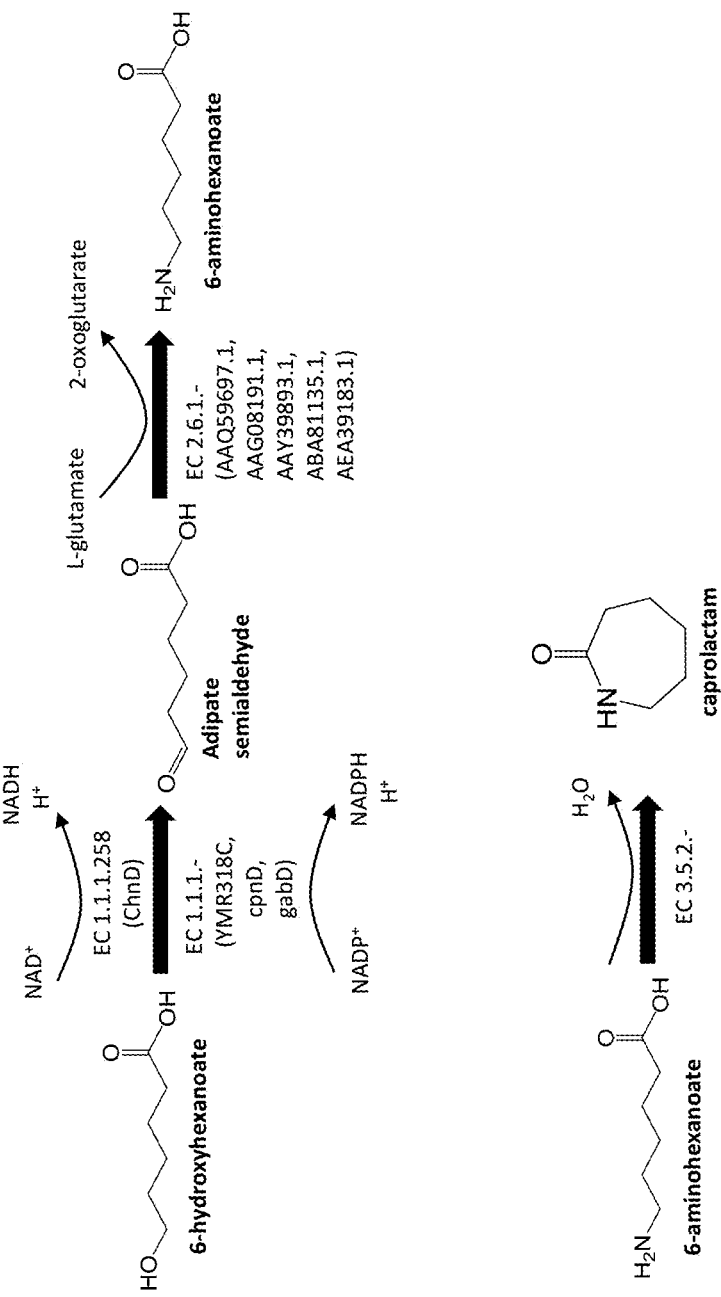
FIG. 3 is a schematic of an exemplary biochemical pathway leading to 6-aminhexanoate using 6-hydroxyhexanoate as a central precursor and a schematic of an exemplary biochemical pathway leading to caprolactam from 6-aminohexanoate.
Figure 4:
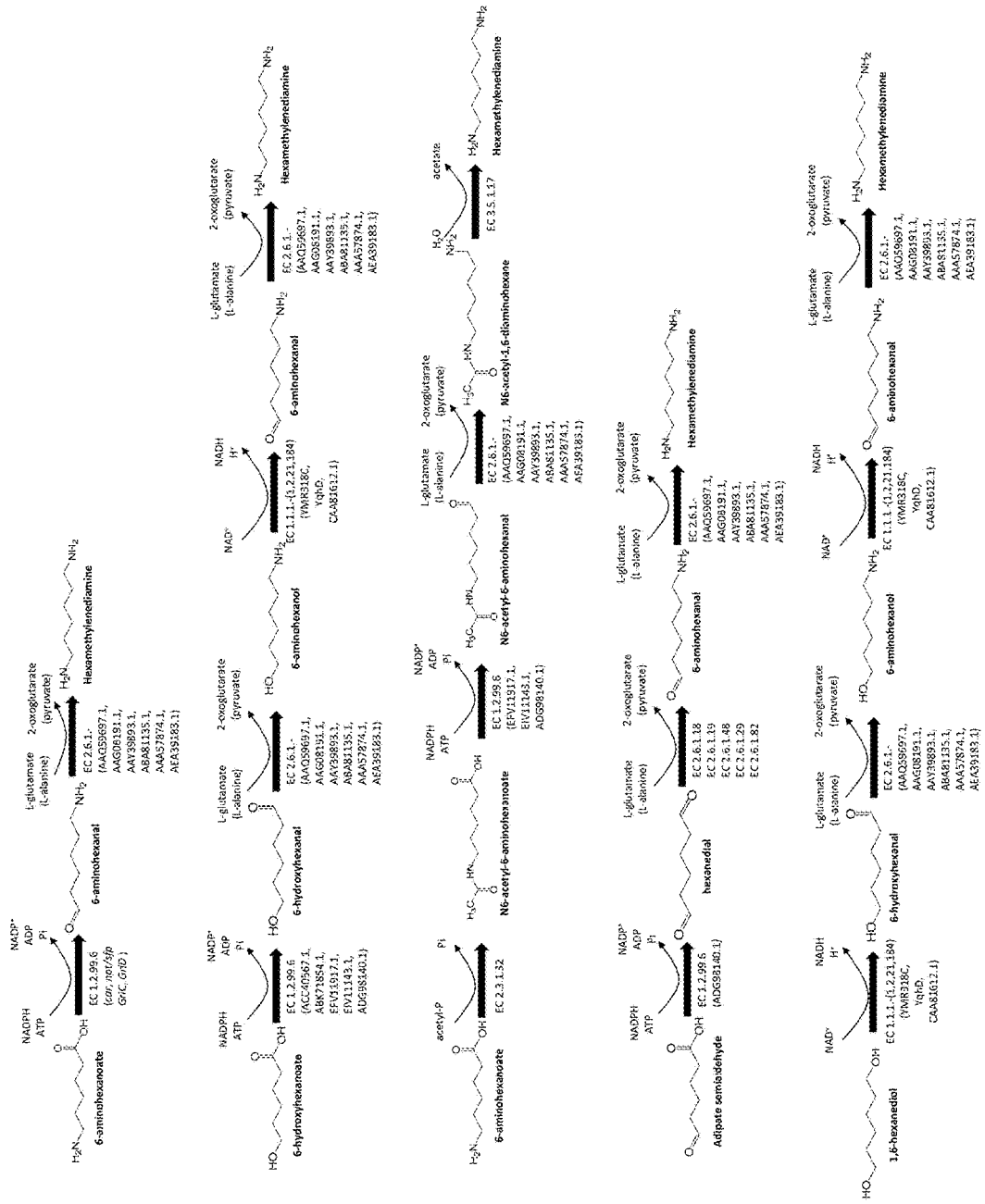
FIG. 4 is a schematic of exemplary biochemical pathways leading to hexamethylenediamine using 6-aminohexanoate, 6-hydroxyhexanoate, adipate semialdehyde, or 1,6-hexanediol as a central precursor.

Enzymes Generating the Terminal Amine Groups in the Biosynthesis of Hexamethylenediamine or 6-Aminohexanoate As depicted in FIG. 3 and FIG. 4, terminal amine groups can be enzymatically formed using a ω-transaminase or a deacylase.

In some embodiments, a terminal amine group leading to the synthesis of 6-aminohexanoic acid is enzymatically formed in adipate semialdehyde by a co-transaminase classified, for example, under EC 2.6.1.-, e.g., EC 2.6.1.18, EC 2.6.1.19, EC 2.6.1.29, EC 2.6.1.48, or EC 2.6.1.82 such as that obtained from *Chromobacterium violaceum* (Genbank Accession No. AAQ59697.1, SEQ ID NO: 7), *Pseudomonas aeruginosa* (Genbank Accession No. AAG08191.1, SEQ ID NO: 8), *Pseudomonas syringae* (Genbank Accession No. AAY39893.1, SEQ ID NO: 9), *Rhodobacter sphaeroides* (Genbank Accession No. ABA81135.1, SEQ ID NO: 10), *Vibrio fluvialis* (Genbank Accession No. AEA39183.1, SEQ ID NO: 12), *Streptomyces griseus*, or *Clostridium viride*. See, FIG. 3.

An additional ω-transaminase that can be used in the methods and hosts described herein is from *Escherichia coli* (Genbank Accession No. AAA57874.1, SEQ ID NO: 11). Some of the ω-transaminases classified, for example, under EC 2.6.1.29 or EC 2.6.1.82 are diamine ω-transaminases (e.g., SEQ ID NO: 11).

The reversible ω-transaminase from *Chromobacterium violaceum* (Genbank Accession No. AAQ59697.1, SEQ ID NO: 7) has demonstrated analogous activity accepting 6-aminohexanoic acid as amino donor, thus forming the first terminal amine group in adipate semialdehyde (Kaulmann et al., *Enzyme and Microbial Technology*, 2007, 41, 628-637).

The reversible 4-aminobubyrate:2-oxoglutarate transaminase from *Streptomyces griseus* has demonstrated activity for the conversion of 6-aminohexanoate to adipate semialdehyde (Yonaha et al., *Eur. J. Biochem.*, 1985, 146, 101-106).

The reversible 5-aminovalerate transaminase from *Clostridium viride* has demonstrated activity for the conversion of 6-aminohexanoate to adipate semialdehyde (Barker et al., *J. Biol. Chem.*, 1987, 262(19), 8994-9003).

In some embodiments, the second terminal amine group leading to the synthesis of hexamethylenediamine is enzymatically formed in 6-aminohexanal by a diamine transaminase classified, for example, under EC 2.6.1.29 or classified, for example, under EC 2.6.1.82, such as the gene product of YgjG from *E. coli* (Genbank Accession No. AAA57874.1, SEQ ID NO: 11). The transaminases classified under EC 2.6.1.18, EC 2.6.1.19, or EC 2.6.1.48 also can be used to synthesize hexamethylenediamine. For example, a transaminase set forth in any one of SEQ ID NOs: 7-10 and 12 also can be used to produce hexamethylenediamine. See, FIG. 4.

The gene product of ygjG accepts a broad range of diamine carbon chain length substrates, such as putrescine, cadaverine and spermidine (Samsonova et al., *BMC Microbiology*, 2003, 3:2).

The diamine transaminase from *E. coli* strain B has demonstrated activity for 1,7 diaminoheptane (Kim, *The Journal of Chemistry*, 1964, 239(3), 783-786).

In some embodiments, the second terminal amine group leading to the synthesis of heptamethylenediamine is enzymatically formed in N6-acetyl-1,6-diaminohexane by a deacylase classified, for example, under EC 3.5.1.17 such as an acyl lysine deacylase.

Figure 5:
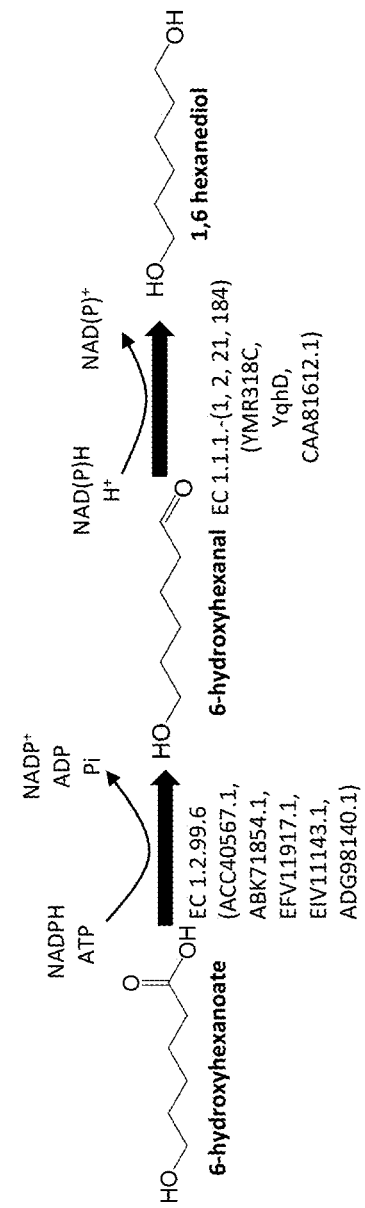
FIG. 5 is a schematic of an exemplary biochemical pathway leading to 1,6-hexanediol using 6-hydroxyhexanoate as a central precursor.

Enzymes Generating the Terminal Hydroxyl Groups in the Biosynthesis of 1,6 Hexanediol As depicted in FIG. 5, the terminal hydroxyl group can be enzymatically formed using an alcohol dehydrogenase. For example, the second terminal hydroxyl group leading to the synthesis of 1,6 hexanediol can be enzymatically formed in 6-hydroxyhexanal by an alcohol dehydrogenase classified under EC 1.1.1.- (e.g., EC 1.1.1.1, 1.1.1.2, 1.1.1.21, or 1.1.1.184) such as the gene product of YMR318C or YqhD (Liu et al., *Microbiology*, 2009, 155, 2078-2085; Larroy et al., 2002, *Biochem J.*, 361(Pt 1), 163-172; Jarboe, 2011, *Appl. Microbiol. Biotechnol.*, 89(2), 249-257) or the protein having GenBank Accession No. CAA81612.1.

Biochemical Pathways

Pathways to 6-Hydroxyhexanoate

In some embodiments, 6-hydroxyhexanoate is synthesized from the central metabolite, 2-oxoglutarate, by conversion of 2-oxoglutarate to L-glutamate by a glutamate synthase classified, for example, under EC 1.4.1.13; followed by conversion of L-glutamate to 4-aminobutyrate by a glutamate decarboxylase classified, for example, under EC 4.1.1.15 or EC 4.1.1.18; followed by conversion of 4-aminobutyrate to succinate semialdehyde by a ω-transaminase classified, for example, under EC 2.6.1.18, EC 2.6.1.19, EC 2.6.1.48, or EC 2.6.1.96 such as the gene product of gabT from *Escherichia coli* (Bartsch et al., *J. Bacteriol.*, 1990, 172(12), 7035); followed by conversion of succinate semialdehyde to 4-hydroxybutyrate by an alcohol dehydrogenase classified, for example, under EC 1.1.1.61 such as the gene product of gbd (e.g., from Sorangium cellulosum), gabD (Bartsch et al., *J. Bacteriol.*, 1990, 172(12), 7035) or YihU (Saito et al., J. Biol. Chem., 2009, 284(24), 16442-16452), or a 5-hydroxyvalerate dehydrogenase such as the gene product of cpnD (see, for example, Iwaki et al., 2002, *Appl. Environ. Microbiol.*, 68(11):5671-5684); followed by conversion of 4-hydroxybutyrate to 4-hydroxybutyryl-CoA using a CoA-ligase classified under, for example, EC 6.2.1- (e.g., EC 6.2.1.40) or a CoA-transferase classified under, for example, EC 2.8.3.- such as the gene product of cat2 from *Clostridium kluyveri*, abfT (SEQ ID NO: 19) from *Clostridium aminobutyricum* or the 5-hydroxypentanoate CoA-transferase from *Clostridium viride*; followed by conversion of 4-hydroxybutyryl-CoA to 4-acetyloxybutyrl-CoA by an alcohol O-acetyltransferase classified under EC 2.3.1.- (e.g., EC 2.3.1.84) such as the gene product of Eht1 (SEQ ID NO:17); followed by conversion of 4-acetyloxybutyryl-CoA to 6-acetyloxy-3-oxohexanoyl-CoA using a β-ketothiolase classified, for example, under EC 2.3.1.16 or EC 2.3.1.174 such as the gene product of bktB, yqeF, or paaJ (e.g., SEQ ID NO: 1 or 13); followed by conversion of 6-acetyloxy-3-oxohexanoyl-CoA to 6-acetyloxy-3-hydroxyhexanoyl-CoA using a 3-hydroxyacyl-CoA dehydrogenase classified, for example, under EC 1.1.1.- such as EC 1.1.1.35 (e.g., the gene product of fadB), EC 1.1.1.36 (e.g., the gene product of phaB), or EC 1.1.1.157 (e.g., the gene product of hbd) or a 3-oxoacyl-CoA reductase classified, for example, under EC 1.1.1.100, such as the gene product of fabG; followed by conversion of 6-acetyloxy-3-hydroxyhexanoyl-CoA to 6-acetyloxy-hex-2-enoyl-CoA using an enoyl-CoA hydratase classified, for example, under EC 4.2.1.17 such as the gene product of crt or classified under EC 4.2.1.119 such as the gene product of phaJ; followed by conversion of 6-acetyloxy-hex-2-enoyl-CoA to 6-acetyloxyhexanoyl-CoA by a trans-2-enoyl-CoA reductase classified, for example, under EC 1.3.1.38, EC 1.3.1.44, or EC 1.3.1.8 such as the gene product of Egter (SEQ ID NO: 24), tdter (SEQ ID NO: 23), YdiO-YdiQRST or SEQ ID NOs: 25-28; followed by conversion of 6-acetyloxyhexanoyl-CoA to 6-acetyloxyhexanoic acid by a thioesterase classified, for example, under EC 3.1.2.- such as the gene product of YciA or Acot13 or a CoA-transferase classified, for example, under EC 2.8.3.-; followed by conversion of 6-acetyloxyhexanoic acid to 6-hydroxyhexanoate by an esterase classified under EC 3.1.1.- (e.g., a carboxyl esterase classified under EC 3.1.1.1 or an acetoacetyl esterase classified under EC 3.1.1.6) such as the gene product of EstC (SEQ ID NO:15). In some embodiments, 6-acetyloxyhexanoyl-CoA can be converted to 6-hydroxyhexanoyl-CoA using an esterase classified, for example, under EC 3.1.1.- (e.g., a pimelyl-[acp] methylester esterase classified under EC 3.1.1.85); followed by conversion to 6-hydroxyhexanoate by a thioesterase classified, for example, under EC 3.1.2.- such as the gene product of YciA or Acot13 or a CoA-transferase classified, for example, under EC 2.8.3.- See FIG. 1.

In some embodiments, 4-hydroxybutyrate produced as described above can be converted to 4-acetyloxybutyric acid using an alcohol O-acetyltransferase classified under EC 2.3.1.- (e.g., EC 2.3.1.84) such as the gene product of Eht1; followed by conversion of 4-acetyloxybutyric acid to 4-acetyloxybutyryl-CoA using a CoA-ligase classified under, for example, EC 6.2.1- (e.g., EC 6.2.1.40) or a CoA-transferase classified under, for example, EC 2.8.3.- such as the gene product of cat2 from *Clostridium kluyveri*, abfT (e.g., SEQ ID NO: 19) from *Clostridium aminobutyricum* or the 5-hydroxypentanoate CoA-transferase from *Clostridium viride*. 4-acetyloxybutyryl-CoA can be converted to 6-hydroxyhexanoate as described above.

In some embodiments, 2-oxoglutarate is converted to succinate semialdehyde using a decarboxylase classified under EC 4.1.1.- such as a phenylpyruvate decarboxylase classified, for example, under EC 4.1.1.43, a 2-oxoglutarate decarboxylase classified, for example, under EC 4.1.1.71 (e.g., SEQ ID NO: 21), a branch-chain decarboxylase classified, for example, under EC 4.1.1.72 such as the gene product of kdcA or kivD (e.g., SEQ ID NO: 22), or a indolepyruvate decarboxylase classified, for example, under EC 4.1.1.74 (e.g., SEQ ID NO: 20). Succinate semialdehyde produced in this fashion can be converted to 6-hydroxyhexanoate as described above. See, FIG. 1.

Pathways Using 6-Hydroxyhexanoate as Central Precursor to Adipic Acid

In some embodiments, adipic acid is synthesized from 6-hydroxyhexanoate, by conversion of 6-hydroxyhexanoate to adipate semialdehyde by an alcohol dehydrogenase classified under EC 1.1.1.- such as the gene product of YMR318C (classified, for example, under EC 1.1.1.2, see Genbank Accession No. CAA90836.1) (Larroy et al., 2002, *Biochem J.*, 361(Pt 1), 163-172), cpnD (Iwaki et al., 2002, *Appl. Environ. Microbiol.*, 68(11):5671-5684) or gabD (LUtke-Eversloh & Steinbüchel, 1999, *FEMS Microbiology Letters*, 181(1):63-71) or a 6-hydroxyhexanoate dehydrogenase classified, for example, under EC 1.1.1.258 such as the gene product of ChnD (Iwaki et al., *Appl. Environ. Microbiol.*, 1999, 65(11):5158-5162); followed by conversion of adipate semialdehyde to adipic acid by a dehydrogenase classified, for example, under EC 1.2.1.- such as a 7-oxoheptanoate dehydrogenase (e.g., the gene product of ThnG), a 6-oxohexanoate dehydrogenase (e.g., the gene product of ChnE), a glutarate semialdehyde dehydrogenase classified, for example, under EC 1.2.1.20, a 5-oxovalerate dehydrogenase such as the gene product of CpnE, or an aldehyde dehydrogenase classified under EC 1.2.1.3. See FIG. 2. The alcohol dehydrogenase encoded by YlVIR318C has broad substrate specificity, including the oxidation of C6 alcohols.

In some embodiments, adipic acid is synthesized from the central precursor, 6-hydroxyhexanoate, by conversion of 6-hydroxyhexanoate to adipate semialdehyde by a cytochrome P450 (Sanders et al., *J. Lipid Research*, 2005, 46(5), 1001-1008; Sanders et al., *The FASEB Journal*, 2008, 22(6), 2064-2071); followed by conversion of adipate semialdehyde to adipic acid by a monooxygenase in the cytochrome P450 family such as CYP4F3B. See FIG. 2.

Pathway Using 6-Hydroxyhexanoate as Central Precursor to 6-Aminohexanoate and ε-Caprolactam In some embodiments, 6-aminohexanoate is synthesized from the central precursor, 6-hydroxyhexanoate, by conversion of 6-hydroxyhexanoate to adipate semialdehyde by an alcohol dehydrogenase classified, for example, under EC 1.1.1.2 such as the gene product of YMR318C, a 6-hydroxyhexanoate dehydrogenase classified, for example, under EC 1.1.1.258, a 5-hydroxypentanoate dehydrogenase classified, for example, under EC 1.1.1.- such as the gene product of cpnD, or a 4-hydroxybutyrate dehydrogenase classified, for example, under EC 1.1.1.- such as the gene product of gabD; followed by conversion of adipate semialdehyde to 6-aminohexanoate by a co-transaminase (EC 2.6.1.18, EC 2.6.1.19, EC 2.6.1.29, EC 2.6.1.48, or EC 2.6.1.82 such as one of SEQ ID NOs:7-10 or 12, see above). See FIG. 3.

In some embodiments, ε-caprolactam is synthesized from the central precursor, 6-hydroxyhexanoate, by conversion of 6-hydroxyhexanoate to adipate semialdehyde by an alcohol dehydrogenase classified, for example, under EC 1.1.1.2 such as the gene product of YMR318C, a 6-hydroxyhexanoate dehydrogenase classified, for example, under EC 1.1.1.258, a 5-hydroxypentanoate dehydrogenase classified, for example, under EC 1.1.1.- such as the gene product of cpnD, or a 4-hydroxybutyrate dehydrogenase classified, for example, under EC 1.1.1.- such as the gene product of gabD; followed by conversion of adipate semialdehyde to 6-aminohexanoate by a ω-transaminase (EC 2.6.1.18, EC 2.6.1.19, EC 2.6.1.29, EC 2.6.1.48, or EC 2.6.1.82); followed by conversion of 6-aminohexanoate to ε-caprolactam by an amidohydrolase (EC 3.5.2.-). See FIG. 3.

In some embodiments, ε-caprolactam is synthesized from the central precursor, 6-aminohexanoate by the last step described above (i.e., by conversion using an amidohydrolase such as one in EC. 3.5.2.-). See FIG. 3.

Pathway Using 6-Aminohexanoate, 6-Hydroxyhexanoate, Adipate Semialdehyde, or 1,6-Hexanediol as a Central Precursor to Hexamethylenediamine In some embodiments, hexamethylenediamine is synthesized from the central precursor, 6-aminohexanoate, by conversion of 6-aminohexanoate to 6-aminohexanal by a carboxylate reductase classified, for example, under EC 1.2.99.6 such as the gene product of car in combination with a phosphopantetheine transferase enhancer (e.g., encoded by a sfp gene from *Bacillus subtilis* or npt gene from *Nocardia*) or the gene products of GriC and GriD from *Streptomyces griseus* (Suzuki et al., *J. Antibiot.*, 2007, 60(6), 380-387); followed by conversion of 6-aminohexanal to hexamethylenediamine by a ω-transaminase such as a ω-transaminase in EC 2.6.1.-, (e.g., EC 2.6.1.18, EC 2.6.1.19, EC 2.6.1.48, EC 2.6.1.82 such as SEQ ID NOs:7-12). The carboxylate reductase can be obtained, for example, from *Mycobacterium marinum* (Genbank Accession No. ACC40567.1, SEQ ID NO: 2), *Mycobacterium smegmatis* (Genbank Accession No. ABK71854.1, SEQ ID NO: 3), *Segniliparus rugosus* (Genbank Accession No. EFV11917.1, SEQ ID NO: 4), *Mycobacterium massiliense* (Genbank Accession No. EIV11143.1, SEQ ID NO: 5), or *Segniliparus rotundus* (Genbank Accession No. ADG98140.1, SEQ ID NO: 6). See FIG. 4.

The carboxylate reductase encoded by the gene product of car and enhancer npt (SEQ ID NO: 14) or sfp (SEQ ID NO: 13) has broad substrate specificity, including terminal difunctional C4 and C5 carboxylic acids (Venkitasubramanian et al., *Enzyme and Microbial Technology*, 2008, 42, 130-137).

In some embodiments, hexamethylenediamine is synthesized from the central precursor, 6-hydroxyhexanoate (which can be produced as described in FIG. 1), by conversion of 6-hydroxyhexanoate to 6-hydroxyhexanal by a carboxylate reductase classified, for example, under EC 1.2.99.6 such as the gene product of car (see above) in combination with a phosphopantetheine transferase enhancer (e.g., encoded by a sfp gene from *Bacillus subtilis* or npt gene from *Nocardia*) or the gene product of GriC & GriD (Suzuki et al., 2007, supra); followed by conversion of 6-aminohexanal to 6-aminohexanol by a ω-transaminase classified, for example, under EC 2.6.1.18, EC 2.6.1.19, EC 2.6.1.29, EC 2.6.1.48, or EC 2.6.1.82 such as SEQ ID NOs:7-12, see above; followed by conversion to 6-aminohexanal by an alcohol dehydrogenase classified, for example, under EC 1.1.1.- (e.g., EC 1.1.1.1, EC 1.1.1.2, 1.1.1.21, or EC 1.1.1.184) such as the gene product of YMR318C or YqhD (Liu et al., *Microbiology*, 2009, 155, 2078-2085; Larroy et al., 2002, *Biochem J.*, 361(Pt 1), 163-172; Jarboe, 2011, *Appl. Microbiol. Biotechnol.*, 89(2), 249-257) or the protein having GenBank Accession No. CAA81612.1; followed by conversion to hexamethylenediamine by a ω-transaminase classified, for example, under EC 2.6.1.18, EC 2.6.1.19, EC 2.6.1.29, EC 2.6.1.48, or EC 2.6.1.82 such as SEQ ID NOs:7-12, see above. See FIG. 4.

In some embodiments, hexamethylenediamine is synthesized from the central precursor, 6-aminohexanoate, by conversion of 6-aminohexanoate to N6-acetyl-6-aminohexanoate by an N-acetyltransferase such as a lysine N-acetyltransferase classified, for example, under EC 2.3.1.32; followed by conversion to N6-acetyl-6-aminohexanal by a carboxylate reductase classified, for example, under EC 1.2.99.6 such as the gene product of car (see above, e.g., SEQ ID NO: 4, 5, or 6) in combination with a phosphopantetheine transferase enhancer (e.g., encoded by a sfp gene from *Bacillus subtilis* or npt gene from *Nocardia*) or the gene product of GriC & GriD; followed by conversion to N6-acetyl-1,6-diaminohexane by a ω-transaminase classified, for example, under EC 2.6.1.18, EC 2.6.1.19, EC 2.6.1.29, EC 2.6.1.48, or EC 2.6.1.82 such as SEQ ID NOs:7-12, see above; followed by conversion to heptamethylenediamine by an acyl lysine deacylase classified, for example, under EC 3.5.1.17. See, FIG. 4.

In some embodiments, hexamethylenediamine is synthesized from the central precursor, adipate semialdehyde, by conversion of adipate semialdehyde to hexanedial by a carboxylate reductase classified, for example, under EC 1.2.99.6 such as the gene product of car (see above, e.g., SEQ NO:6) in combination with a phosphopantetheine transferase enhancer (e.g., encoded by a sfp gene from *Bacillus subtilis* or npt gene from *Nocardia*) or the gene product of GriC & GriD; followed by conversion to 6-aminohexanal by a ω-transaminase classified, for example, under EC 2.6.1.18, EC 2.6.1.19, EC 2.6.1.29, EC 2.6.1.48, or EC 2.6.1.82; followed by conversion to hexamethylenediamine by a ω-transaminase classified, for example, under EC 2.6.1.18, EC 2.6.1.19, EC 2.6.1.29, EC 2.6.1.48, or EC 2.6.1.82 such as SEQ ID NOs:7-12. See FIG. 4.

In some embodiments, hexamethylenediamine is synthesized from 1,6-hexanediol by conversion of 1,6-hexanediol to 6-hydroxyhexanal using an alcohol dehydrogenase classified, for example, under EC 1.1.1.- (e.g., EC 1.1.1.1, EC 1.1.1.2, EC 1.1.1.21, or EC 1.1.1.184) such as the gene product of YMR318C or YqhD or the protein having GenBank Accession No. CAA81612.1; followed by conversion to 6-aminohexanol by a co-transaminase classified, for example, under EC 2.6.1.18, EC 2.6.1.19, EC 2.6.1.29, EC 2.6.1.48, or EC 2.6.1.82 such as SEQ ID NOs:7-12, followed by conversion to 6-aminohexanal by an alcohol dehydrogenase classified, for example, under EC 1.1.1.- (e.g., EC 1.1.1.1, EC 1.1.1.2, EC 1.1.1.21, or EC 1.1.1.184) such as the gene product of YMR318C or YqhD or the protein having GenBank Accession No. CAA81612.1, followed by conversion to hexamethylenediamine by a ω-transaminase classified, for example, under EC 2.6.1.18, EC 2.6.1.19, EC 2.6.1.29, EC 2.6.1.48, or EC 2.6.1.82 such as SEQ ID NOs: 7-12. See FIG. 4.

Pathways Using 6-Hydroxyhexanoate as Central Precursor to 1,6-Hexanediol

In some embodiments, 1,6 hexanediol is synthesized from the central precursor, 6-hydroxyhexanoate, by conversion of 6-hydroxyhexanoate to 6-hydroxyhexanal by a carboxylate reductase classified, for example, under EC 1.2.99.6 such as the gene product of car (see above, e.g., SEQ ID NO: 2, 3, 4, 5, or 6) in combination with a phosphopantetheine transferase enhancer (e.g., encoded by a sfp gene from *Bacillus subtilis* or npt gene from *Nocardia*) or the gene products of GriC and GriD from *Streptomyces griseus* (Suzuki et al., *J. Antibiot.*, 2007, 60(6), 380-387); followed by conversion of 6-hydroxyhexanal to 1,6 hexanediol by an alcohol dehydrogenase (classified, for example, under EC 1.1.1.- such as EC 1.1.1.1, EC 1.1.1.2, EC 1.1.1.21, or EC 1.1.1.184) such as the gene product of YMR318C or YqhD (from *E. coli*, GenBank Accession No. AAA69178.1) (see, e.g., Liu et al., *Microbiology*, 2009, 155, 2078-2085; Larroy et al., 2002, *Biochem J.*, 361(Pt 1), 163-172; or Jarboe, 2011, *Appl. Microbiol. Biotechnol.*, 89(2), 249-257) or the protein having GenBank Accession No. CAA81612.1 (from *Geobacillus stearothermophilus*). See, FIG. 5.

Cultivation Strategy

In some embodiments, one or more C6 building blocks are biosynthesized in a recombinant host using anaerobic, aerobic or micro-aerobic cultivation conditions. In some embodiments, the cultivation strategy entails nutrient limitation such as nitrogen, phosphate or oxygen limitation.

In some embodiments, a cell retention strategy using, for example, ceramic hollow fiber membranes can be employed to achieve and maintain a high cell density during either fed-batch or continuous fermentation.

In some embodiments, the principal carbon source fed to the fermentation in the synthesis of one or more C6 building blocks can derive from biological or non-biological feedstocks.

In some embodiments, the biological feedstock can be or can derive from, monosaccharides, disaccharides, lignocellulose, hemicellulose, cellulose, lignin, levulinic acid and formic acid, triglycerides, glycerol, fatty acids, agricultural waste, condensed distillers' solubles, or municipal waste.

The efficient catabolism of crude glycerol stemming from the production of biodiesel has been demonstrated in several microorganisms such as *Escherichia coli, Cupriavidus necator, Pseudomonas oleavorans, Pseudomonas putida* and *Yarrowia hpolytica* (Lee et al., *Appl. Biochem. Biotechnol.*, 2012, 166:1801-1813; Yang et al., *Biotechnology for Biofuels*, 2012, 5:13; Meijnen et al., *Appl. Microbiol. Biotechnol.*, 2011, 90:885-893).

The efficient catabolism of lignocellulosic-derived levulinic acid has been demonstrated in several organisms such as *Cupriavidus necator* and *Pseudomonas putida* in the synthesis of 3-hydroxyvalerate via the precursor propanoyl-CoA (Jaremko and Yu, 2011, supra; Martin and Prather, *J. Biotechnol.*, 2009, 139:61-67).

The efficient catabolism of lignin-derived aromatic compounds such as benzoate analogues has been demonstrated in several microorganisms such as *Pseudomonas putida, Cupriavidus necator* (Bugg et al., *Current Opinion in Biotechnology*, 2011, 22, 394-400; Perez-Pantoja et al., *FEMS Microbiol. Rev.*, 2008, 32, 736-794).

The efficient utilization of agricultural waste, such as olive mill waste water has been demonstrated in several microorganisms, including *Yarrowia hpolytica* (Papanikolaou et al., *Bioresour. Technol.*, 2008, 99(7):2419-2428).

The efficient utilization of fermentable sugars such as monosaccharides and disaccharides derived from cellulosic, hemicellulosic, cane and beet molasses, cassava, corn and other agricultural sources has been demonstrated for several microorganism such as *Escherichia coli, Corynebacterium glutamicum* and *Lactobacillus delbrueckii* and *Lactococcus lactis* (see, e.g., Hermann et al, *J. Biotechnol.*, 2003, 104: 155-172; Wee et al., *Food Technol. Biotechnol.*, 2006, 44(2):163-172; Ohashi et al., *J. Bioscience and Bioengineering*, 1999, 87(5):647-654).

The efficient utilization of furfural, derived from a variety of agricultural lignocellulosic sources, has been demonstrated for *Cupriavidus necator* (Li et al., *Biodegradation*, 2011, 22:1215-1225).

In some embodiments, the non-biological feedstock can be or can derive from natural gas, syngas, $CO_2/H_2$, methanol, ethanol, benzoate, non-volatile residue (NVR) or a caustic wash waste stream from cyclohexane oxidation processes, or terephthalic acid/isophthalic acid mixture waste streams.

The efficient catabolism of methanol has been demonstrated for the methylotrophic yeast *Pichia pastoris*.

The efficient catabolism of ethanol has been demonstrated for *Clostridium kluyveri* (Seedorf et al., *Proc. Natl. Acad. Sci. USA*, 2008, 105(6) 2128-2133).

The efficient catabolism of $CO_2$ and $H_2$, which may be derived from natural gas and other chemical and petrochemical sources, has been demonstrated for *Cupriavidus necator* (Prybylski et al., *Energy, Sustainability and Society*, 2012, 2:11).

The efficient catabolism of syngas has been demonstrated for numerous microorganisms, such as *Clostridium ljungdahlii* and *Clostridium autoethanogenum* (Kopke et al., *Applied and Environmental Microbiology*, 2011, 77(15): 5467-5475).

The efficient catabolism of the non-volatile residue waste stream from cyclohexane processes has been demonstrated for numerous microorganisms, such as *Delftia acidovorans* and *Cupriavidus necator* (Ramsay et al., *Applied and Environmental Microbiology*, 1986, 52(1):152-156).

In some embodiments, the host microorganism is a prokaryote. For example, the prokaryote can be a bacterium from the genus *Escherichia* such as *Escherichia coli*; from the genus Clostridia such as *Clostridium ljungdahlii*, *Clostridium autoethanogenum* or *Clostridium kluyveri*; from the genus *Corynebacteria* Such as *Corynebacterium glutamicum*; from the genus *Cupriavidus* such as *Cupriavidus necator* or *Cupriavidus metallidurans*; from the genus *Pseudomonas* such as *Pseudomonas fluorescens*, *Pseudomonas putida* or *Pseudomonas oleavorans*; from the genus *Delftia* such as *Delftia acidovorans*; from the genus *Bacillus* such as *Bacillus subtillis*; from the genus *Lactobacillus* such as *Lactobacillus delbrueckii*; or from the genus *Lactococcus* such as *Lactococcus lactis*. Such prokaryotes also can be a source of genes to construct recombinant host cells described herein that are capable of producing one or more C6 building blocks.

In some embodiments, the host microorganism is a eukaryote. For example, the eukaryote can be a filamentous fungus, e.g., one from the genus *Aspergillus* such as *Aspergillus niger*. Alternatively, the eukaryote can be a yeast, e.g., one from the genus *Saccharomyces* such as *Saccharomyces cerevisiae*; from the genus *Pichia* such as *Pichia pastoris*; or from the genus *Yarrowia* such as *Yarrowia lipolytica*; from the genus *Issatchenkia* such as *Issathenkia orientalis*; from the genus *Debaryomyces* such as *Debaryomyces hansenii*; from the genus *Arxula* such as *Arxula adenoinivorans*; or from the genus *Kluyveromyces* such as *Kluyveromyces lactis*. Such eukaryotes also can be a source of genes to construct recombinant host cells described herein that are capable of producing one or more C6 building blocks.

Metabolic Engineering

The present document provides methods involving less than all the steps described for all the above pathways. Such methods can involve, for example, one, two, three, four, five, six, seven, eight, nine, ten, eleven, twelve or more of such steps. Where less than all the steps are included in such a method, the first, and in some embodiments the only, step can be any one of the steps listed.

Furthermore, recombinant hosts described herein can include any combination of the above enzymes such that one or more of the steps, e.g., one, two, three, four, five, six, seven, eight, nine, ten, or more of such steps, can be performed within a recombinant host. This document provides host cells of any of the genera and species listed and genetically engineered to express one or more (e.g., two, three, four, five, six, seven, eight, nine, 10, 11, 12 or more) recombinant forms of any of the enzymes recited in the document. Thus, for example, the host cells can contain exogenous nucleic acids encoding enzymes catalyzing one or more of the steps of any of the pathways described herein.

In addition, this document recognizes that where enzymes have been described as accepting CoA-activated substrates, analogous enzyme activities associated with [acp]-bound substrates exist that are not necessarily in the same enzyme class.

Also, this document recognizes that where enzymes have been described accepting (R)-enantiomers of substrate, analogous enzyme activities associated with (S)-enantiomer substrates exist that are not necessarily in the same enzyme class.

This document also recognizes that where an enzyme is shown to accept a particular co-factor, such as NADPH, or co-substrate, such as acetyl-CoA, many enzymes are promiscuous in terms of accepting a number of different co-factors or co-substrates in catalyzing a particular enzyme activity. Also, this document recognizes that where enzymes have high specificity for e.g., a particular co-factor such as NADH, an enzyme with similar or identical activity that has high specificity for the co-factor NADPH may be in a different enzyme class.

In some embodiments, the enzymes in the pathways outlined herein are the result of enzyme engineering via non-direct or rational enzyme design approaches with aims of improving activity, improving specificity, reducing feedback inhibition, reducing repression, improving enzyme solubility, changing stereo-specificity, or changing co-factor specificity.

In some embodiments, the enzymes in the pathways outlined here can be gene dosed, i.e., overexpressed, into the resulting genetically modified organism via episomal or chromosomal integration approaches.

In some embodiments, genome-scale system biology techniques such as Flux Balance Analysis can be utilized to devise genome scale attenuation or knockout strategies for directing carbon flux to a C6 building block.

Attenuation strategies include, but are not limited to; the use of transposons, homologous recombination (double cross-over approach), mutagenesis, enzyme inhibitors and RNAi interference.

In some embodiments, fluxomic, metabolomic and transcriptomal data can be utilized to inform or support genome-scale system biology techniques, thereby devising genome scale attenuation or knockout strategies in directing carbon flux to a C6 building block.

In some embodiments, the host microorganism's tolerance to high concentrations of a C6 building block can be improved through continuous cultivation in a selective environment.

In some embodiments, the host microorganism's endogenous biochemical network can be attenuated or augmented to (1) ensure the intracellular availability of acetyl-CoA and 2-oxoglutarate, (2) create an NADH or NADPH imbalance that may only be balanced via the formation of one or more C6 building blocks, (3) prevent degradation of central metabolites, central precursors leading to and including one or more C6 building blocks and/or (4) ensure efficient efflux from the cell.

In some embodiments requiring intracellular availability of acetyl-CoA for C6 building block synthesis, endogenous enzymes catalyzing the hydrolysis of acetyl-CoA such as short-chain length thioesterases can be attenuated in the host organism.

In some embodiments requiring the intracellular availability of acetyl-CoA for C6 building block synthesis, an endogenous phosphotransacetylase generating acetate such as pta can be attenuated (Shen et al., *Appl. Environ. Microbiol.*, 2011, 77(9):2905-2915).

In some embodiments requiring the intracellular availability of acetyl-CoA for C6 building block synthesis, an endogenous gene in an acetate synthesis pathway encoding an acetate kinase, such as ack, can be attenuated.

In some embodiments requiring the intracellular availability of acetyl-CoA and NADH for C6 building block synthesis, an endogenous gene encoding an enzyme that catalyzes the degradation of pyruvate to lactate such as lactate dehydrogenase encoded by ldhA can be attenuated (Shen et al., 2011, supra).

In some embodiments, enzymes that catalyze anaplerotic reactions such as PEP carboxylase and/or pyruvate carboxylase can be overexpressed in the host organism.

In some embodiments requiring the intracellular availability of acetyl-CoA and NADH for C6 building block synthesis, endogenous genes encoding enzymes, such as menaquinol-fumarate oxidoreductase, that catalyze the degradation of phophoenolpyruvate to succinate such as frdBC can be attenuated (see, e.g., Shen et al., 2011, supra).

In some embodiments requiring the intracellular availability of acetyl-CoA and NADH for C6 building block synthesis, an endogenous gene encoding an enzyme that catalyzes the degradation of acetyl-CoA to ethanol such as the alcohol dehydrogenase encoded by adhE can be attenuated (Shen et al., 2011, supra).

In some embodiments, where pathways require excess NADH co-factor for C6 building block synthesis, a recombinant formate dehydrogenase gene can be overexpressed in the host organism (Shen et al., 2011, supra).

In some embodiments, where pathways require excess NADH co-factor for C6 building block synthesis, a recombinant NADH-consuming transhydrogenase can be attenuated.

In some embodiments, an endogenous gene encoding an enzyme that catalyzes the degradation of pyruvate to ethanol such as pyruvate decarboxylase can be attenuated.

In some embodiments requiring the intracellular availability of acetyl-CoA for C6 building block synthesis, a recombinant acetyl-CoA synthetase such as the gene product of acs can be overexpressed in the microorganism (Satoh et al., *J. Bioscience and Bioengineering*, 2003, 95(4):335-341).

In some embodiments, carbon flux can be directed into the pentose phosphate cycle to increase the supply of NADPH by attenuating an endogenous glucose-6-phosphate isomerase (EC 5.3.1.9).

In some embodiments, carbon flux can be redirected into the pentose phosphate cycle to increase the supply of NADPH by overexpression a 6-phosphogluconate dehydrogenase and/or a transketolase (Lee et al., 2003, *Biotechnology Progress*, 19(5), 1444-1449).

In some embodiments, where pathways require excess NADPH co-factor in the synthesis of a C6 building block, a gene such as UdhA encoding a puridine nucleotide transhydrogenase can be overexpressed in the host organisms (Brigham et al., *Advanced Biofuels and Bioproducts*, 2012, Chapter 39, 1065-1090).

In some embodiments, where pathways require excess NADPH co-factor in the synthesis of a C6 Building Block, a recombinant glyceraldehyde-3-phosphate-dehydrogenase gene such as GapN can be overexpressed in the host organisms (Brigham et al., 2012, supra).

In some embodiments, where pathways require excess NADPH co-factor in the synthesis of a C6 building block, a recombinant malic enzyme gene such as maeA or maeB can be overexpressed in the host organisms (Brigham et al., 2012, supra).

In some embodiments, where pathways require excess NADPH co-factor in the synthesis of a C6 building block, a recombinant glucose-6-phosphate dehydrogenase gene such as zwf can be overexpressed in the host organisms (Lim et al., *J. Bioscience and Bioengineering*, 2002, 93(6), 543-549).

In some embodiments, where pathways require excess NADPH co-factor in the synthesis of a C6 building block, a recombinant fructose 1,6 diphosphatase gene such as fbp can be overexpressed in the host organisms (Becker et al., *J. Biotechnol.*, 2007, 132:99-109).

In some embodiments, where pathways require excess NADPH co-factor in the synthesis of a C6 building block, endogenous triose phosphate isomerase (EC 5.3.1.1) can be attenuated.

In some embodiments, where pathways require excess NADPH co-factor in the synthesis of a C6 building block, a recombinant glucose dehydrogenase such as the gene product of gdh can be overexpressed in the host organism (Satoh et al., *J. Bioscience and Bioengineering*, 2003, 95(4):335-341).

In some embodiments, endogenous enzymes facilitating the conversion of NADPH to NADH can be attenuated, such as the NADH generation cycle that may be generated via inter-conversion of glutamate dehydrogenases classified under EC 1.4.1.2 (NADH-specific) and EC 1.4.1.4 (NADPH-specific).

In some embodiments, an endogenous glutamate dehydrogenase (EC 1.4.1.3) that utilizes both NADH and NADPH as co-factors can be attenuated.

In some embodiments, a membrane-bound cytochrome P450 such as CYP4F3B can be solubilized by only expressing the cytosolic domain and not the N-terminal region that anchors the P450 to the endoplasmic reticulum (Scheller et al., *J. Biol. Chem.*, 1994, 269(17): 12779-12783).

In some embodiments, an enoyl-CoA reductase can be solubilized via expression as a fusion protein with a small soluble protein, for example, the maltose binding protein (Gloerich et al., *FEBS Letters*, 2006, 580, 2092-2096).

In some embodiments using hosts that naturally accumulate polyhydroxyalkanoates, the endogenous polymer synthase enzymes can be attenuated in the host strain.

In some embodiments, an L-alanine dehydrogenase can be overexpressed in the host to regenerate L-alanine from pyruvate as an amino donor for ω-transaminase reactions.

In some embodiments, an L-glutamate dehydrogenase, a L-glutamine synthetase, or a glutamate synthase can be overexpressed in the host to regenerate L-glutamate from 2-oxoglutarate as an amino donor for ω-transaminase reactions.

In some embodiments, enzymes such as a pimeloyl-CoA dehydrogenase classified under, EC 1.3.1.62; an acyl-CoA dehydrogenase classified, for example, under EC 1.3.8.7, EC 1.3.8.1, or EC 1.3.99.-; and/or a butyryl-CoA dehydrogenase classified, for example, under EC 1.3.8.6 that degrade central metabolites and central precursors leading to and including C6 building blocks can be attenuated.

In some embodiments, endogenous enzymes activating C6 building blocks via Coenzyme A esterification such as CoA-ligases (e.g., an adipyl-CoA synthetase) classified under, for example, EC 6.2.1.- can be attenuated.

In some embodiments, the efflux of a C6 building block across the cell membrane to the extracellular media can be enhanced or amplified by genetically engineering structural modifications to the cell membrane or increasing any associated transporter activity for a C6 building block.

The efflux of hexamethylenediamine can be enhanced or amplified by overexpressing broad substrate range multidrug transporters such as Blt from *Bacillus subtilis* (Woolridge et al., 1997, *J. Biol. Chem.*, 272(14):8864-8866); AcrB and AcrD from *Escherichia coli* (Elkins & Nikaido, 2002, *J. Bacteriol.*, 184(23), 6490-6499), NorA from *Staphylococcus aereus* (Ng et al., 1994, *Antimicrob Agents Chemother*, 38(6), 1345-1355), or Bmr from *Bacillus subtilis* (Neyfakh, 1992, *Antimicrob Agents Chemother*, 36(2), 484-485).

The efflux of 6-aminohexanoate and heptamethylenediamine can be enhanced or amplified by overexpressing the solute transporters such as the lysE transporter from *Corynebacterium glutamicum* (Bellmann et al., 2001, *Microbiology*, 147, 1765-1774).

The efflux of adipic acid can be enhanced or amplified by overexpressing a dicarboxylate transporter such as the SucE transporter from *Corynebacterium glutamicum* (Huhn et al., *Appl. Microbiol. & Biotech.*, 89(2), 327-335).

Producing C6 Building Blocks Using a Recombinant Host

Typically, one or more C6 building blocks can be produced by providing a host microorganism and culturing the provided microorganism with a culture medium containing a suitable carbon source as described above. In general, the culture media and/or culture conditions can be such that the microorganisms grow to an adequate density and produce a C6 building block efficiently. For large-scale production processes, any method can be used such as those described elsewhere (Manual of Industrial Microbiology and Biotechnology, $2^{nd}$ Edition, Editors: A. L. Demain and J. E. Davies, ASM Press; and Principles of Fermentation Technology, P. F. Stanbury and A. Whitaker, Pergamon). Briefly, a large tank (e.g., a 100 gallon, 200 gallon, 500 gallon, or more tank) containing an appropriate culture medium is inoculated with a particular microorganism. After inoculation, the microorganism is incubated to allow biomass to be produced. Once a desired biomass is reached, the broth containing the microorganisms can be transferred to a second tank. This second tank can be any size. For example, the second tank can be larger, smaller, or the same size as the first tank. Typically, the second tank is larger than the first such that additional culture medium can be added to the broth from the first tank. In addition, the culture medium within this second tank can be the same as, or different from, that used in the first tank.

Once transferred, the microorganisms can be incubated to allow for the production of a C6 building block. Once produced, any method can be used to isolate C6 building blocks. For example, C6 building blocks can be recovered selectively from the fermentation broth via adsorption processes. In the case of adipic acid and 6-aminoheptanoic acid, the resulting eluate can be further concentrated via evaporation, crystallized via evaporative and/or cooling crystallization, and the crystals recovered via centrifugation. In the case of hexamethylenediamine and 1,6-hexanediol, distillation may be employed to achieve the desired product purity.

The invention will be further described in the following examples, which do not limit the scope of the invention described in the claims.

EXAMPLE 1

Enzyme Activity of ω-Transaminase Using Adipate Semialdehyde as Substrate and Forming 6-Aminohexanoate A nucleotide sequence encoding a His-tag was added to the nucleic acid sequences from Chromobacterium violaceum, Pseudomonas aeruginosa, Pseudomonas syringae, Rhodobacter sphaeroides, and Vibrio fluvialis encoding the ω-transaminases of SEQ ID NOs: 7, 8, 9, 10 and 12, respectively (see FIG. 6) such that N-terminal HIS tagged ω-transaminases could be produced. Each of the resulting modified genes was cloned into a pET21a expression vector under control of the T7 promoter and each expression vector was transformed into a BL21[DE3] E. coli host. The resulting recombinant E. coli strains were cultivated at 37° C. in a 250 mL shake flask culture containing 50 mL LB media and antibiotic selection pressure, with shaking at 230 rpm. Each culture was induced overnight at 16° C. using 1 mM IPTG.

The pellet from each induced shake flask culture was harvested via centrifugation. Each pellet was resuspended and lysed via sonication. The cell debris was separated from the supernatant via centrifugation and the cell free extract was used immediately in enzyme activity assays.

Enzyme activity assays in the reverse direction (i.e., 6-aminohexanoate to adipate semialdehyde) were performed in a buffer composed of a final concentration of 50 mM HEPES buffer (pH=7.5), 10 mM 6-aminohexanoate, 10 mM pyruvate and 100 pyridoxyl 5' phosphate. Each enzyme activity assay reaction was initiated by adding cell free extract of the ω-transaminase gene product or the empty vector control to the assay buffer containing the 6-aminohexanoate and incubated at 25° C. for 24 h, with shaking at 250 rpm. The formation of L-alanine from pyruvate was quantified via RP-HPLC.

Figure 11:
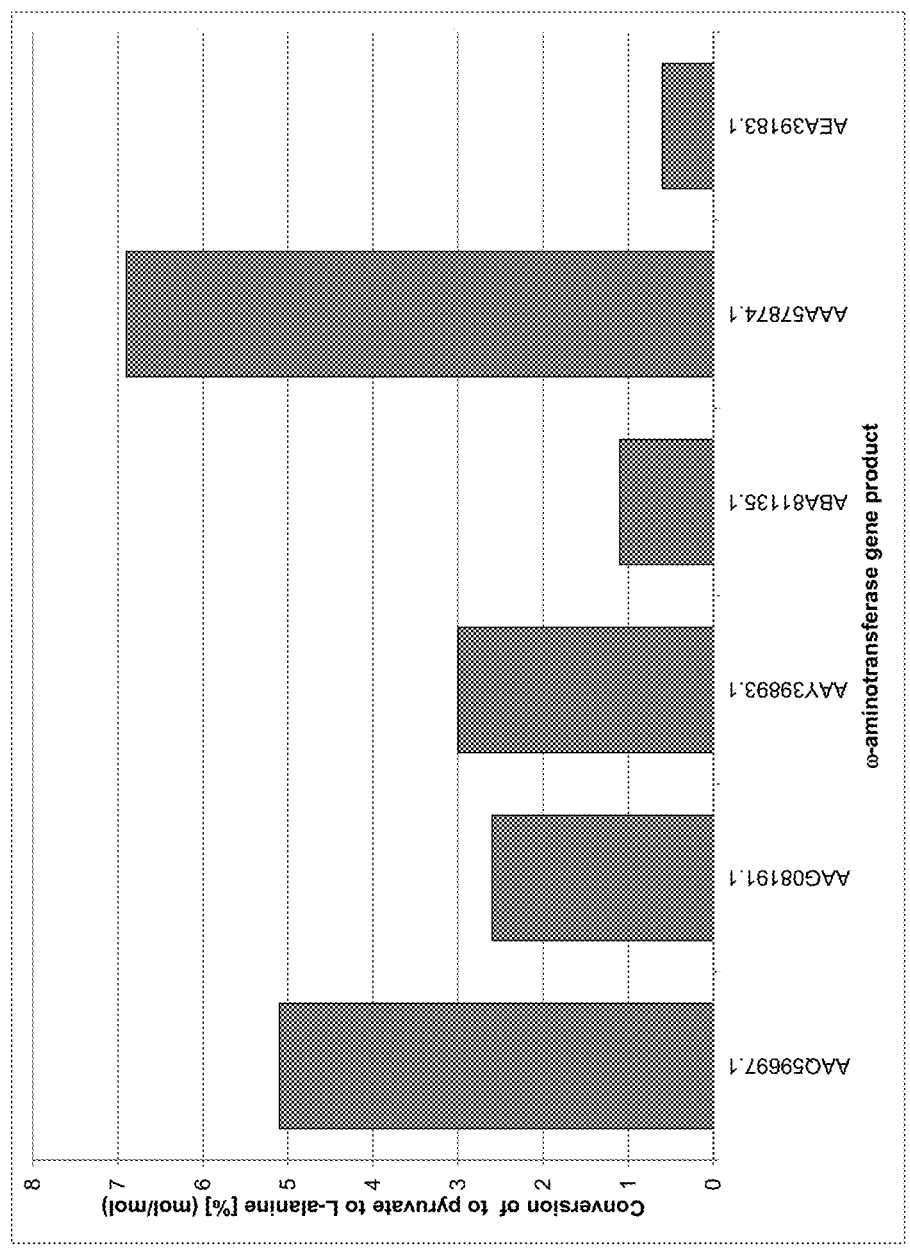
FIG. 11 is a bar graph summarizing the percent conversion after 4 hours of pyruvate to L-alanine (mol/mol) as a measure of the ω-transaminase activity of the enzyme only controls (no substrate).
Figure 12:
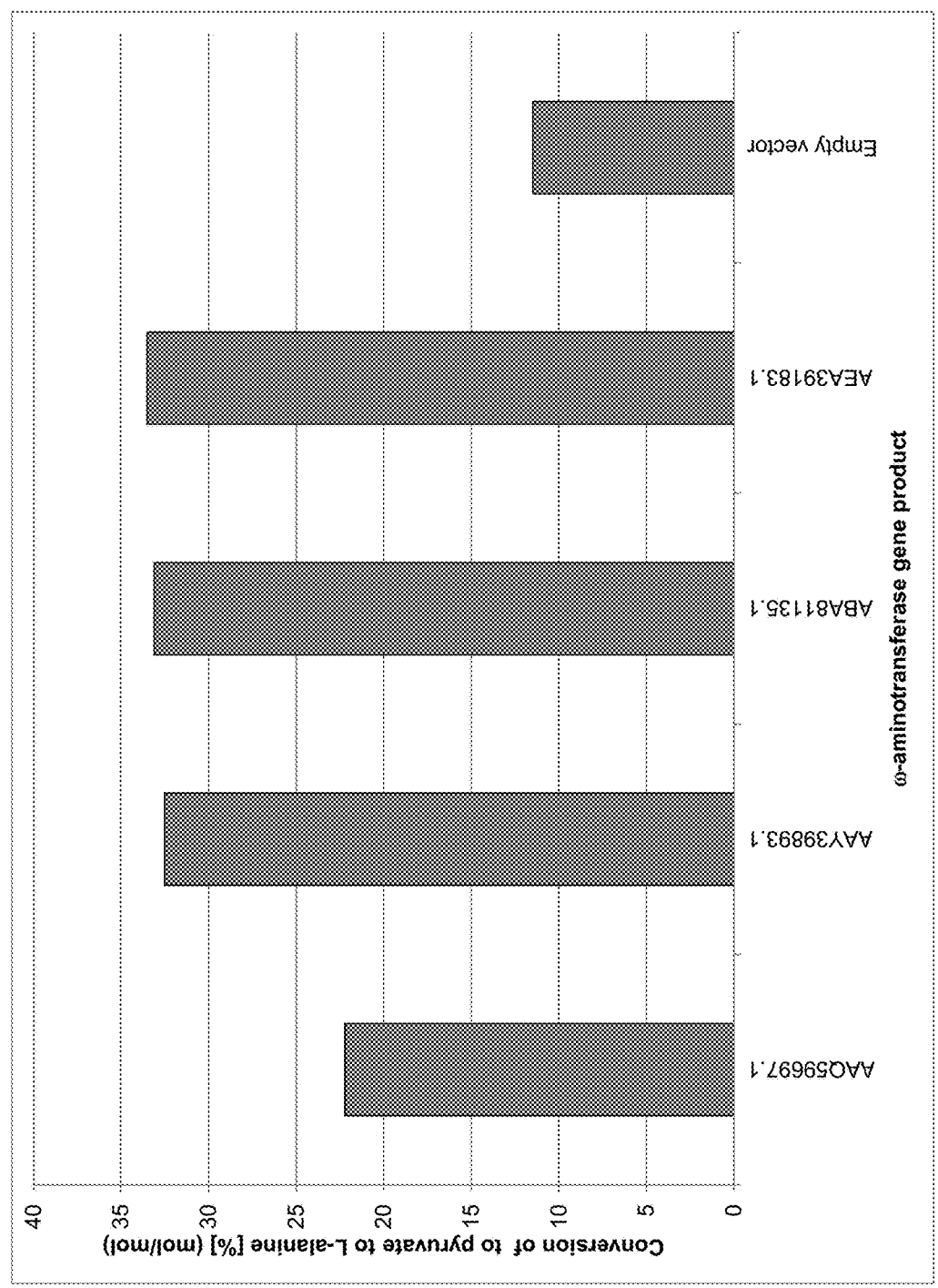
FIG. 12 is a bar graph of the percent conversion after 24 hours of pyruvate to L-alanine (mol/mol) as a measure of the ω-transaminase activity for converting 6-aminohexanoate to adipate semialdehyde relative to the empty vector control.

Each enzyme only control without 6-aminoheptanoate demonstrated low base line conversion of pyruvate to L-alanine. See FIG. 11. The gene product of SEQ ID NO 7, SEQ ID NO 9, SEQ ID NO 10 and SEQ ID NO 12 accepted 6-aminohexanote as substrate as confirmed against the empty vector control. See FIG. 12.

Enzyme activity in the forward direction (i.e., adipate semialdehyde to 6-aminohexanoate) was confirmed for the transaminases of SEQ ID NO 7, SEQ ID NO 8, SEQ ID NO 9, SEQ ID NO 10 and SEQ ID NO 12. Enzyme activity assays were performed in a buffer composed of a final concentration of 50 mM HEPES buffer (pH=7.5), 10 mM adipate semialdehyde, 10 mM L-alanine and 100 μM pyridoxyl 5' phosphate. Each enzyme activity assay reaction was initiated by adding a cell free extract of the ω-transaminase gene product or the empty vector control to the assay buffer containing the adipate semialdehyde and incubated at 25° C. for 4 h, with shaking at 250 rpm. The formation of pyruvate was quantified via RP-HPLC.

Figure 13:
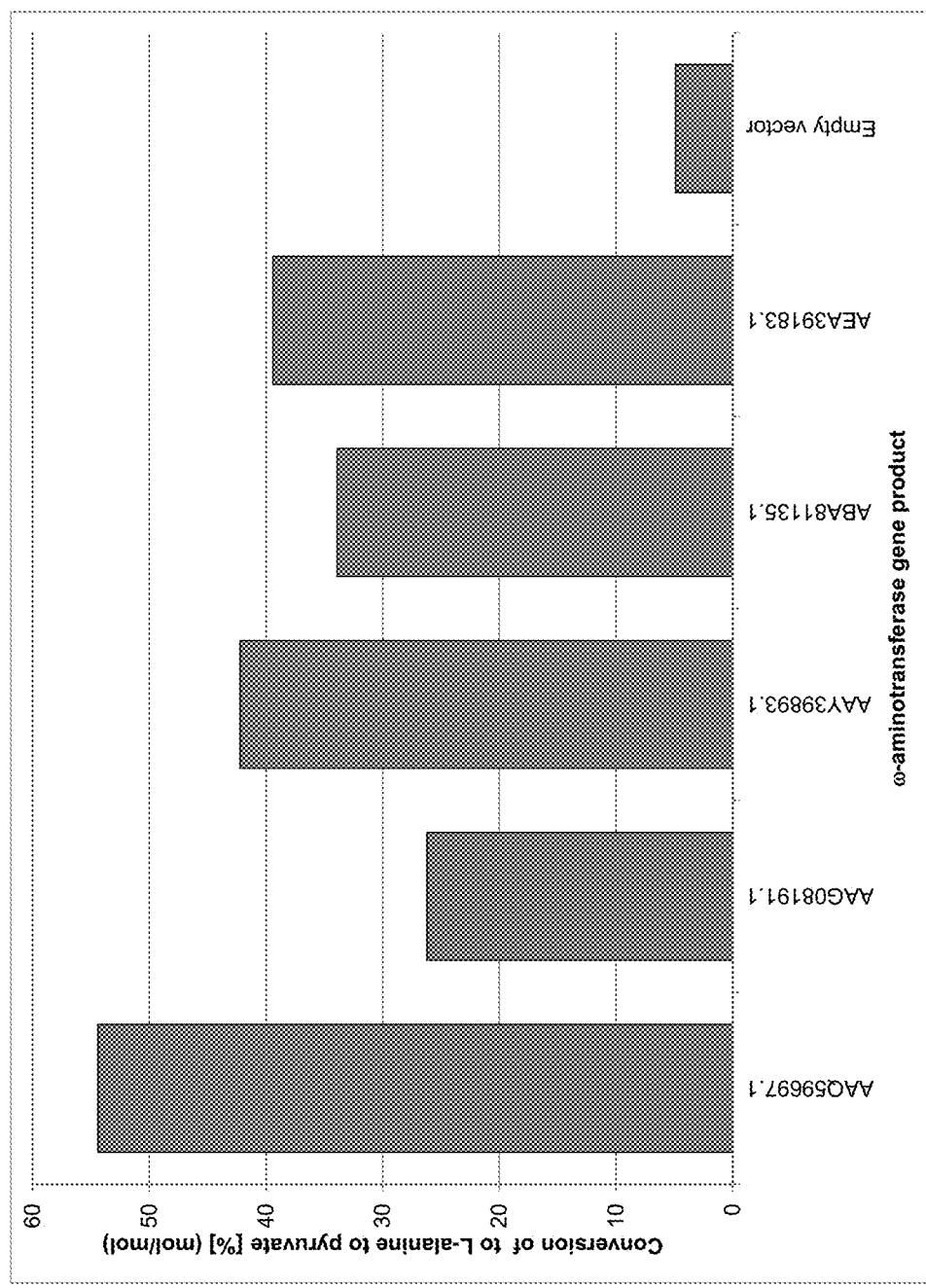
FIG. 13 is a bar graph of the percent conversion after 4 hours of L-alanine to pyruvate (mol/mol) as a measure of the ω-transaminase activity for converting adipate semialdehyde to 6-aminohexanoate relative to the empty vector control.
Figure 14:
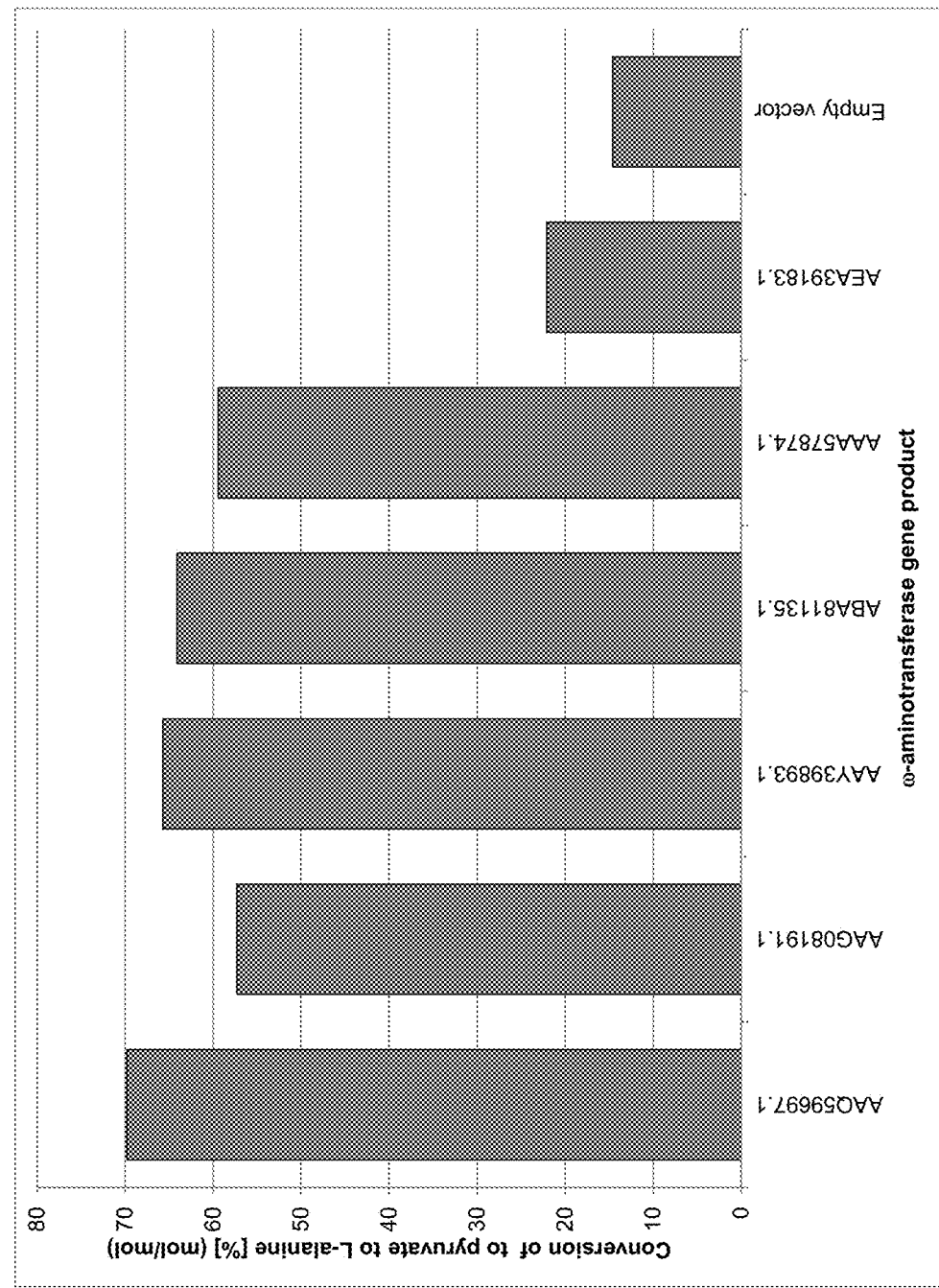
FIG. 14 is a bar graph of the percent conversion after 4 hours of pyruvate to L-alanine (mol/mol) as a measure of the ω-transaminase activity for converting hexamethylenediamine to 6-aminohexanal relative to the empty vector control.

The gene product of SEQ ID NO 7, SEQ ID NO 8, SEQ ID NO 9, SEQ ID NO 10 and SEQ ID NO 12 accepted adipate semialdehyde as substrate as confirmed against the empty vector control. See FIG. 13. The reversibility of the ω-transaminase activity was confirmed, demonstrating that the ω-transaminases of SEQ ID NO 7, SEQ ID NO 8, SEQ ID NO 9, SEQ ID NO 10 and SEQ ID NO 12 accepted adipate semialdehyde as substrate and synthesized 6-aminohexanoate as a reaction product.

EXAMPLE 2

Enzyme Activity of Carboxylate Reductase Using 6-Hydroxyhexanoate as Substrate and Forming 6-Hydroxyhexanal A nucleotide sequence encoding a His-tag was added to the nucleic acid sequences from Mycobacterium marinum, Mycobacterium smegmatis, Mycobacterium smegmatis, Segniliparus rugosus, Mycobacterium massiliense, and Segniliparus rotundus that encode the carboxylate reductases of SEQ ID NOs: 2-6, respectively (see FIG. 6) such that N-terminal HIS tagged carboxylate reductases could be produced. Each of the modified genes was cloned into a pET Duet expression vector alongside a sfp gene encoding a His-tagged phosphopantetheine transferase from Bacillus subtilis, both under control of the T7 promoter. Each expression vector was transformed into a BL21[DE3] E. coli host along with the expression vectors from Example 3. Each resulting recombinant E. coli strain was cultivated at 37° C. in a 250 mL shake flask culture containing 50 mL LB media and antibiotic selection pressure, with shaking at 230 rpm. Each culture was induced overnight at 37° C. using an auto-induction media.

The pellet from each induced shake flask culture was harvested via centrifugation. Each pellet was resuspended and lysed via sonication. The cell debris was separated from the supernatant via centrifugation. The carboxylate reductases and phosphopantetheine transferase were purified from the supernatant using Ni-affinity chromatography, diluted 10-fold into 50 mM HEPES buffer (pH=7.5) and concentrated via ultrafiltration.

Figure 7:
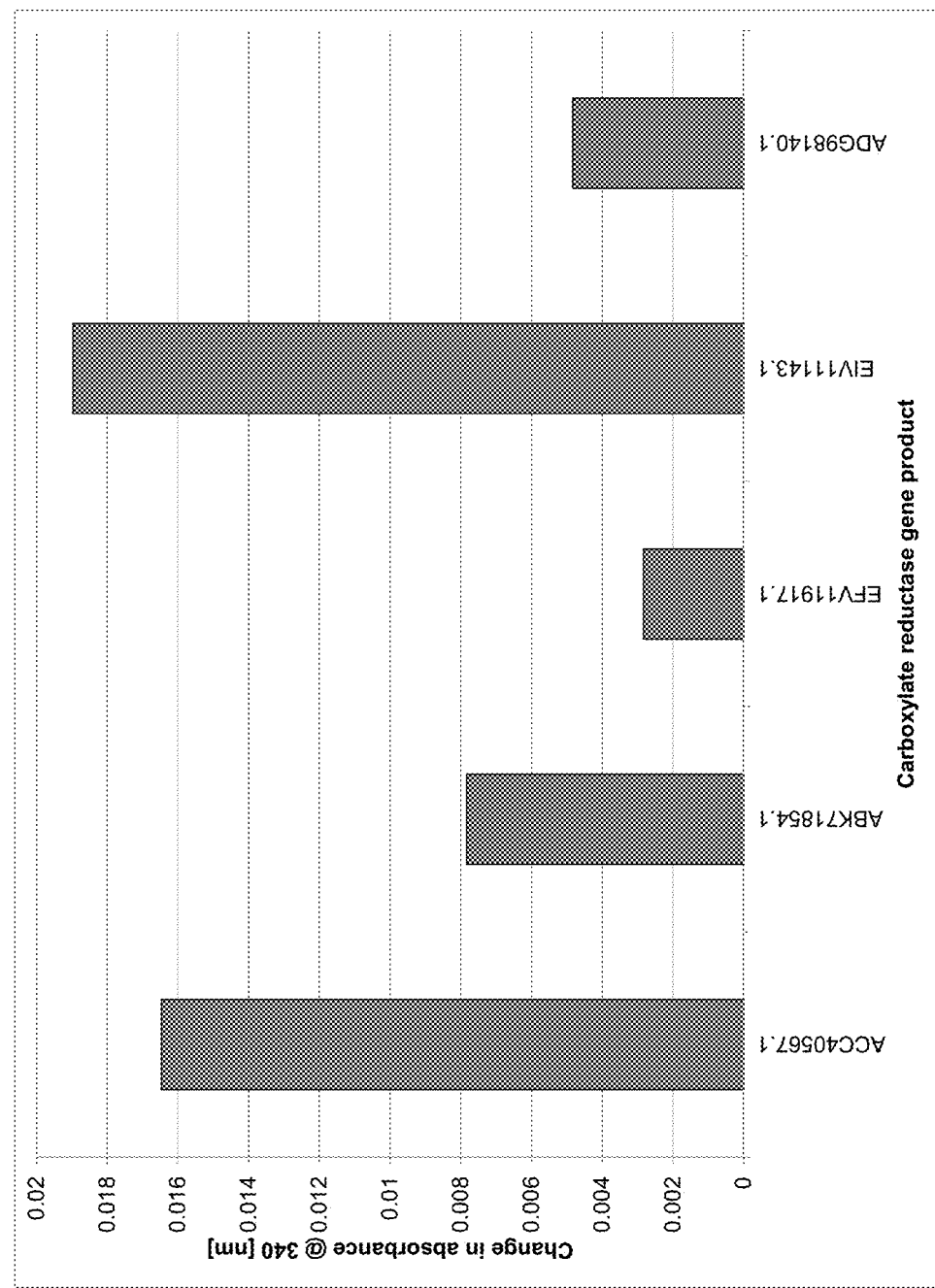
FIG. 7 is a bar graph summarizing the change in absorbance at 340 nm after 20 minutes, which is a measure of the consumption of NADPH and the activity of the carboxylate reductases of the enzyme only controls (no substrate).

Enzyme activity (i.e., 6-hydroxyhexanoate to 6-hydroxyhexanal) assays were performed in triplicate in a buffer composed of a final concentration of 50 mM HEPES buffer (pH=7.5), 2 mM 6-hydroxyhexanal, 10 mM $MgCl_2$, 1 mM ATP, and 1 mM NADPH. Each enzyme activity assay reaction was initiated by adding purified carboxylate reductase and phosphopantetheine transferase or the empty vector control to the assay buffer containing the 6-hydroxyhexanoate and then incubated at room temperature for 20 min. The consumption of NADPH was monitored by absorbance at 340 nm. Each enzyme only control without 6-hydroxyhexanoate demonstrated low base line consumption of NADPH. See FIG. 7.

Figure 8:
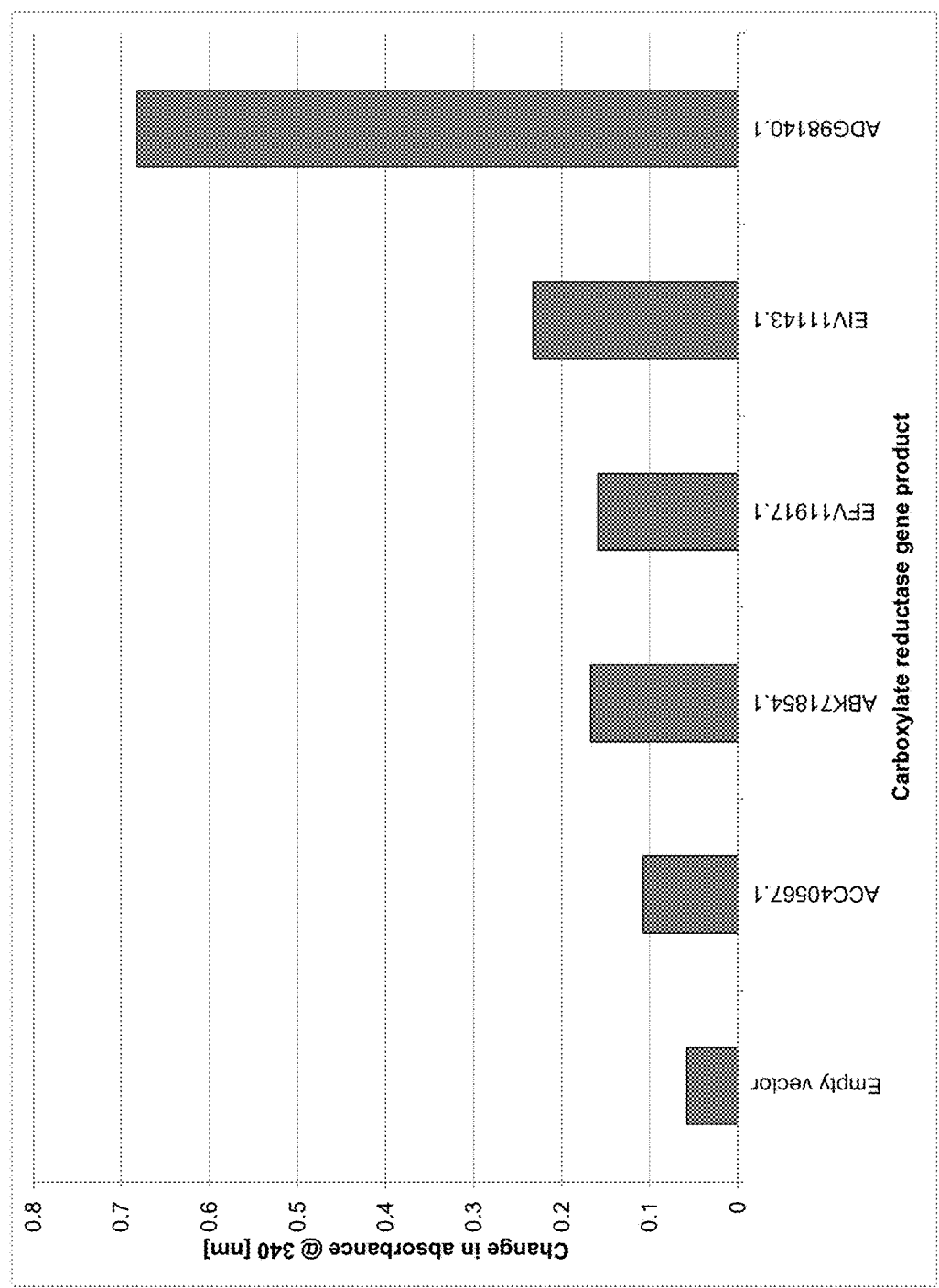
FIG. 8 is a bar graph of the change in absorbance at 340 nm after 20 minutes, which is a measure of the consumption of NADPH and the activity of carboxylate reductases for converting 6-hydroxyhexanoate to 6-hydroxyhexanal relative to the empty vector control.

The gene products of SEQ ID NO 2-6, enhanced by the gene product of sfp, accepted 6-hydroxyhexanoate as substrate as confirmed against the empty vector control (see FIG. 8), and synthesized 6-hydroxyhexanal.

EXAMPLE 3

Enzyme Activity of ω-Transaminase for 6-Aminohexanol, Forming 6-Oxohexanol

A nucleotide sequence encoding an N-terminal His-tag was added to the Chromobacterium *violaceum, Pseudomonas aeruginosa, Pseudomonas syringae, Rhodobacter sphaeroides, Escherichia coli*, and *Vibrio fluvialis* nucleic acid sequences encoding the ω-transaminases of SEQ ID NOs: 7-12, respectively (see FIG. 6) such that N-terminal HIS tagged ω-transaminases could be produced. The modified genes were cloned into a pET21a expression vector under the T7 promoter. Each expression vector was transformed into a BL21[DE3] *E. coli* host. Each resulting recombinant *E. coli* strain were cultivated at 37° C. in a 250 mL shake flask culture containing 50 mL LB media and antibiotic selection pressure, with shaking at 230 rpm. Each culture was induced overnight at 16° C. using 1 mM IPTG.

The pellet from each induced shake flask culture was harvested via centrifugation. Each pellet was resuspended and lysed via sonication. The cell debris was separated from the supernatant via centrifugation and the cell free extract was used immediately in enzyme activity assays.

Enzyme activity assays in the reverse direction (i.e., 6-aminohexanol to 6-oxohexanol) were performed in a buffer composed of a final concentration of 50 mM HEPES buffer (pH=7.5), 10 mM 6-aminohexanol, 10 mM pyruvate, and 100 pyridoxyl 5' phosphate. Each enzyme activity assay reaction was initiated by adding cell free extract of the ω-transaminase gene product or the empty vector control to the assay buffer containing the 6-aminohexanol and then incubated at 25° C. for 4 h, with shaking at 250 rpm. The formation of L-alanine was quantified via RP-HPLC.

Each enzyme only control without 6-aminohexanol had low base line conversion of pyruvate to L-alanine. See FIG. 11.

Figure 16:
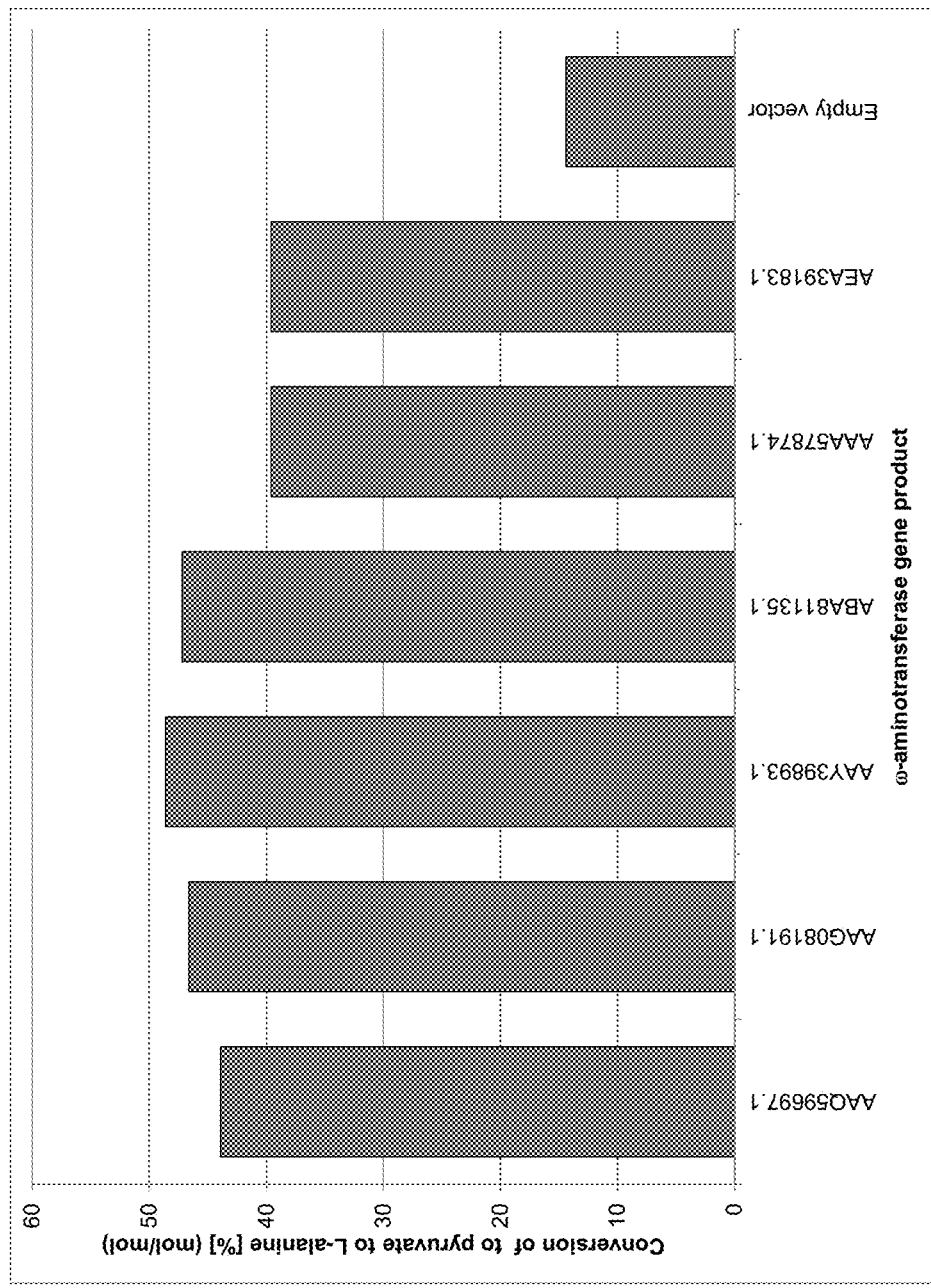
FIG. 16 is a bar graph of the percent conversion after 4 hours of pyruvate to L-alanine (mol/mol) as a measure of the ω-transaminase activity for converting 6-aminohexanol to 6-oxohexanol relative to the empty vector control.

The gene products of SEQ ID NOs: 7-12 accepted 6-aminohexanol as substrate as confirmed against the empty vector control (see FIG. 16) and synthesized 6-oxohexanol (6-hydroxyhexanal) as reaction product. Given the reversibility of the co-transaminase activity (see Example 1), it can be concluded that the gene products of SEQ ID NOs: 7-12 accept 6-aminohexanol as substrate and form 6-oxohexanol.

EXAMPLE 4

Enzyme Activity of ω-Transaminase Using Hexamethylenediamine as Substrate and Forming 6-Aminohexanal A nucleotide sequence encoding an N-terminal His-tag was added to the *Chromobacterium violaceum, Pseudomonas aeruginosa, Pseudomonas syringae, Rhodobacter sphaeroides, Escherichia coli*, and *Vibrio fluvialis* nucleic acid sequences encoding the ω-transaminases of SEQ ID NOs: 7-12, respectively (see FIG. 6) such that N-terminal HIS tagged ω-transaminases could be produced. The modified genes were cloned into a pET21a expression vector under the T7 promoter. Each expression vector was transformed into a BL21 [DE3] *E. coli* host. Each resulting recombinant *E. coli* strain were cultivated at 37° C. in a 250 mL shake flask culture containing 50 mL LB media and antibiotic selection pressure, with shaking at 230 rpm. Each culture was induced overnight at 16° C. using 1 mM IPTG.

The pellet from each induced shake flask culture was harvested via centrifugation. Each pellet was resuspended and lysed via sonication. The cell debris was separated from the supernatant via centrifugation and the cell free extract was used immediately in enzyme activity assays.

Enzyme activity assays in the reverse direction (i.e., hexamethylenediamine to 6-aminohexanal) were performed in a buffer composed of a final concentration of 50 mM HEPES buffer (pH=7.5), 10 mM hexamethylenediamine, 10 mM pyruvate, and 100 pyridoxyl 5' phosphate. Each enzyme activity assay reaction was initiated by adding cell free extract of the ω-transaminase gene product or the empty vector control to the assay buffer containing the hexamethylenediamine and then incubated at 25° C. for 4 h, with shaking at 250 rpm. The formation of L-alanine was quantified via RP-HPLC.

Each enzyme only control without hexamethylenediamine had low base line conversion of pyruvate to L-alanine. See FIG. 11.

The gene products of SEQ ID NO 7-12 accepted hexamethylenediamine as substrate as confirmed against the empty vector control and synthesized 6-aminohexanal as reaction product. Given the reversibility of the ω-transaminase activity (see Example 1), it can be concluded that the gene products of SEQ ID NOs: 7-12 accept 6-aminohexanal as substrate and form hexamethylenediamine.

EXAMPLE 5

Enzyme Activity of Carboxylate Reductase for N6-Acetyl-6-Aminohexanoate, Forming N6-Acetyl-6-Aminohexanal The activity of each of the N-terminal His-tagged carboxylate reductases of SEQ ID NOs: 4-6 (see Example 2, and FIG. 6) for converting N6-acetyl-6-aminohexanoate to N6-acetyl-6-aminohexanal was assayed in triplicate in a buffer composed of a final concentration of 50 mM HEPES buffer (pH=7.5), 2 mM N6-acetyl-6-aminohexanoate, 10 mM $MgCl_2$, 1 mM ATP, and 1 mM NADPH. The assays were initiated by adding purified carboxylate reductase and phosphopantetheine transferase or the empty vector control to the assay buffer containing the N6-acetyl-6-aminohexanoate then incubated at room temperature for 20 min.

The consumption of NADPH was monitored by absorbance at 340 nm. Each enzyme only control without N6-acetyl-6-aminohexanoate demonstrated low base line consumption of NADPH. See FIG. 7.

Figure 9:
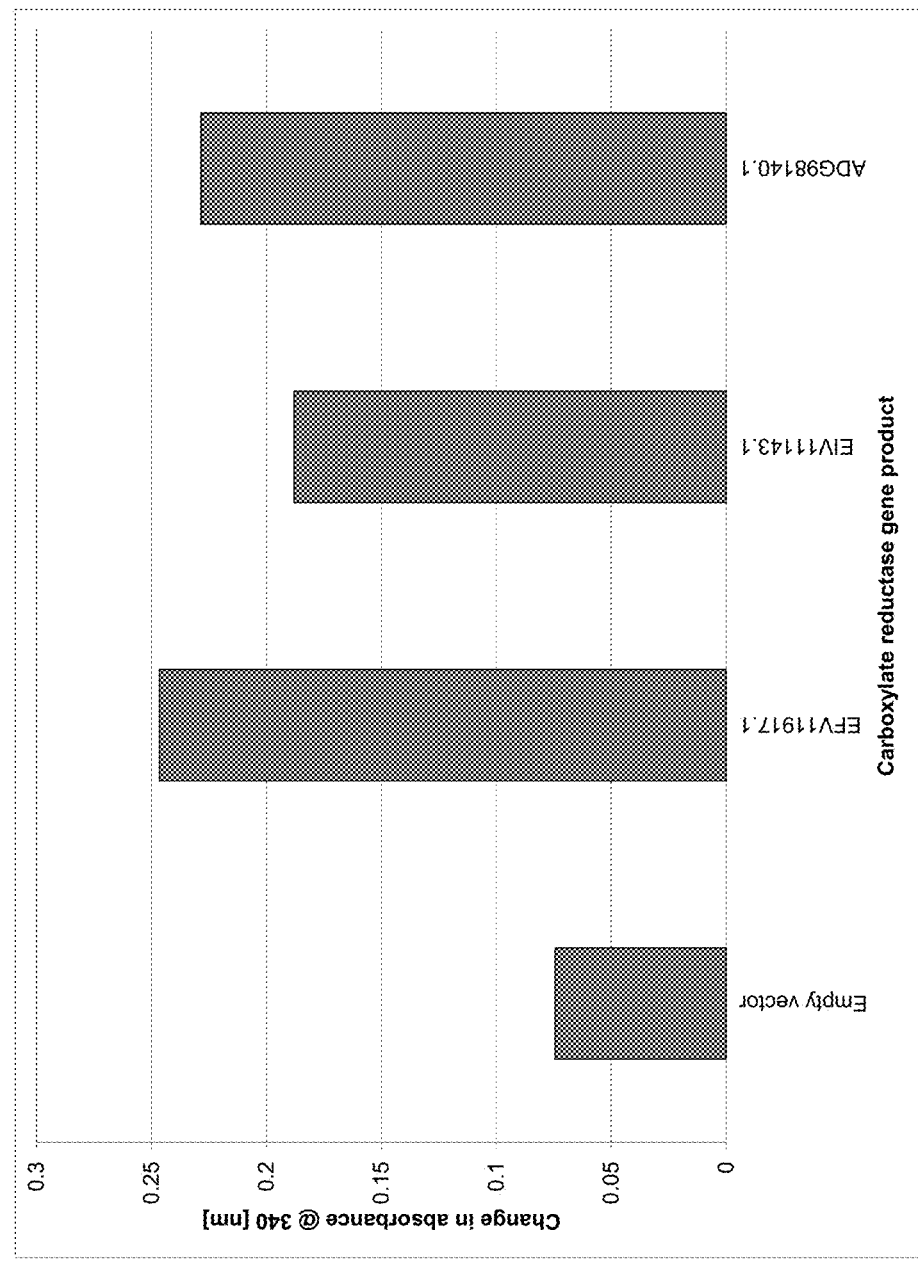
FIG. 9 is a bar graph of the change in absorbance at 340 nm after 20 minutes, which is a measure of the consumption of NADPH and the activity of carboxylate reductases for converting N6-acetyl-6-aminohexanoate to N6-acetyl-6-aminohexanal relative to the empty vector control.

The gene products of SEQ ID NO 4-6, enhanced by the gene product of sfp, accepted N6-acetyl-6-aminohexanoate as substrate as confirmed against the empty vector control (see FIG. 9), and synthesized N6-acetyl-6-aminohexanal.

EXAMPLE 6

Enzyme Activity of ω-Transaminase Using N6-Acetyl-1,6-Diaminohexane, and Forming N6-acetyl-6-aminohexanal The activity of the N-terminal His-tagged ω-transaminases of SEQ ID NOs: 7-12 (see Example 4, and FIG. 6) for converting N6-acetyl-1,6-diaminohexane to N6-acetyl-6-aminohexanal was assayed using a buffer composed of a final concentration of 50 mM HEPES buffer (pH=7.5), 10 mM N6-acetyl-1,6-diaminohexane, 10 mM pyruvate and 100 μM pyridoxyl 5' phosphate. Each enzyme activity assay reaction was initiated by adding a cell free extract of the ω-transaminase or the empty vector control to the assay buffer containing the N6-acetyl-1,6-diaminohexane then incubated at 25° C. for 4 h, with shaking at 250 rpm. The formation of L-alanine was quantified via RP-HPLC.

Each enzyme only control without N6-acetyl-1,6-diaminohexane demonstrated low base line conversion of pyruvate to L-alanine. See FIG. 11.

Figure 15:
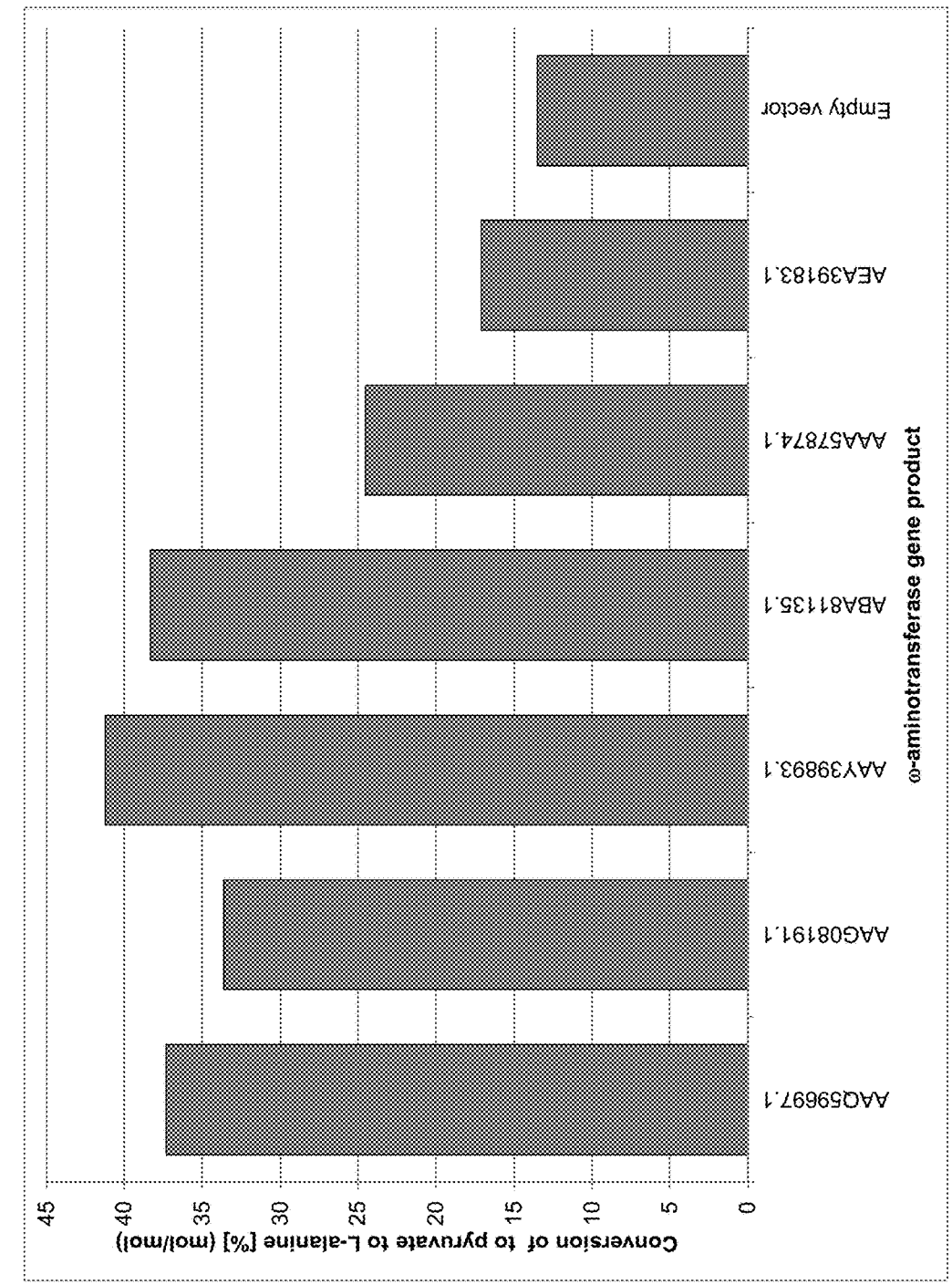
FIG. 15 is a bar graph of the percent conversion after 4 hours of pyruvate to L-alanine (mol/mol) as a measure of the ω-transaminase activity for converting N6-acetyl-1,6-diaminohexane to N6-acetyl-6-aminohexanal relative to the empty vector control.

The gene product of SEQ ID NO 7-12 accepted N6-acetyl-1,6-diaminohexane as substrate as confirmed against the empty vector control (see FIG. 15) and synthesized N6-acetyl-6-aminohexanal as reaction product.

Given the reversibility of the ω-transaminase activity (see example 1), the gene products of SEQ ID NOs: 7-12 accept N6-acetyl-6-aminohexanal as substrate forming N6-acetyl-1,6-diaminohexane.

EXAMPLE 7

Enzyme Activity of Carboxylate Reductase Using Adipate Semialdehyde as Substrate and Forming Hexanedial The N-terminal His-tagged carboxylate reductase of SEQ ID NO 6 (see Example 2 and FIG. 6) was assayed using adipate semialdehyde as substrate. The enzyme activity assay was performed in triplicate in a buffer composed of a final concentration of 50 mM HEPES buffer (pH=7.5), 2 mM adipate semialdehyde, 10 mM MgCl$_2$, 1 mM ATP and 1 mM NADPH. The enzyme activity assay reaction was initiated by adding purified carboxylate reductase and phosphopantetheine transferase or the empty vector control to the assay buffer containing the adipate semialdehyde and then incubated at room temperature for 20 min. The consumption of NADPH was monitored by absorbance at 340 nm. The enzyme only control without adipate semialdehyde demonstrated low base line consumption of NADPH. See FIG. 7.

Figure 10:
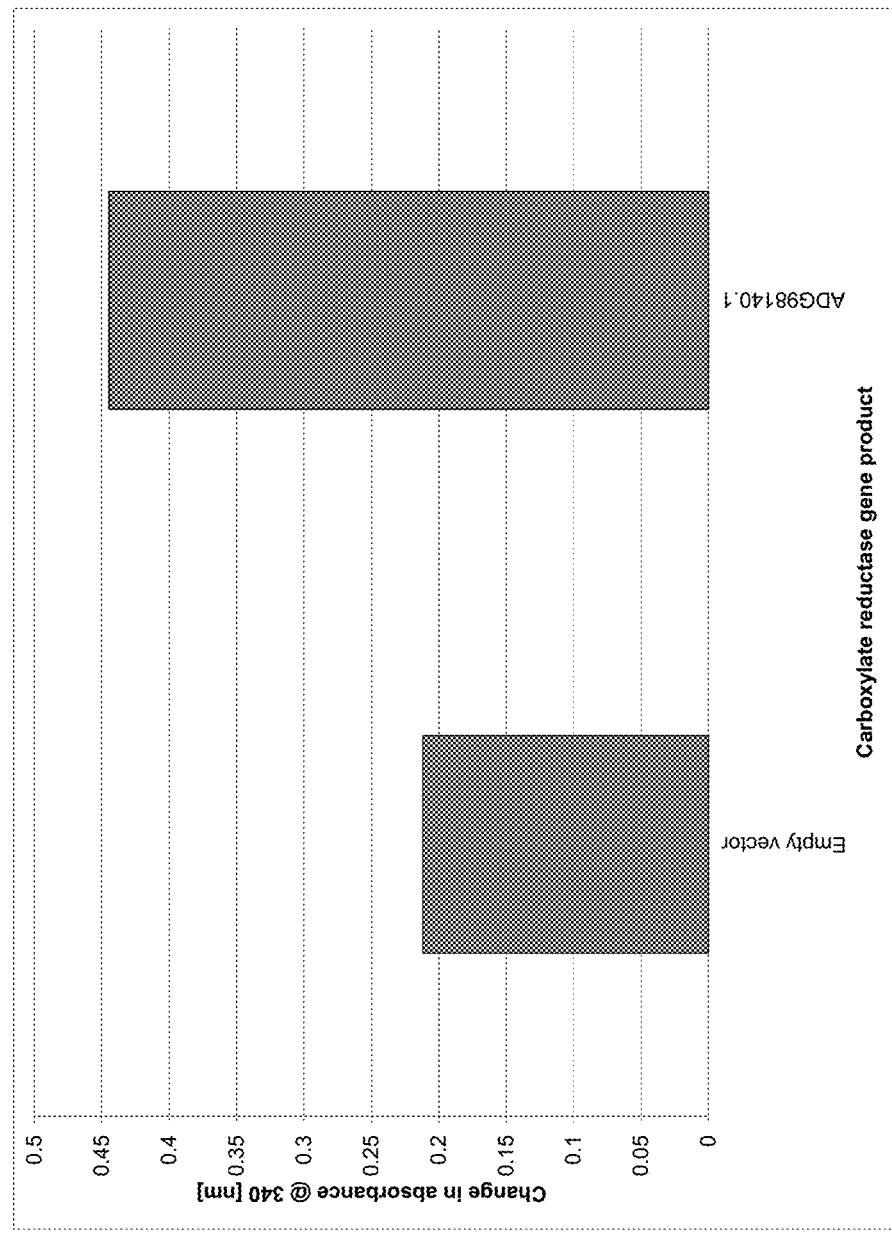
FIG. 10 is a bar graph of the change in absorbance at 340 nm after 20 minutes, which is a measure of the consumption of NADPH and activity of carboxylate reductases for converting adipate semialdehyde to hexanedial relative to the empty vector control.

The gene product of SEQ ID NO: 6, enhanced by the gene product of sfp, accepted adipate semialdehyde as substrate as confirmed against the empty vector control (see FIG. 10) and synthesized hexanedial.

EXAMPLE 8

Enzyme Activity of Enoyl-CoA Reductase Using 6-Acetyloxy-Hex-2-Enoyl-CoA as Substrate and Forming 6-Acetyloxy-Hexanoyl-CoA A nucleotide sequence encoding a His-tag was added to the nucleic acid sequences of *Treponema denticola, Euglena gracilis, Sphaerochaeta pleomorpha, Burkholderia mallei, Xanthomonas oryzae* pv. *oryzae* and *Flavobacterium johnsoniae* encoding the enoyl-CoA reductases of SEQ ID NOs: 23-28, respectively (see FIG. 6), such that HIS-tagged enoyl-CoA reductases could be produced. The modified genes were cloned into an expression vector and each expression vector was transformed into a BL21-AI *E. coli* host. One colony of each transformant was picked and inoculated individually into 5 mL of Luria Broth (LB) media with antibiotic selection pressure and cultivated overnight at 37° C. and 230 rpm. An inoculum of 0.1% (v/v) from each overnight preculture was used to inoculate 100 mL of LB media with antibiotic selection pressure in a 500 mL shake, cultivating at 37° C. and 230 rpm to an OD$_{600}$~0.9. Each culture was cooled to 17° C., induced and further incubated for 20 h.

The pellet from each induced shake flask culture was harvested via centrifugation. Each pellet was resuspended and lysed via sonication. The enoyl-CoA reductases were purified from the supernatant using Ni-affinity chromatography, buffer exchanged and concentrated via ultrafiltration into a buffer comprised of 50 mM HEPES (pH=7.5), 150 mM NaCl and 5% (w/v) glycerol.

Enzyme activity assays (i.e., 6-acetyloxy-hex-2-enoyl-CoA to 6-acetyloxy-hexanoyl-CoA) were performed in duplicate in a buffer composed of a final concentration of 50 mM HEPES buffer (pH=7.0), 1.3 mM NADH, 1.3 mM NADPH and 0.6-0.8 mM of 6-acetyloxy-hex-2-enoyl-CoA. Each enzyme activity assay reaction was initiated by adding 4-10 μM purified enoyl-CoA reductase or the empty vector control to the assay buffer containing 6-acetyloxy-hex-2-enoyl-CoA and then incubated at 37° C. for 8 h.

Figure 17:
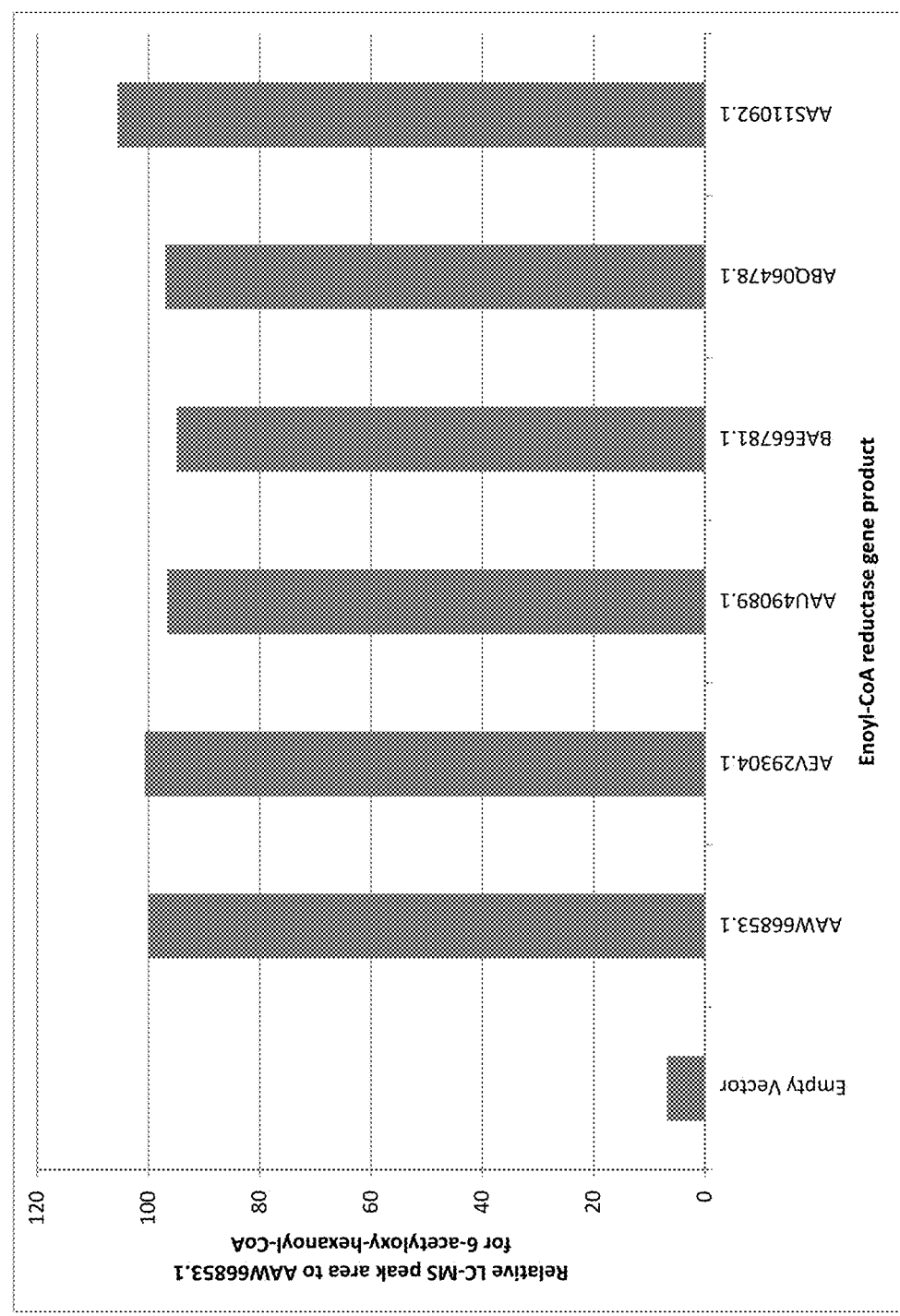
FIG. 17 is a bar graph of the relative LC-MS peak area to AAW66853.1 for 6-acetyloxy-hexanoyl-CoA after 15-20 hours incubation with 6-acetyloxy-hex-2-enoyl-CoA as a measure of the enoyl-CoA reductase activity in relation to the empty vector control.

Sample analysis entailed LC-MS analysis for the reaction product 6-acetyloxy-hexanoyl-CoA. FIG. 17 shows the relative LC-MS peak area for 6-acetyloxy-hexanoyl-CoA to that obtained using SEQ ID NO: 24, demonstrating that SEQ ID NO: 23-28 converted 6-acetyloxy-hex-2-enoyl-CoA to 6-acetyloxy-hexanoyl-CoA as compared to the empty vector control. Enzyme only control samples without the substrate 6-acetyloxy-hex-2-enoyl-CoA had no discernable peak area for 6-acetyloxy-hexanoyl-CoA.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of producing 6-acetyloxy-3-oxohexanoyl-CoA, said method comprising enzymatically converting 4-acetyloxybutyryl-CoA to 6-acetyloxy-3-oxohexanoyl-CoA using a polypeptide having the activity of a β-ketothiolase or synthase classified under EC 2.3.1.16, EC 2.3.1.41, EC 2.3.1.174, EC 2.3.1.179, or EC 2.3.1.180.

2. The method of claim 1, wherein said polypeptide having the activity of a β-ketothiolase has at least 90% sequence identity to the amino acid sequence set forth in SEQ ID NO:1 or SEQ ID NO:16.

3. The method of claim 1, further comprising enzymatically converting 6-acetyloxy-3-oxohexanoyl-CoA to 6-hydroxyhexanoate using a polypeptide having the activity of a 3-hydroxyacyl-CoA dehydrogenase classified under EC 1.1.1.35, EC 1.1.1.36, or EC 1.1.1.157 ora 3-oxoacyl-CoA reductase classified under EC 1.1.1.100, a polypeptide having the activity of an enoyl-CoA hydratase classified under EC 4.2.1.17 or EC 4.2.1.119, a polypeptide having the activity of a trans-2-enoyl-CoA reductase classified under EC 1.3.1.38, EC 1.3.1.44, or EC 1.3.1.8, a polypeptide having the activity of an esterase classified under EC 3.1.1.1, EC 3.1.1.6, or EC 3.1.1.85, and a polypeptide having the activity of a thioesterase classified under EC 3.1.2.- or a CoA transferase classified under EC 2.8.3-.

4. The method of claim 3, wherein
said polypeptide having the activity of a trans-2-enoyl-CoA reductase classified under EC 1.3.1.38, EC 1.3.1.44, or EC 1.3.1.8 has at least 90% sequence identity to the amino acid sequence set forth in any one of SEQ ID NOs:23-28; and/or
said polypeptide having the activity of an esterase classified under EC 3.1.1.1, EC 3.1.1.6, or EC 3.1.1.85 has at least 90% sequence identity to the amino acid sequence set forth in SEQ ID NO:15 or SEQ ID NO:18.

5. The method of claim 1, wherein 4-acetyloxybutyryl-CoA is enzymatically synthesized from 4-hydroxybutyryl-CoA using:
(a) a polypeptide having the activity of an alcohol-O-acetyltransferase classified under EC 2.3.1.84; or
(b) (i) a polypeptide having the activity of an alcohol-O-acetyltransferase classified under EC 2.3.1.84, and (ii)

a polypeptide having the activity of a CoA transferase classified under EC 2.8.3.- or a CoA ligase classified under EC 6.2.1-.

6. The method of claim 5, wherein said polypeptide having the activity of an alcohol-O-acetyltransferase classified under EC 2.3.1.84 has at least 90% sequence identity to the amino acid sequence set forth in SEQ ID NO: 17.

7. A method for biosynthesizing 6-hydroxyhexanoate, said method comprising enzymatically synthesizing 6-acetyloxy-3-oxohexanoyl-CoA from 4-acetyloxybutyryl-CoA using a polypeptide having the activity of a β-ketothiolase or synthase classified under EC 2.3.1.16, EC 2.3.1.41, EC 2.3.1.174, EC 2.3.1.179, or EC 2.3.1.180 and enzymatically converting 6-acetyloxy-3-oxohexanoyl-CoA to 6-hydroxyhexanoate.

8. The method of claim 7, wherein 6-acetyloxy-3-oxohexanoyl-CoA is converted to 6-acetyloxy-3-hydroxyhexanoyl-CoA using a polypeptide having the activity of a 3-hydroxyacyl-CoA dehydrogenase classified under EC 1.1.1.35, EC 1.1.1.36, or EC 1.1.1.157 or a 3-oxoacyl-CoA reductase classified under EC 1.1.1.100, 6-acetyloxy-3-hydroxyhexanoyl-CoA is converted to 6-acetyloxy-hex-2-enoyl-CoA using a polypeptide having the activity of an enoyl-CoA hydratase classified under EC 4.2.1.17 or EC 4.2.1.119, 6-acetyloxy-hex-2-enoyl-CoA is converted to 6-acetyloxyhexanoyl-CoA using a polypeptide having the activity of a trans-2-enoyl-CoA reductase classified under EC 1.3.1.38, EC 1.3.1.44, or EC 1.3.1.8, 6-acetyloxyhexanoyl-CoA is converted to 6-acetyloxyhexanoic acid using a polypeptide having the activity of a thioesterase classified under EC 3.1.2.- or a CoA transferase classified under EC 2.8.3-, and 6-acetyloxyhexanoic acid is converted to 6-hydroxyhexanoic acid using a polypeptide having the activity of an esterase classified under EC 3.1.1.1 or EC 3.1.1.6; or wherein 6-acetyloxy-3-oxohexanoyl-CoA is converted to 6-acetyloxy-3-hydroxyhexanoyl-CoA using a polypeptide having the activity of a 3-hydroxyacyl-CoA dehydrogenase classified under EC 1.1.1.35, EC 1.1.1.36, or EC 1.1.1.157 or a 3-oxoacyl-CoA reductase classified under EC 1.1.1.100, 6-acetyloxy-3-hydroxyhexanoyl-CoA is converted to 6-acetyloxy-hex-2-enoyl-CoA using a polypeptide having the activity of an enoyl-CoA hydratase classified under EC 4.2.1.17 or EC 4.2.1.119, 6-acetyloxy-hex-2-enoyl-CoA is converted to 6-acetyloxyhexanoyl-CoA using a polypeptide having the activity of a trans-2-enoyl-CoA reductase classified under EC 1.3.1.38, EC 1.3.1.44, or EC 1.3.1.8, 6-acetyloxyhexanoyl-CoA is converted to 6-hydroxyhexanoyl-CoA using a polypeptide having the activity of an esterase classified under EC 3.1.1.85, and 6-hydroxyhexanoyl-CoA is converted to 6-hydroxyhexanoic acid using a polypeptide having the activity of a thioesterase classified under EC 3.1.2.- or a CoA transferase classified under EC 2.8.3-.

9. The method of claim 3 or claim 7, said method further comprising enzymatically converting 6-hydroxyhexanoate to adipic acid, 6-aminohexanoate, caprolactam, hexamethylenediamine, or 1,6-hexanediol in one or more steps.

10. The method of claim 9, wherein:
(a) 6-hydroxyhexanoate is converted to adipic acid using one or more of a polypeptide having the activity of a monooxygenase in the cytochrome P450 family, a polypeptide having the activity of an alcohol dehydrogenase classified under EC 1.1.1.-, a polypeptide having the activity of a 4-hydroxybutanoate dehydrogenase classified under EC 1.1.1.-, a polypeptide having the activity of a 5-hydroxyvalerate dehydrogenase classified under EC 1.1.1.-, a polypeptide having the activity of a 6-hydroxyhexanoate dehydrogenase classified under EC 1.1.1.258, a polypeptide having the activity of a 7-oxoheptanoate dehydrogenase classified under EC 1.2.1.-, a polypeptide having the activity of a 6-oxohexanoate dehydrogenase classified under EC 1.2.1.-, a polypeptide having the activity of a 5-oxovalerate dehydrogenase classified under EC 1.2.1.-, or a polypeptide having the activity of an aldehyde dehydrogenase classified under EC 1.2.1.3;

(b) 6-hydroxyhexanoate is converted to 6-aminohexanoate using one or more of a polypeptide having the activity of an alcohol dehydrogenase classified under EC 1.1.1.2, a polypeptide having the activity of a 6-hydroxyhexanoate dehydrogenase classified under EC 1.1.1.258, a polypeptide having the activity of a 5-hydroxypentanoate dehydrogenase classified under EC 1.1.1.-, a polypeptide having the activity of a 4-hydroxybutyrate dehydrogenase classified under EC 1.1.1.-, or a polypeptide having the activity of a ω-transaminase classified under EC 2.6.1.18, EC 2.6.1.19, EC 2.6.1.29, EC 2.6.1.48, or EC 2.6.1.82;

(c) 6-hydroxyhexanoate is converted to caprolactam using one or more of a polypeptide having the activity of an alcohol dehydrogenase classified under EC 1.1.1.2, a polypeptide having the activity of a 6-hydroxyhexanoate dehydrogenase classified under EC 1.1.1.258, a polypeptide having the activity of a 5-hydroxypentanoate dehydrogenase classified under EC 1.1.1.-, a polypeptide having the activity of a 4-hydroxybutyrate dehydrogenase classified under EC 1.1.1.-, a polypeptide having the activity of a ω-transaminase classified under EC 2.6.1.18, EC 2.6.1.19, EC 2.6.1.29, EC 2.6.1.48, or EC 2.6.1.82, or a polypeptide having the activity of an amidohydrolase classified under EC 3.5.2.-;

(d) 6-hydroxyhexanoate is converted to hexamethylenediamine using one or more of a polypeptide having the activity of a carboxylate reductase classified under EC 1.2.99.6, a polypeptide having the activity of a ω-transaminase classified under EC 2.6.1.18, EC 2.6.1.19, EC 2.6.1.29, EC 2.6.1.48, or EC 2.6.1.82, a polypeptide having the activity of an alcohol dehydrogenase classified under EC 1.1.1.1, EC 1.1.1.2, EC 1.1.1.21, or EC 1.1.1.184, a polypeptide having the activity of an N-acetyltransferase classified under EC 2.3.1.32, or a polypeptide having the activity of an acyl lysine deacylase classified under EC 3.5.1.17; and/or (e) 6-hydroxyhexanoate is converted to 1,6-hexanediol using a polypeptide having the activity of a carboxylate reductase classified under EC 1.2.99.6 and a polypeptide having the activity of an alcohol dehydrogenase classified under EC 1.1.1.1, EC 1.1.1.2, EC 1.1.1.21, or EC 1.1.1.184.

11. The method of claim 10, wherein:
(a) said polypeptide having the activity of a ω-transaminase classified under EC 2.6.1.18, EC 2.6.1.19, EC 2.6.1.29, EC 2.6.1.48, or EC 2.6.1.82 has at least 90% sequence identity to the amino acid sequence set forth in any one of SEQ ID NOs:7-12; and/or (b) said polypeptide having the activity of a carboxylate reductase classified under EC 1.2.99.6 has at least 90% sequence identity to the amino acid sequence set forth in any one of SEQ ID NOs:2-6.

12. The method of claim 1 or claim 7, wherein said 4-acetyloxybutyryl-CoA is enzymatically produced from 2-oxoglutarate.

13. The method of claim 12, wherein 4-acetyloxybutyryl-CoA is enzymatically produced from 2-oxoglutarate using one or more of a polypeptide having the activity of a glutamate synthase classified under EC 1.4.1.13, a polypeptide having the activity of a 2-oxoglutarate decarboxylase classified under EC 4.1.1.71, a polypeptide having the activity of a branch chain decarboxylase classified under EC 4.1.1.72, a polypeptide having the activity of a phenylpyruvate decarboxylase classified under EC 4.1.1.43, a polypeptide having the activity of a indolepyruvate decarboxylase classified under EC 4.1.1.74, a polypeptide having the activity of a glutamate decarboxylase classified under EC 4.1.1.15 or EC 4.1.1.18, a polypeptide having the activity of a ω-transaminase classified under EC 2.6.1.18, EC 2.6.1.19, EC 2.6.1.48, or EC 2.6.1.96, a polypeptide having the activity of a CoA transferase classified under EC 2.8.3.-, a polypeptide having the activity of a CoA ligase classified under EC 6.2.1-, a polypeptide having the activity of an alcohol-O-acetyltransferase classified under EC 2.3.1.84, or a polypeptide having the activity of an alcohol dehydrogenase classified under EC 1.1.1.61.

14. The method of claim 1 or claim 7, wherein said method is performed in a recombinant host.

15. The method of claim 14, wherein:
(a) said recombinant host is subjected to a cultivation strategy under aerobic, anaerobic, or micro-aerobic cultivation conditions;
(b) said recombinant host is cultured under conditions of nutrient limitation;
(c) said method is performed by fermentation, and said recombinant host is retained using a ceramic membrane to maintain a high cell density during the fermentation;
(d) said method is performed by fermentation, and the principal carbon source fed to the fermentation derives from a biological feedstock; and/or
(e) said method is performed by fermentation, and the principal carbon source fed to the fermentation derives from a non-biological feedstock.

16. The method of claim 15, wherein:
(a) the biological feedstock is, or derives from, monosaccharides, disaccharides, lignocellulose, hemicellulose, cellulose, lignin, levulinic acid, formic acid, triglycerides, glycerol, fatty acids, agricultural waste, condensed distillers' solubles, or municipal waste; or
(b) the non-biological feedstock is, or derives from, natural gas, syngas, $CO_2/H_2$, methanol, ethanol, benzoate, non-volatile residue (NVR) caustic wash waste stream from cyclohexane oxidation processes, or terephthalic acid/isophthalic acid mixture waste streams.

17. The method of claim 14, wherein the recombinant host is a prokaryote or a eukaryote.

18. The method of claim 17, wherein:
(a) said prokaryote is from a genus selected from the group consisting of *Escherichia, Clostridia, Corynebacteria, Cupriavidus, Pseudomonas, Delftia, Bacilluss, Lactobacillus, Lactococcus*, and *Rhodococcus*; or
(b) said eukaryote is from a genus selected from the group consisting of *Aspergillus, Saccharomyces, Pichia, Yarrowia, Issatchenkia, Debaryomyces, Arxula*, and *Kluyveromyces*.

19. The method of claim 18, wherein:
(a) said prokaryote is selected from the group consisting of *Escherichia coli, Clostridium ljungdahlii, Clostridium autoethanogenum, Clostridium kluyveri, Corynebacterium glutamicum, Cupriavidus necator, Cupriavidus metallidurans, Pseudomonas fluorescens, Pseudomonas putida, Pseudomonas oleavorans, Delftia acidovorans, Bacillus subtillis, Lactobacillus delbrueckii, Lactococcus lactis*, and *Rhodococcus equi*; or
(b) said eukaryote is selected from the group consisting of *Aspergillus niger, Saccharomyces cerevisiae, Pichia pastoris, Yarrowia lipolytica, Issathenkia orientalis, Debaryomyces hansenii, Arxula adenoinivorans*, and *Kluyveromyces lactis*.

20. The method of claim 14, wherein:
(a) the recombinant host's tolerance to high concentrations of a C6 building block is improved through continuous cultivation in a selective environment;
(b) said recombinant host comprises an attenuation to one or more polypeptides having the activity of the following enzymes: a polyhydroxyalkanoate synthase, an acetyl-CoA thioesterase, a phosphotransacetylase forming acetate, an acetate kinase, a lactate dehydrogenase, a menaquinol-fumarate oxidoreductase, an alcohol dehydrogenase forming ethanol, a triose phosphate isomerase, a pyruvate decarboxylase, a glucose-6-phosphate isomerase, an NADH-consuming transhydrogenase, an NADH-specific glutamate dehydrogenase, an NADH/NADPH-utilizing glutamate dehydrogenase, a pimeloyl-CoA dehydrogenase, an acyl-CoA dehydrogenase accepting C6 building blocks and central precursors as substrates, a butaryl-CoA dehydrogenase, or an adipyl-CoA synthetase; and/or
(c) said recombinant host overexpresses one or more genes encoding polypeptides having the activity of the following enzymes: an acetyl-CoA synthetase, a 6-phosphogluconate dehydrogenase, a transketolase, a puridine nucleotide transhydrogenase, a glyceraldehyde-3P-dehydrogenase, a malic enzyme, a glucose-6-phosphate dehydrogenase, a glucose dehydrogenase, a fructose 1,6 diphosphatase, a L-alanine dehydrogenase, a L-glutamate dehydrogenase, a formate dehydrogenase, a L-glutamine synthetase, a diamine transporter, a dicarboxylate transporter, and/or a multidrug transporter.

21. A method of producing 6-acetyloxy-3-oxohexanoyl-CoA, comprising contacting 4-acetyloxybutyryl-CoA with a means for enzymatically converting the 4-acetyloxybutyryl-CoA to 6-acetyloxy-3-oxohexanoyl-CoA.

22. The method of claim 21, wherein said means for enzymatically converting 4-acetyloxybutyryl-CoA to 6-acetyloxy-3-oxohexanoyl-CoA comprises a polypeptide having the activity of a β-ketothiolase or synthase classified under EC 2.3.1.16, EC 2.3.1.41, EC 2.3.1.174, EC 2.3.1.179, or EC 2.3.1.180.

23. The method of claim 21, further comprising providing a means for enzymatically converting 6-acetyloxy-3-oxohexanoyl-CoA to 6-hydroxyhexanoate.

24. The method of claim 23, wherein said means for enzymatically converting 6-acetyloxy-3-oxohexanoyl-CoA to 6-hydroxyhexanoate comprises a polypeptide having the activity of a 3-hydroxyacyl-CoA dehydrogenase classified under EC 1.1.1.35, EC 1.1.1.36, or EC 1.1.1.157 or a 3-oxoacyl-CoA reductase classified under EC 1.1.1.100, a polypeptide having the activity of an enoyl-CoA hydratase classified under EC 4.2.1.17 or EC 4.2.1.119, a polypeptide having the activity of a trans-2-enoyl-CoA reductase classified under EC 1.3.1.38, EC 1.3.1.44, or EC 1.3.1.8, a polypeptide having the activity of an esterase classified under EC 3.1.1.1, EC 3.1.1.6, or EC 3.1.1.85, and a polypeptide having the activity of a thioesterase classified under EC 3.1.2.- or a CoA transferase classified under EC 2.8.3-.

25. A method for obtaining 6-acetyloxy-3-oxohexanoyl-CoA, comprising a step for enzymatically converting 4-acetyloxybutyryl-CoA to 6-acetyloxy-3-oxohexanoyl-CoA.

26. The method of claim 25, wherein the step comprises using a polypeptide having the activity of a β-ketothiolase or synthase classified under EC. 2.3.1.16, EC 2.3.1.41, EC 2.3.1.174, EC 2.3.1.179, or EC 2.3.1.180.

* * * * *

UNITED STATES PATENT AND TRADEMARK OFFICE
CERTIFICATE OF CORRECTION

PATENT NO. : 10,233,474 B2
APPLICATION NO. : 14/977004
DATED : March 19, 2019
INVENTOR(S) : Alexander Brett Foster et al.

Page 1 of 1

It is certified that error appears in the above-identified patent and that said Letters Patent is hereby corrected as shown below:

In the Claims

Claim 3, Column 121, Line 62, "ora 3-oxoacyl-CoA" should read -- or a 3-oxoacyl-CoA --.

Claim 6, Column 123, Line 7, "SEQ ID NO: 17" should read -- SEQ ID NO:17 --.

Claim 8, Column 123, Line 21, "ora 3-oxoacyl-CoA reductase" should read -- or a 3-oxoacyl-CoA reductase --.

Signed and Sealed this
Fourteenth Day of May, 2019

Andrei Iancu
*Director of the United States Patent and Trademark Office*

SEQUENCE LISTING

<160> NUMBER OF SEQ ID NOS: 28

<210> SEQ ID NO 1
<211> LENGTH: 394
<212> TYPE: PRT
<213> ORGANISM: Cupriavidus necator

<400> SEQUENCE: 1

```
Met Thr Arg Glu Val Val Val Ser Gly Val Arg Thr Ala Ile Gly
 1               5                  10                  15

Thr Phe Gly Gly Ser Leu Lys Asp Val Ala Pro Ala Glu Leu Gly Ala
            20                  25                  30

Leu Val Val Arg Glu Ala Leu Ala Arg Ala Gln Val Ser Gly Asp Asp
            35                  40                  45

Val Gly His Val Val Phe Gly Asn Val Ile Gln Thr Glu Pro Arg Asp
            50                  55                  60

Met Tyr Leu Gly Arg Val Ala Ala Val Asn Gly Gly Val Thr Ile Asn
 65              70                  75                  80

Ala Pro Ala Leu Thr Val Asn Arg Leu Cys Gly Ser Gly Leu Gln Ala
            85                  90                  95

Ile Val Ser Ala Ala Gln Thr Ile Leu Leu Gly Asp Thr Asp Val Ala
            100                 105                 110

Ile Gly Gly Gly Ala Glu Ser Met Ser Arg Ala Pro Tyr Leu Ala Pro
            115                 120                 125

Ala Ala Arg Trp Gly Ala Arg Met Gly Asp Ala Gly Leu Val Asp Met
            130                 135                 140

Met Leu Gly Ala Leu His Asp Pro Phe His Arg Ile His Met Gly Val
145                 150                 155                 160

Thr Ala Glu Asn Val Ala Lys Glu Tyr Asp Ile Ser Arg Ala Gln Gln
                165                 170                 175

Asp Glu Ala Ala Leu Glu Ser His Arg Arg Ala Ser Ala Ala Ile Lys
            180                 185                 190

Ala Gly Tyr Phe Lys Asp Gln Ile Val Pro Val Val Ser Lys Gly Arg
            195                 200                 205

Lys Gly Asp Val Thr Phe Asp Thr Asp Glu His Val Arg His Asp Ala
            210                 215                 220

Thr Ile Asp Asp Met Thr Lys Leu Arg Pro Val Phe Val Lys Glu Asn
225                 230                 235                 240

Gly Thr Val Thr Ala Gly Asn Ala Ser Gly Leu Asn Asp Ala Ala Ala
                245                 250                 255

Ala Val Val Met Met Glu Arg Ala Glu Ala Glu Arg Arg Gly Leu Lys
            260                 265                 270

Pro Leu Ala Arg Leu Val Ser Tyr Gly His Ala Gly Val Asp Pro Lys
            275                 280                 285

Ala Met Gly Ile Gly Pro Val Pro Ala Thr Lys Ile Ala Leu Glu Arg
            290                 295                 300

Ala Gly Leu Gln Val Ser Asp Leu Asp Val Ile Glu Ala Asn Glu Ala
305                 310                 315                 320

Phe Ala Ala Gln Ala Cys Ala Val Thr Lys Ala Leu Gly Leu Asp Pro
            325                 330                 335

Ala Lys Val Asn Pro Asn Gly Ser Gly Ile Ser Leu Gly His Pro Ile
            340                 345                 350

Gly Ala Thr Gly Ala Leu Ile Thr Val Lys Ala Leu His Glu Leu Asn
            355                 360                 365
```

```
Arg Val Gln Gly Arg Tyr Ala Leu Val Thr Met Cys Ile Gly Gly Gly
    370                 375                 380

Gln Gly Ile Ala Ala Ile Phe Glu Arg Ile
385                 390
```

<210> SEQ ID NO 2
<211> LENGTH: 1174
<212> TYPE: PRT
<213> ORGANISM: Mycobacterium marinum

<400> SEQUENCE: 2

```
Met Ser Pro Ile Thr Arg Glu Glu Arg Leu Glu Arg Arg Ile Gln Asp
  1               5                  10                  15

Leu Tyr Ala Asn Asp Pro Gln Phe Ala Ala Lys Pro Ala Thr Ala
             20                  25                  30

Ile Thr Ala Ala Ile Glu Arg Pro Gly Leu Pro Leu Pro Gln Ile Ile
             35                  40                  45

Glu Thr Val Met Thr Gly Tyr Ala Asp Arg Pro Ala Leu Ala Gln Arg
 50                  55                  60

Ser Val Glu Phe Val Thr Asp Ala Gly Thr Gly His Thr Thr Leu Arg
 65                  70                  75                  80

Leu Leu Pro His Phe Glu Thr Ile Ser Tyr Gly Glu Leu Trp Asp Arg
             85                  90                  95

Ile Ser Ala Leu Ala Asp Val Leu Ser Thr Glu Gln Thr Val Lys Pro
            100                 105                 110

Gly Asp Arg Val Cys Leu Leu Gly Phe Asn Ser Val Asp Tyr Ala Thr
            115                 120                 125

Ile Asp Met Thr Leu Ala Arg Leu Gly Ala Val Ala Val Pro Leu Gln
            130                 135                 140

Thr Ser Ala Ala Ile Thr Gln Leu Gln Pro Ile Val Ala Glu Thr Gln
145                 150                 155                 160

Pro Thr Met Ile Ala Ala Ser Val Asp Ala Leu Ala Asp Ala Thr Glu
                165                 170                 175

Leu Ala Leu Ser Gly Gln Thr Ala Thr Arg Val Leu Val Phe Asp His
                180                 185                 190

His Arg Gln Val Asp Ala His Arg Ala Ala Val Glu Ser Ala Arg Glu
            195                 200                 205

Arg Leu Ala Gly Ser Ala Val Val Glu Thr Leu Ala Glu Ala Ile Ala
            210                 215                 220

Arg Gly Asp Val Pro Arg Gly Ala Ser Ala Gly Ser Ala Pro Gly Thr
225                 230                 235                 240

Asp Val Ser Asp Asp Ser Leu Ala Leu Leu Ile Tyr Thr Ser Gly Ser
                245                 250                 255

Thr Gly Ala Pro Lys Gly Ala Met Tyr Pro Arg Arg Asn Val Ala Thr
                260                 265                 270

Phe Trp Arg Lys Arg Thr Trp Phe Glu Gly Gly Tyr Glu Pro Ser Ile
            275                 280                 285

Thr Leu Asn Phe Met Pro Met Ser His Val Met Gly Arg Gln Ile Leu
            290                 295                 300

Tyr Gly Thr Leu Cys Asn Gly Gly Thr Ala Tyr Phe Val Ala Lys Ser
305                 310                 315                 320

Asp Leu Ser Thr Leu Phe Glu Asp Leu Ala Leu Val Arg Pro Thr Glu
                325                 330                 335

Leu Thr Phe Val Pro Arg Val Trp Asp Met Val Phe Asp Glu Phe Gln
                340                 345                 350
```

```
Ser Glu Val Asp Arg Arg Leu Val Asp Gly Ala Asp Arg Val Ala Leu
        355                 360                 365
Glu Ala Gln Val Lys Ala Glu Ile Arg Asn Asp Val Leu Gly Gly Arg
370                 375                 380
Tyr Thr Ser Ala Leu Thr Gly Ser Ala Pro Ile Ser Asp Glu Met Lys
385                 390                 395                 400
Ala Trp Val Glu Glu Leu Leu Asp Met His Leu Val Glu Gly Tyr Gly
                405                 410                 415
Ser Thr Glu Ala Gly Met Ile Leu Ile Asp Gly Ala Ile Arg Arg Pro
                420                 425                 430
Ala Val Leu Asp Tyr Lys Leu Val Asp Val Pro Asp Leu Gly Tyr Phe
                435                 440                 445
Leu Thr Asp Arg Pro His Pro Arg Gly Glu Leu Leu Val Lys Thr Asp
            450                 455                 460
Ser Leu Phe Pro Gly Tyr Tyr Gln Arg Ala Glu Val Thr Ala Asp Val
465                 470                 475                 480
Phe Asp Ala Asp Gly Phe Tyr Arg Thr Gly Asp Ile Met Ala Glu Val
                485                 490                 495
Gly Pro Glu Gln Phe Val Tyr Leu Asp Arg Arg Asn Asn Val Leu Lys
                500                 505                 510
Leu Ser Gln Gly Glu Phe Val Thr Val Ser Lys Leu Glu Ala Val Phe
            515                 520                 525
Gly Asp Ser Pro Leu Val Arg Gln Ile Tyr Ile Tyr Gly Asn Ser Ala
            530                 535                 540
Arg Ala Tyr Leu Leu Ala Val Ile Val Pro Thr Gln Glu Ala Leu Asp
545                 550                 555                 560
Ala Val Pro Val Glu Glu Leu Lys Ala Arg Leu Gly Asp Ser Leu Gln
                565                 570                 575
Glu Val Ala Lys Ala Ala Gly Leu Gln Ser Tyr Glu Ile Pro Arg Asp
                580                 585                 590
Phe Ile Ile Glu Thr Thr Pro Trp Thr Leu Glu Asn Gly Leu Leu Thr
            595                 600                 605
Gly Ile Arg Lys Leu Ala Arg Pro Gln Leu Lys Lys His Tyr Gly Glu
        610                 615                 620
Leu Leu Glu Gln Ile Tyr Thr Asp Leu Ala His Gly Gln Ala Asp Glu
625                 630                 635                 640
Leu Arg Ser Leu Arg Gln Ser Gly Ala Asp Ala Pro Val Leu Val Thr
                645                 650                 655
Val Cys Arg Ala Ala Ala Leu Leu Gly Gly Ser Ala Ser Asp Val
                660                 665                 670
Gln Pro Asp Ala His Phe Thr Asp Leu Gly Gly Asp Ser Leu Ser Ala
            675                 680                 685
Leu Ser Phe Thr Asn Leu Leu His Glu Ile Phe Asp Ile Glu Val Pro
        690                 695                 700
Val Gly Val Ile Val Ser Pro Ala Asn Asp Leu Gln Ala Leu Ala Asp
705                 710                 715                 720
Tyr Val Glu Ala Ala Arg Lys Pro Gly Ser Ser Arg Pro Thr Phe Ala
                725                 730                 735
Ser Val His Gly Ala Ser Asn Gly Gln Val Thr Glu Val His Ala Gly
            740                 745                 750
Asp Leu Ser Leu Asp Lys Phe Ile Asp Ala Ala Thr Leu Ala Glu Ala
        755                 760                 765
```

-continued

```
Pro Arg Leu Pro Ala Ala Asn Thr Gln Val Arg Thr Val Leu Leu Thr
    770                 775                 780
Gly Ala Thr Gly Phe Leu Gly Arg Tyr Leu Ala Leu Glu Trp Leu Glu
785                 790                 795                 800
Arg Met Asp Leu Val Asp Gly Lys Leu Ile Cys Leu Val Arg Ala Lys
                805                 810                 815
Ser Asp Thr Glu Ala Arg Ala Arg Leu Asp Lys Thr Phe Asp Ser Gly
                820                 825                 830
Asp Pro Glu Leu Leu Ala His Tyr Arg Ala Leu Ala Gly Asp His Leu
            835                 840                 845
Glu Val Leu Ala Gly Asp Lys Gly Glu Ala Asp Leu Gly Leu Asp Arg
        850                 855                 860
Gln Thr Trp Gln Arg Leu Ala Asp Thr Val Asp Leu Ile Val Asp Pro
865                 870                 875                 880
Ala Ala Leu Val Asn His Val Leu Pro Tyr Ser Gln Leu Phe Gly Pro
                885                 890                 895
Asn Ala Leu Gly Thr Ala Glu Leu Leu Arg Leu Ala Leu Thr Ser Lys
                900                 905                 910
Ile Lys Pro Tyr Ser Tyr Thr Ser Thr Ile Gly Val Ala Asp Gln Ile
            915                 920                 925
Pro Pro Ser Ala Phe Thr Glu Asp Ala Asp Ile Arg Val Ile Ser Ala
        930                 935                 940
Thr Arg Ala Val Asp Asp Ser Tyr Ala Asn Gly Tyr Ser Asn Ser Lys
945                 950                 955                 960
Trp Ala Gly Glu Val Leu Leu Arg Glu Ala His Asp Leu Cys Gly Leu
                965                 970                 975
Pro Val Ala Val Phe Arg Cys Asp Met Ile Leu Ala Asp Thr Thr Trp
            980                 985                 990
Ala Gly Gln Leu Asn Val Pro Asp Met Phe Thr Arg Met Ile Leu Ser
        995                 1000                1005
Leu Ala Ala Thr Gly Ile Ala Pro Gly Ser Phe Tyr Glu Leu Ala Ala
    1010                1015                1020
Asp Gly Ala Arg Gln Arg Ala His Tyr Asp Gly Leu Pro Val Glu Phe
1025                1030                1035                1040
Ile Ala Glu Ala Ile Ser Thr Leu Gly Ala Gln Ser Gln Asp Gly Phe
                1045                1050                1055
His Thr Tyr His Val Met Asn Pro Tyr Asp Asp Gly Ile Gly Leu Asp
            1060                1065                1070
Glu Phe Val Asp Trp Leu Asn Glu Ser Gly Cys Pro Ile Gln Arg Ile
        1075                1080                1085
Ala Asp Tyr Gly Asp Trp Leu Gln Arg Phe Glu Thr Ala Leu Arg Ala
    1090                1095                1100
Leu Pro Asp Arg Gln Arg His Ser Ser Leu Leu Pro Leu Leu His Asn
1105                1110                1115                1120
Tyr Arg Gln Pro Glu Arg Pro Val Arg Gly Ser Ile Ala Pro Thr Asp
                1125                1130                1135
Arg Phe Arg Ala Ala Val Gln Glu Ala Lys Ile Gly Pro Asp Lys Asp
            1140                1145                1150
Ile Pro His Val Gly Ala Pro Ile Ile Val Lys Tyr Val Ser Asp Leu
        1155                1160                1165
Arg Leu Leu Gly Leu Leu
    1170
```

-continued

```
<210> SEQ ID NO 3
<211> LENGTH: 1173
<212> TYPE: PRT
<213> ORGANISM: Mycobacterium smegmatis

<400> SEQUENCE: 3

Met Thr Ser Asp Val His Asp Ala Thr Asp Gly Val Thr Glu Thr Ala
 1               5                  10                  15

Leu Asp Asp Glu Gln Ser Thr Arg Arg Ile Ala Glu Leu Tyr Ala Thr
            20                  25                  30

Asp Pro Glu Phe Ala Ala Ala Pro Leu Pro Ala Val Val Asp Ala
        35                  40                  45

Ala His Lys Pro Gly Leu Arg Leu Ala Glu Ile Leu Gln Thr Leu Phe
    50                  55                  60

Thr Gly Tyr Gly Asp Arg Pro Ala Leu Gly Tyr Arg Ala Arg Glu Leu
65                  70                  75                  80

Ala Thr Asp Glu Gly Gly Arg Thr Val Thr Arg Leu Leu Pro Arg Phe
                85                  90                  95

Asp Thr Leu Thr Tyr Ala Gln Val Trp Ser Arg Val Gln Ala Val Ala
            100                 105                 110

Ala Ala Leu Arg His Asn Phe Ala Gln Pro Ile Tyr Pro Gly Asp Ala
        115                 120                 125

Val Ala Thr Ile Gly Phe Ala Ser Pro Asp Tyr Leu Thr Leu Asp Leu
    130                 135                 140

Val Cys Ala Tyr Leu Gly Leu Val Ser Val Pro Leu Gln His Asn Ala
145                 150                 155                 160

Pro Val Ser Arg Leu Ala Pro Ile Leu Ala Glu Val Glu Pro Arg Ile
                165                 170                 175

Leu Thr Val Ser Ala Glu Tyr Leu Asp Leu Ala Val Glu Ser Val Arg
            180                 185                 190

Asp Val Asn Ser Val Ser Gln Leu Val Val Phe Asp His His Pro Glu
        195                 200                 205

Val Asp Asp His Arg Asp Ala Leu Ala Arg Ala Arg Glu Gln Leu Ala
    210                 215                 220

Gly Lys Gly Ile Ala Val Thr Thr Leu Asp Ala Ile Ala Asp Glu Gly
225                 230                 235                 240

Ala Gly Leu Pro Ala Glu Pro Ile Tyr Thr Ala Asp His Asp Gln Arg
                245                 250                 255

Leu Ala Met Ile Leu Tyr Thr Ser Gly Ser Thr Gly Ala Pro Lys Gly
            260                 265                 270

Ala Met Tyr Thr Glu Ala Met Val Ala Arg Leu Trp Thr Met Ser Phe
        275                 280                 285

Ile Thr Gly Asp Pro Thr Pro Val Ile Asn Val Asn Phe Met Pro Leu
    290                 295                 300

Asn His Leu Gly Gly Arg Ile Pro Ile Ser Thr Ala Val Gln Asn Gly
305                 310                 315                 320

Gly Thr Ser Tyr Phe Val Pro Glu Ser Asp Met Ser Thr Leu Phe Glu
                325                 330                 335

Asp Leu Ala Leu Val Arg Pro Thr Glu Leu Gly Leu Val Pro Arg Val
            340                 345                 350

Ala Asp Met Leu Tyr Gln His His Leu Ala Thr Val Asp Arg Leu Val
        355                 360                 365

Thr Gln Gly Ala Asp Glu Leu Thr Ala Glu Lys Gln Ala Gly Ala Glu
    370                 375                 380
```

```
Leu Arg Glu Gln Val Leu Gly Gly Arg Val Ile Thr Gly Phe Val Ser
385                 390                 395                 400

Thr Ala Pro Leu Ala Ala Glu Met Arg Ala Phe Leu Asp Ile Thr Leu
            405                 410                 415

Gly Ala His Ile Val Asp Gly Tyr Gly Leu Thr Glu Thr Gly Ala Val
                420                 425                 430

Thr Arg Asp Gly Val Ile Val Arg Pro Pro Val Ile Asp Tyr Lys Leu
        435                 440                 445

Ile Asp Val Pro Glu Leu Gly Tyr Phe Ser Thr Asp Lys Pro Tyr Pro
450                 455                 460

Arg Gly Glu Leu Leu Val Arg Ser Gln Thr Leu Thr Pro Gly Tyr Tyr
465                 470                 475                 480

Lys Arg Pro Glu Val Thr Ala Ser Val Phe Asp Arg Asp Gly Tyr Tyr
            485                 490                 495

His Thr Gly Asp Val Met Ala Glu Thr Ala Pro Asp His Leu Val Tyr
                500                 505                 510

Val Asp Arg Arg Asn Asn Val Leu Lys Leu Ala Gln Gly Glu Phe Val
        515                 520                 525

Ala Val Ala Asn Leu Glu Ala Val Phe Ser Gly Ala Ala Leu Val Arg
530                 535                 540

Gln Ile Phe Val Tyr Gly Asn Ser Glu Arg Ser Phe Leu Leu Ala Val
545                 550                 555                 560

Val Val Pro Thr Pro Glu Ala Leu Glu Gln Tyr Asp Pro Ala Ala Leu
            565                 570                 575

Lys Ala Ala Leu Ala Asp Ser Leu Gln Arg Thr Ala Arg Asp Ala Glu
                580                 585                 590

Leu Gln Ser Tyr Glu Val Pro Ala Asp Phe Ile Val Glu Thr Glu Pro
        595                 600                 605

Phe Ser Ala Ala Asn Gly Leu Leu Ser Gly Val Gly Lys Leu Leu Arg
610                 615                 620

Pro Asn Leu Lys Asp Arg Tyr Gly Gln Arg Leu Glu Gln Met Tyr Ala
625                 630                 635                 640

Asp Ile Ala Ala Thr Gln Ala Asn Gln Leu Arg Glu Leu Arg Arg Ala
            645                 650                 655

Ala Ala Thr Gln Pro Val Ile Asp Thr Leu Thr Gln Ala Ala Ala Thr
                660                 665                 670

Ile Leu Gly Thr Gly Ser Glu Val Ala Ser Asp Ala His Phe Thr Asp
        675                 680                 685

Leu Gly Gly Asp Ser Leu Ser Ala Leu Thr Leu Ser Asn Leu Leu Ser
690                 695                 700

Asp Phe Phe Gly Phe Glu Val Pro Val Gly Thr Ile Val Asn Pro Ala
705                 710                 715                 720

Thr Asn Leu Ala Gln Leu Ala Gln His Ile Glu Ala Gln Arg Thr Ala
            725                 730                 735

Gly Asp Arg Arg Pro Ser Phe Thr Val His Gly Ala Asp Ala Thr
                740                 745                 750

Glu Ile Arg Ala Ser Glu Leu Thr Leu Asp Lys Phe Ile Asp Ala Glu
        755                 760                 765

Thr Leu Arg Ala Ala Pro Gly Leu Pro Lys Val Thr Thr Glu Pro Arg
770                 775                 780

Thr Val Leu Leu Ser Gly Ala Asn Gly Trp Leu Gly Arg Phe Leu Thr
785                 790                 795                 800

Leu Gln Trp Leu Glu Arg Leu Ala Pro Val Gly Gly Thr Leu Ile Thr
```

Ile Val Arg Gly Arg Asp Ala Ala Ala Arg Ala Arg Leu Thr Gln
            805                 810                 815

Ala Tyr Asp Thr Asp Pro Glu Leu Ser Arg Arg Phe Ala Glu Leu Ala
        820                 825                 830

Asp Arg His Leu Arg Val Val Ala Gly Asp Ile Gly Asp Pro Asn Leu
835                 840                 845

Gly Leu Thr Pro Glu Ile Trp His Arg Leu Ala Ala Glu Val Asp Leu
    850                 855                 860

Val Val His Pro Ala Ala Leu Val Asn His Val Leu Pro Tyr Arg Gln
865                 870                 875                 880

Leu Phe Gly Pro Asn Val Val Gly Thr Ala Glu Val Ile Lys Leu Ala
                885                 890                 895

Leu Thr Glu Arg Ile Lys Pro Val Thr Tyr Leu Ser Thr Val Ser Val
            900                 905                 910

Ala Met Gly Ile Pro Asp Phe Glu Glu Asp Gly Asp Ile Arg Thr Val
        915                 920                 925

Ser Pro Val Arg Pro Leu Asp Gly Gly Tyr Ala Asn Gly Tyr Gly Asn
    930                 935                 940

Ser Lys Trp Ala Gly Glu Val Leu Leu Arg Glu Ala His Asp Leu Cys
945                 950                 955                 960

Gly Leu Pro Val Ala Thr Phe Arg Ser Asp Met Ile Leu Ala His Pro
                965                 970                 975

Arg Tyr Arg Gly Gln Val Asn Val Pro Asp Met Phe Thr Arg Leu Leu
            980                 985                 990

Leu Ser Leu Leu Ile Thr Gly Val Ala Pro Arg Ser Phe Tyr Ile Gly
        995                 1000                1005

Asp Gly Glu Arg Pro Arg Ala His Tyr Pro Gly Leu Thr Val Asp Phe
1010                1015                1020

Val Ala Glu Ala Val Thr Thr Leu Gly Ala Gln Gln Arg Glu Gly Tyr
    1025                1030                1035                1040

Val Ser Tyr Asp Val Met Asn Pro His Asp Asp Gly Ile Ser Leu Asp
                1045                1050                1055

Val Phe Val Asp Trp Leu Ile Arg Ala Gly His Pro Ile Asp Arg Val
            1060                1065                1070

Asp Asp Tyr Asp Asp Trp Val Arg Arg Phe Glu Thr Ala Leu Thr Ala
        1075                1080                1085

Leu Pro Glu Lys Arg Arg Ala Gln Thr Val Leu Pro Leu Leu His Ala
1090                1095                1100

Phe Arg Ala Pro Gln Ala Pro Leu Arg Gly Ala Pro Glu Pro Thr Glu
    1105                1110                1115                1120

Val Phe His Ala Ala Val Arg Thr Ala Lys Val Gly Pro Gly Asp Ile
                1125                1130                1135

Pro His Leu Asp Glu Ala Leu Ile Asp Lys Tyr Ile Arg Asp Leu Arg
            1140                1145                1150

Glu Phe Gly Leu Ile
    1155

<210> SEQ ID NO 4
<211> LENGTH: 1148
<212> TYPE: PRT
<213> ORGANISM: Segniliparus rugosus

<400> SEQUENCE: 4

```
Met Gly Asp Gly Glu Arg Ala Lys Arg Phe Phe Gln Arg Ile Gly
1               5                   10                  15

Glu Leu Ser Ala Thr Asp Pro Gln Phe Ala Ala Ala Pro Asp Pro
            20                  25                  30

Ala Val Val Glu Ala Val Ser Asp Pro Ser Leu Ser Phe Thr Arg Tyr
            35                  40                  45

Leu Asp Thr Leu Met Arg Gly Tyr Ala Glu Arg Pro Ala Leu Ala His
    50                  55                  60

Arg Val Gly Ala Gly Tyr Glu Thr Ile Ser Tyr Gly Glu Leu Trp Ala
65                  70                  75                  80

Arg Val Gly Ala Ile Ala Ala Ala Trp Gln Ala Asp Gly Leu Ala Pro
                85                  90                  95

Gly Asp Phe Val Ala Thr Val Gly Phe Thr Ser Pro Asp Tyr Val Ala
                100                 105                 110

Val Asp Leu Ala Ala Ala Arg Ser Gly Leu Val Ser Val Pro Leu Gln
                115                 120                 125

Ala Gly Ala Ser Leu Ala Gln Leu Val Gly Ile Leu Glu Glu Thr Glu
                130                 135                 140

Pro Lys Val Leu Ala Ala Ser Ala Ser Ser Leu Glu Gly Ala Val Ala
145                 150                 155                 160

Cys Ala Leu Ala Ala Pro Ser Val Gln Arg Leu Val Val Phe Asp Leu
                165                 170                 175

Arg Gly Pro Asp Ala Ser Glu Ser Ala Ala Asp Glu Arg Arg Gly Ala
                180                 185                 190

Leu Ala Asp Ala Glu Glu Gln Leu Ala Arg Ala Gly Arg Ala Val Val
                195                 200                 205

Val Glu Thr Leu Ala Asp Leu Ala Ala Arg Gly Glu Ala Leu Pro Glu
210                 215                 220

Ala Pro Leu Phe Glu Pro Ala Glu Gly Glu Asp Pro Leu Ala Leu Leu
225                 230                 235                 240

Ile Tyr Thr Ser Gly Ser Thr Gly Ala Pro Lys Gly Ala Met Tyr Ser
                245                 250                 255

Gln Arg Leu Val Ser Gln Leu Trp Gly Arg Thr Pro Val Val Pro Gly
                260                 265                 270

Met Pro Asn Ile Ser Leu His Tyr Met Pro Leu Ser His Ser Tyr Gly
    275                 280                 285

Arg Ala Val Leu Ala Gly Ala Leu Ser Ala Gly Gly Thr Ala His Phe
    290                 295                 300

Thr Ala Asn Ser Asp Leu Ser Thr Leu Phe Glu Asp Ile Ala Leu Ala
305                 310                 315                 320

Arg Pro Thr Phe Leu Ala Leu Val Pro Arg Val Cys Glu Met Leu Phe
                325                 330                 335

Gln Glu Ser Gln Arg Gly Gln Asp Val Ala Glu Leu Arg Glu Arg Val
                340                 345                 350

Leu Gly Gly Arg Leu Leu Val Ala Val Cys Gly Ser Ala Pro Leu Ser
    355                 360                 365

Pro Glu Met Arg Ala Phe Met Glu Glu Val Leu Gly Phe Pro Leu Leu
    370                 375                 380

Asp Gly Tyr Gly Ser Thr Glu Ala Leu Gly Val Met Arg Asn Gly Ile
385                 390                 395                 400

Ile Gln Arg Pro Pro Val Ile Asp Tyr Lys Leu Val Asp Val Pro Glu
                405                 410                 415

Leu Gly Tyr Arg Thr Thr Asp Lys Pro Tyr Pro Arg Gly Glu Leu Cys
```

```
            420                 425                 430
Ile Arg Ser Thr Ser Leu Ile Ser Gly Tyr Tyr Lys Arg Pro Glu Ile
            435                 440                 445
Thr Ala Glu Val Phe Asp Ala Gln Gly Tyr Tyr Lys Thr Gly Asp Val
            450                 455                 460
Met Ala Glu Ile Ala Pro Asp His Leu Val Tyr Val Asp Arg Ser Lys
465                 470                 475                 480
Asn Val Leu Lys Leu Ser Gln Gly Glu Phe Val Ala Val Ala Lys Leu
                485                 490                 495
Glu Ala Ala Tyr Gly Thr Ser Pro Tyr Val Lys Gln Ile Phe Val Tyr
                500                 505                 510
Gly Asn Ser Glu Arg Ser Phe Leu Leu Ala Val Val Pro Asn Ala
                515                 520                 525
Glu Val Leu Gly Ala Arg Asp Gln Glu Ala Lys Pro Leu Ile Ala
                530                 535                 540
Ala Ser Leu Gln Lys Ile Ala Lys Glu Ala Gly Leu Gln Ser Tyr Glu
545                 550                 555                 560
Val Pro Arg Asp Phe Leu Ile Glu Thr Glu Pro Phe Thr Thr Gln Asn
                565                 570                 575
Gly Leu Leu Ser Glu Val Gly Lys Leu Leu Arg Pro Lys Leu Lys Ala
                580                 585                 590
Arg Tyr Gly Glu Ala Leu Glu Ala Arg Tyr Asp Glu Ile Ala His Gly
                595                 600                 605
Gln Ala Asp Glu Leu Arg Ala Leu Arg Asp Gly Ala Gly Gln Arg Pro
                610                 615                 620
Val Val Glu Thr Val Val Arg Ala Ala Val Ala Ile Ser Gly Ser Glu
625                 630                 635                 640
Gly Ala Glu Val Gly Pro Glu Ala Asn Phe Ala Asp Leu Gly Gly Asp
                645                 650                 655
Ser Leu Ser Ala Leu Ser Leu Ala Asn Leu Leu His Asp Val Phe Glu
                660                 665                 670
Val Glu Val Pro Val Arg Ile Ile Gly Pro Thr Ala Ser Leu Ala
                675                 680                 685
Gly Ile Ala Lys His Ile Glu Ala Glu Arg Ala Gly Ala Ser Ala Pro
                690                 695                 700
Thr Ala Ala Ser Val His Gly Ala Gly Ala Thr Arg Ile Arg Ala Ser
705                 710                 715                 720
Glu Leu Thr Leu Glu Lys Phe Leu Pro Glu Asp Leu Leu Ala Ala Ala
                725                 730                 735
Lys Gly Leu Pro Ala Ala Asp Gln Val Arg Thr Val Leu Leu Thr Gly
                740                 745                 750
Ala Asn Gly Trp Leu Gly Arg Phe Leu Ala Leu Glu Gln Leu Glu Arg
                755                 760                 765
Leu Ala Arg Ser Gly Gln Asp Gly Gly Lys Leu Ile Cys Leu Val Arg
                770                 775                 780
Gly Lys Asp Ala Ala Ala Arg Arg Ile Glu Glu Thr Leu Gly
785                 790                 795                 800
Thr Asp Pro Ala Leu Ala Ala Arg Phe Ala Glu Leu Ala Glu Gly Arg
                805                 810                 815
Leu Glu Val Val Pro Gly Asp Val Gly Glu Pro Lys Phe Gly Leu Asp
                820                 825                 830
Asp Ala Ala Trp Asp Arg Leu Ala Glu Glu Val Asp Val Ile Val His
                835                 840                 845
```

Pro Ala Ala Leu Val Asn His Val Leu Pro Tyr His Gln Leu Phe Gly
              850                 855                 860

Pro Asn Val Val Gly Thr Ala Glu Ile Ile Arg Leu Ala Ile Thr Ala
865                 870                 875                 880

Lys Arg Lys Pro Val Thr Tyr Leu Ser Thr Val Ala Val Ala Ala Gly
              885                 890                 895

Val Glu Pro Ser Ser Phe Glu Glu Asp Gly Asp Ile Arg Ala Val Val
              900                 905                 910

Pro Glu Arg Pro Leu Gly Asp Gly Tyr Ala Asn Gly Tyr Gly Asn Ser
              915                 920                 925

Lys Trp Ala Gly Glu Val Leu Leu Arg Glu Ala His Glu Leu Val Gly
              930                 935                 940

Leu Pro Val Ala Val Phe Arg Ser Asp Met Ile Leu Ala His Thr Arg
945                 950                 955                 960

Tyr Thr Gly Gln Leu Asn Val Pro Asp Gln Phe Thr Arg Leu Val Leu
              965                 970                 975

Ser Leu Leu Ala Thr Gly Ile Ala Pro Lys Ser Phe Tyr Gln Gln Gly
              980                 985                 990

Ala Ala Gly Glu Arg Gln Arg Ala His Tyr Asp Gly Ile Pro Val Asp
              995                 1000                1005

Phe Thr Ala Glu Ala Ile Thr Thr Leu Gly Ala Glu Pro Ser Trp Phe
              1010                1015                1020

Asp Gly Gly Ala Gly Phe Arg Ser Phe Asp Val Phe Asn Pro His His
1025                1030                1035                1040

Asp Gly Val Gly Leu Asp Glu Phe Val Asp Trp Leu Ile Glu Ala Gly
              1045                1050                1055

His Pro Ile Ser Arg Ile Asp Asp His Lys Glu Trp Phe Ala Arg Phe
              1060                1065                1070

Glu Thr Ala Val Arg Gly Leu Pro Glu Ala Gln Arg Gln His Ser Leu
              1075                1080                1085

Leu Pro Leu Leu Arg Ala Tyr Ser Phe Pro His Pro Pro Val Asp Gly
              1090                1095                1100

Ser Val Tyr Pro Thr Gly Lys Phe Gln Gly Ala Val Lys Ala Ala Gln
1105                1110                1115                1120

Val Gly Ser Asp His Asp Val Pro His Leu Gly Lys Ala Leu Ile Val
              1125                1130                1135

Lys Tyr Ala Asp Asp Leu Lys Ala Leu Gly Leu Leu
              1140                1145

<210> SEQ ID NO 5
<211> LENGTH: 1185
<212> TYPE: PRT
<213> ORGANISM: Mycobacterium massiliense

<400> SEQUENCE: 5

Met Thr Asn Glu Thr Asn Pro Gln Gln Glu Gln Leu Ser Arg Arg Ile
1               5                   10                  15

Glu Ser Leu Arg Glu Ser Asp Pro Gln Phe Arg Ala Ala Gln Pro Asp
              20                  25                  30

Pro Ala Val Ala Glu Gln Val Leu Arg Pro Gly Leu His Leu Ser Glu
              35                  40                  45

Ala Ile Ala Ala Leu Met Thr Gly Tyr Ala Glu Arg Pro Ala Leu Gly
          50                  55                  60

Glu Arg Ala Arg Glu Leu Val Ile Asp Gln Asp Gly Arg Thr Thr Leu

-continued

```
            65                   70                    75                    80
Arg Leu Leu Pro Arg Phe Asp Thr Thr Thr Tyr Gly Glu Leu Trp Ser
                     85                    90                    95
Arg Thr Thr Ser Val Ala Ala Ala Trp His Asp Ala Thr His Pro
                100                   105                   110
Val Lys Ala Gly Asp Leu Val Ala Thr Leu Gly Phe Thr Ser Ile Asp
                115                   120                   125
Tyr Thr Val Leu Asp Leu Ala Ile Met Ile Leu Gly Val Ala Val
130                  135                   140
Pro Leu Gln Thr Ser Ala Pro Ala Ser Gln Trp Thr Thr Ile Leu Ala
145                  150                   155                   160
Glu Ala Glu Pro Asn Thr Leu Ala Val Ser Ile Glu Leu Ile Gly Ala
                165                   170                   175
Ala Met Glu Ser Val Arg Ala Thr Pro Ser Ile Lys Gln Val Val
                180                   185                   190
Phe Asp Tyr Thr Pro Glu Val Asp Asp Gln Arg Glu Ala Phe Glu Ala
                195                   200                   205
Ala Ser Thr Gln Leu Ala Gly Thr Gly Ile Ala Leu Glu Thr Leu Asp
210                  215                   220
Ala Val Ile Ala Arg Gly Ala Ala Leu Pro Ala Ala Pro Leu Tyr Ala
225                  230                   235                   240
Pro Ser Ala Gly Asp Asp Pro Leu Ala Leu Leu Ile Tyr Thr Ser Gly
                245                   250                   255
Ser Thr Gly Ala Pro Lys Gly Ala Met His Ser Glu Asn Ile Val Arg
                260                   265                   270
Arg Trp Trp Ile Arg Glu Asp Val Met Ala Gly Thr Glu Asn Leu Pro
                275                   280                   285
Met Ile Gly Leu Asn Phe Met Pro Met Ser His Ile Met Gly Arg Gly
                290                   295                   300
Thr Leu Thr Ser Thr Leu Ser Thr Gly Gly Thr Gly Tyr Phe Ala Ala
305                  310                   315                   320
Ser Ser Asp Met Ser Thr Leu Phe Glu Asp Met Glu Leu Ile Arg Pro
                325                   330                   335
Thr Ala Leu Ala Leu Val Pro Arg Val Cys Asp Met Val Phe Gln Arg
                340                   345                   350
Phe Gln Thr Glu Val Asp Arg Arg Leu Ala Ser Gly Asp Thr Ala Ser
                355                   360                   365
Ala Glu Ala Val Ala Ala Glu Val Lys Ala Asp Ile Arg Asp Asn Leu
370                  375                   380
Phe Gly Gly Arg Val Ser Ala Val Met Val Gly Ser Ala Pro Leu Ser
385                  390                   395                   400
Glu Glu Leu Gly Glu Phe Ile Glu Ser Cys Phe Glu Leu Asn Leu Thr
                405                   410                   415
Asp Gly Tyr Gly Ser Thr Glu Ala Gly Met Val Phe Arg Asp Gly Ile
                420                   425                   430
Val Gln Arg Pro Pro Val Ile Asp Tyr Lys Leu Val Asp Val Pro Glu
                435                   440                   445
Leu Gly Tyr Phe Ser Thr Asp Lys Pro His Pro Arg Gly Glu Leu Leu
                450                   455                   460
Leu Lys Thr Asp Gly Met Phe Leu Gly Tyr Tyr Lys Arg Pro Glu Val
465                  470                   475                   480
Thr Ala Ser Val Phe Asp Ala Asp Gly Phe Tyr Met Thr Gly Asp Ile
                485                   490                   495
```

-continued

Val Ala Glu Leu Ala His Asp Asn Ile Glu Ile Ile Asp Arg Arg Asn
            500                 505                 510

Asn Val Leu Lys Leu Ser Gln Gly Glu Phe Val Ala Val Ala Thr Leu
            515                 520                 525

Glu Ala Glu Tyr Ala Asn Ser Pro Val Val His Gln Ile Tyr Val Tyr
            530                 535                 540

Gly Ser Ser Glu Arg Ser Tyr Leu Leu Ala Val Val Val Pro Thr Pro
545                 550                 555                 560

Glu Ala Val Ala Ala Lys Gly Asp Ala Ala Leu Lys Thr Thr
                565                 570                 575

Ile Ala Asp Ser Leu Gln Asp Ile Ala Lys Glu Ile Gln Leu Gln Ser
            580                 585                 590

Tyr Glu Val Pro Arg Asp Phe Ile Ile Glu Pro Gln Pro Phe Thr Gln
            595                 600                 605

Gly Asn Gly Leu Leu Thr Gly Ile Ala Lys Leu Ala Arg Pro Asn Leu
            610                 615                 620

Lys Ala His Tyr Gly Pro Arg Leu Glu Gln Met Tyr Ala Glu Ile Ala
625                 630                 635                 640

Glu Gln Gln Ala Ala Glu Leu Arg Ala Leu His Gly Val Asp Pro Asp
                645                 650                 655

Lys Pro Ala Leu Glu Thr Val Leu Lys Ala Ala Gln Ala Leu Leu Gly
            660                 665                 670

Val Ser Ser Ala Glu Leu Ala Ala Asp Ala His Phe Thr Asp Leu Gly
            675                 680                 685

Gly Asp Ser Leu Ser Ala Leu Ser Phe Ser Asp Leu Leu Arg Asp Ile
            690                 695                 700

Phe Ala Val Glu Val Pro Val Gly Val Ile Val Ser Ala Ala Asn Asp
705                 710                 715                 720

Leu Gly Gly Val Ala Lys Phe Val Asp Glu Gln Arg His Ser Gly Gly
                725                 730                 735

Thr Arg Pro Thr Ala Glu Thr Val His Gly Ala Gly His Thr Glu Ile
            740                 745                 750

Arg Ala Ala Asp Leu Thr Leu Asp Lys Phe Ile Asp Glu Ala Thr Leu
            755                 760                 765

His Ala Ala Pro Ser Leu Pro Lys Ala Ala Gly Ile Pro His Thr Val
            770                 775                 780

Leu Leu Thr Gly Ser Asn Gly Tyr Leu Gly His Tyr Leu Ala Leu Glu
785                 790                 795                 800

Trp Leu Glu Arg Leu Asp Lys Thr Asp Gly Lys Leu Ile Val Ile Val
                805                 810                 815

Arg Gly Lys Asn Ala Glu Ala Ala Tyr Gly Arg Leu Glu Glu Ala Phe
            820                 825                 830

Asp Thr Gly Asp Thr Glu Leu Leu Ala His Phe Arg Ser Leu Ala Asp
            835                 840                 845

Lys His Leu Glu Val Leu Ala Gly Asp Ile Gly Asp Pro Asn Leu Gly
850                 855                 860

Leu Asp Ala Asp Thr Trp Gln Arg Leu Ala Asp Thr Val Asp Val Ile
865                 870                 875                 880

Val His Pro Ala Ala Leu Val Asn His Val Leu Pro Tyr Asn Gln Leu
                885                 890                 895

Phe Gly Pro Asn Val Val Gly Thr Ala Glu Ile Ile Lys Leu Ala Ile
            900                 905                 910

```
Thr Thr Lys Ile Lys Pro Val Thr Tyr Leu Ser Thr Val Ala Val Ala
            915                 920                 925

Ala Tyr Val Asp Pro Thr Thr Phe Asp Glu Glu Ser Asp Ile Arg Leu
        930                 935                 940

Ile Ser Ala Val Arg Pro Ile Asp Asp Gly Tyr Ala Asn Gly Tyr Gly
945                 950                 955                 960

Asn Ala Lys Trp Ala Gly Glu Val Leu Leu Arg Glu Ala His Asp Leu
                965                 970                 975

Cys Gly Leu Pro Val Ala Val Phe Arg Ser Asp Met Ile Leu Ala His
            980                 985                 990

Ser Arg Tyr Thr Gly Gln Leu Asn Val Pro Asp Gln Phe Thr Arg Leu
        995                 1000                1005

Ile Leu Ser Leu Ile Ala Thr Gly Ile Ala Pro Gly Ser Phe Tyr Gln
    1010                1015                1020

Ala Gln Thr Thr Gly Glu Arg Pro Leu Ala His Tyr Asp Gly Leu Pro
1025                1030                1035                1040

Gly Asp Phe Thr Ala Glu Ala Ile Thr Thr Leu Gly Thr Gln Val Pro
                1045                1050                1055

Glu Gly Ser Glu Gly Phe Val Thr Tyr Asp Cys Val Asn Pro His Ala
            1060                1065                1070

Asp Gly Ile Ser Leu Asp Asn Phe Val Asp Trp Leu Ile Glu Ala Gly
        1075                1080                1085

Tyr Pro Ile Ala Arg Ile Asp Asn Tyr Thr Glu Trp Phe Thr Arg Phe
                1090                1095                1100

Asp Thr Ala Ile Arg Gly Leu Ser Glu Lys Gln Lys Gln His Ser Leu
1105                1110                1115                1120

Leu Pro Leu Leu His Ala Phe Glu Gln Pro Ser Ala Ala Glu Asn His
                1125                1130                1135

Gly Val Val Pro Ala Lys Arg Phe Gln His Ala Val Gln Ala Ala Gly
            1140                1145                1150

Ile Gly Pro Val Gly Gln Asp Gly Thr Thr Asp Ile Pro His Leu Ser
        1155                1160                1165

Arg Arg Leu Ile Val Lys Tyr Ala Lys Asp Leu Glu Gln Leu Gly Leu
1170                1175                1180

Leu
1185

<210> SEQ ID NO 6
<211> LENGTH: 1186
<212> TYPE: PRT
<213> ORGANISM: Segniliparus rotundus

<400> SEQUENCE: 6

Met Thr Gln Ser His Thr Gln Gly Pro Gln Ala Ser Ala Ala His Ser
 1               5                  10                  15

Arg Leu Ala Arg Arg Ala Ala Glu Leu Leu Ala Thr Asp Pro Gln Ala
            20                  25                  30

Ala Ala Thr Leu Pro Asp Pro Glu Val Val Arg Gln Ala Thr Arg Pro
        35                  40                  45

Gly Leu Arg Leu Ala Glu Arg Val Asp Ala Ile Leu Ser Gly Tyr Ala
    50                  55                  60

Asp Arg Pro Ala Leu Gly Gln Arg Ser Phe Gln Thr Val Lys Asp Pro
65                  70                  75                  80

Ile Thr Gly Arg Ser Ser Val Glu Leu Leu Pro Thr Phe Asp Thr Ile
                85                  90                  95
```

```
Thr Tyr Arg Glu Leu Arg Glu Arg Ala Thr Ala Ile Ala Ser Asp Leu
            100                 105                 110

Ala His His Pro Gln Ala Pro Ala Lys Pro Gly Asp Phe Leu Ala Ser
            115                 120                 125

Ile Gly Phe Ile Ser Val Asp Tyr Val Ala Ile Asp Ile Ala Gly Val
130                 135                 140

Phe Ala Gly Leu Thr Ala Val Pro Leu Gln Thr Gly Ala Thr Leu Ala
145                 150                 155                 160

Thr Leu Thr Ala Ile Thr Ala Glu Thr Ala Pro Thr Leu Phe Ala Ala
                    165                 170                 175

Ser Ile Glu His Leu Pro Thr Ala Val Asp Ala Val Leu Ala Thr Pro
                180                 185                 190

Ser Val Arg Arg Leu Leu Val Phe Asp Tyr Arg Ala Gly Ser Asp Glu
            195                 200                 205

Asp Arg Glu Ala Val Glu Ala Ala Lys Arg Lys Ile Ala Asp Ala Gly
            210                 215                 220

Ser Ser Val Leu Val Asp Val Leu Asp Glu Val Ile Ala Arg Gly Lys
225                 230                 235                 240

Ser Ala Pro Lys Ala Pro Leu Pro Pro Ala Thr Asp Ala Gly Asp Asp
                245                 250                 255

Ser Leu Ser Leu Leu Ile Tyr Thr Ser Gly Ser Thr Gly Thr Pro Lys
                260                 265                 270

Gly Ala Met Tyr Pro Glu Arg Asn Val Ala His Phe Trp Gly Gly Val
            275                 280                 285

Trp Ala Ala Phe Asp Glu Asp Ala Ala Pro Val Pro Ala Ile
            290                 295                 300

Asn Ile Thr Phe Leu Pro Leu Ser His Val Ala Ser Arg Leu Ser Leu
305                 310                 315                 320

Met Pro Thr Leu Ala Arg Gly Gly Leu Met His Phe Val Ala Lys Ser
                325                 330                 335

Asp Leu Ser Thr Leu Phe Glu Asp Leu Lys Leu Ala Arg Pro Thr Asn
                340                 345                 350

Leu Phe Leu Val Pro Arg Val Val Glu Met Leu Tyr Gln His Tyr Gln
            355                 360                 365

Ser Glu Leu Asp Arg Arg Gly Val Gln Asp Gly Thr Arg Glu Ala Glu
            370                 375                 380

Ala Val Lys Asp Asp Leu Arg Thr Gly Leu Leu Gly Gly Arg Ile Leu
385                 390                 395                 400

Thr Ala Gly Phe Gly Ser Ala Pro Leu Ser Ala Glu Leu Ala Gly Phe
                405                 410                 415

Ile Glu Ser Leu Leu Gln Ile His Leu Val Asp Gly Tyr Gly Ser Thr
                420                 425                 430

Glu Ala Gly Pro Val Trp Arg Asp Gly Tyr Leu Val Lys Pro Pro Val
            435                 440                 445

Thr Asp Tyr Lys Leu Ile Asp Val Pro Glu Leu Gly Tyr Phe Ser Thr
            450                 455                 460

Asp Ser Pro His Pro Arg Gly Glu Leu Ala Ile Lys Thr Gln Thr Ile
465                 470                 475                 480

Leu Pro Gly Tyr Tyr Lys Arg Pro Glu Thr Thr Ala Glu Val Phe Asp
                485                 490                 495

Glu Asp Gly Phe Tyr Leu Thr Gly Asp Val Val Ala Gln Ile Gly Pro
            500                 505                 510
```

```
Glu Gln Phe Ala Tyr Val Asp Arg Lys Asn Val Leu Lys Leu Ser
            515                 520                 525
Gln Gly Glu Phe Val Thr Leu Ala Lys Leu Glu Ala Ala Tyr Ser Ser
        530                 535                 540
Ser Pro Leu Val Arg Gln Leu Phe Val Tyr Gly Ser Ser Glu Arg Ser
545                 550                 555                 560
Tyr Leu Leu Ala Val Ile Val Pro Thr Pro Asp Ala Leu Lys Lys Phe
                565                 570                 575
Gly Val Gly Glu Ala Ala Lys Ala Ala Leu Gly Glu Ser Leu Gln Lys
            580                 585                 590
Ile Ala Arg Asp Glu Gly Leu Gln Ser Tyr Glu Val Pro Arg Asp Phe
        595                 600                 605
Ile Ile Glu Thr Asp Pro Phe Thr Val Glu Asn Gly Leu Leu Ser Asp
    610                 615                 620
Ala Arg Lys Ser Leu Arg Pro Lys Leu Lys Glu His Tyr Gly Glu Arg
625                 630                 635                 640
Leu Glu Ala Met Tyr Lys Glu Leu Ala Asp Gly Gln Ala Asn Glu Leu
                645                 650                 655
Arg Asp Ile Arg Arg Gly Val Gln Gln Arg Pro Thr Leu Glu Thr Val
            660                 665                 670
Arg Arg Ala Ala Ala Ala Met Leu Gly Ala Ser Ala Ala Glu Ile Lys
        675                 680                 685
Pro Asp Ala His Phe Thr Asp Leu Gly Gly Asp Ser Leu Ser Ala Leu
    690                 695                 700
Thr Phe Ser Asn Phe Leu His Asp Leu Phe Glu Val Asp Val Pro Val
705                 710                 715                 720
Gly Val Ile Val Ser Ala Ala Asn Thr Leu Gly Ser Val Ala Glu His
                725                 730                 735
Ile Asp Ala Gln Leu Ala Gly Gly Arg Ala Arg Pro Thr Phe Ala Thr
            740                 745                 750
Val His Gly Lys Gly Ser Thr Thr Ile Lys Ala Ser Asp Leu Thr Leu
        755                 760                 765
Asp Lys Phe Ile Asp Glu Gln Thr Leu Glu Ala Ala Lys His Leu Pro
    770                 775                 780
Lys Pro Ala Asp Pro Pro Arg Thr Val Leu Leu Thr Gly Ala Asn Gly
785                 790                 795                 800
Trp Leu Gly Arg Phe Leu Ala Leu Glu Trp Leu Glu Arg Leu Ala Pro
                805                 810                 815
Ala Gly Gly Lys Leu Ile Thr Ile Val Arg Gly Lys Asp Ala Ala Gln
            820                 825                 830
Ala Lys Ala Arg Leu Asp Ala Ala Tyr Glu Ser Gly Asp Pro Lys Leu
        835                 840                 845
Ala Gly His Tyr Gln Asp Leu Ala Ala Thr Thr Leu Glu Val Leu Ala
    850                 855                 860
Gly Asp Phe Ser Glu Pro Arg Leu Gly Leu Asp Glu Ala Thr Trp Asn
865                 870                 875                 880
Arg Leu Ala Asp Glu Val Asp Phe Ile Ser His Pro Gly Ala Leu Val
                885                 890                 895
Asn His Val Leu Pro Tyr Asn Gln Leu Phe Gly Pro Asn Val Ala Gly
            900                 905                 910
Val Ala Glu Ile Ile Lys Leu Ala Ile Thr Thr Arg Ile Lys Pro Val
        915                 920                 925
Thr Tyr Leu Ser Thr Val Ala Val Ala Ala Gly Val Glu Pro Ser Ala
```

```
        930             935             940
Leu Asp Glu Asp Gly Asp Ile Arg Thr Val Ser Ala Glu Arg Ser Val
945             950             955             960

Asp Glu Gly Tyr Ala Asn Gly Tyr Gly Asn Ser Lys Trp Gly Gly Glu
            965             970             975

Val Leu Leu Arg Glu Ala His Asp Arg Thr Gly Leu Pro Val Arg Val
            980             985             990

Phe Arg Ser Asp Met Ile Leu Ala His Gln Lys Tyr Thr Gly Gln Val
            995            1000            1005

Asn Ala Thr Asp Gln Phe Thr Arg Leu Val Gln Ser Leu Leu Ala Thr
           1010            1015            1020

Gly Leu Ala Pro Lys Ser Phe Tyr Glu Leu Asp Ala Gln Gly Asn Arg
1025            1030            1035            1040

Gln Arg Ala His Tyr Asp Gly Ile Pro Val Asp Phe Thr Ala Glu Ser
            1045            1050            1055

Ile Thr Thr Leu Gly Gly Asp Gly Leu Glu Gly Tyr Arg Ser Tyr Asn
            1060            1065            1070

Val Phe Asn Pro His Arg Asp Gly Val Gly Leu Asp Glu Phe Val Asp
            1075            1080            1085

Trp Leu Ile Glu Ala Gly His Pro Ile Thr Arg Ile Asp Asp Tyr Asp
            1090            1095            1100

Gln Trp Leu Ser Arg Phe Glu Thr Ser Leu Arg Gly Leu Pro Glu Ser
1105            1110            1115            1120

Lys Arg Gln Ala Ser Val Leu Pro Leu Leu His Ala Phe Ala Arg Pro
            1125            1130            1135

Gly Pro Ala Val Asp Gly Ser Pro Phe Arg Asn Thr Val Phe Arg Thr
            1140            1145            1150

Asp Val Gln Lys Ala Lys Ile Gly Ala Glu His Asp Ile Pro His Leu
            1155            1160            1165

Gly Lys Ala Leu Val Leu Lys Tyr Ala Asp Asp Ile Lys Gln Leu Gly
            1170            1175            1180

Leu Leu
1185

<210> SEQ ID NO 7
<211> LENGTH: 459
<212> TYPE: PRT
<213> ORGANISM: Chromobacterium violaceum

<400> SEQUENCE: 7

Met Gln Lys Gln Arg Thr Thr Ser Gln Trp Arg Glu Leu Asp Ala Ala
1               5                  10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Ser Glu
        35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Phe Asp
            100                 105                 110
```

```
Arg Val Phe Tyr Thr Asn Ser Gly Ser Glu Ser Val Asp Thr Met Ile
            115                 120                 125

Arg Met Val Arg Arg Tyr Trp Asp Val Gln Gly Lys Pro Glu Lys Lys
130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
        275                 280                 285

Gly Leu Ser Ser Gly Tyr Leu Pro Ile Gly Ala Val Phe Val Gly Lys
290                 295                 300

Arg Val Ala Glu Gly Leu Ile Ala Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
        355                 360                 365

His Val Asp Asp Val Arg Gly Val Gly Met Val Gln Ala Phe Thr Leu
370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Arg
                405                 410                 415

Ala Cys Gly Asp His Ile Val Ser Ala Pro Pro Leu Val Met Thr Arg
            420                 425                 430

Ala Glu Val Asp Glu Met Leu Ala Val Ala Glu Arg Cys Leu Glu Glu
        435                 440                 445

Phe Glu Gln Thr Leu Lys Ala Arg Gly Leu Ala
450                 455

<210> SEQ ID NO 8
<211> LENGTH: 468
<212> TYPE: PRT
<213> ORGANISM: Pseudomonas aeruginosa

<400> SEQUENCE: 8

Met Asn Ala Arg Leu His Ala Thr Ser Pro Leu Gly Asp Ala Asp Leu
1               5                   10                  15

Val Arg Ala Asp Gln Ala His Tyr Met His Gly Tyr His Val Phe Asp
            20                  25                  30
```

-continued

Asp His Arg Val Asn Gly Ser Leu Asn Ile Ala Ala Gly Asp Gly Ala
         35                  40                  45

Tyr Ile Tyr Asp Thr Ala Gly Asn Arg Tyr Leu Asp Ala Val Gly Gly
     50                  55                  60

Met Trp Cys Thr Asn Ile Gly Leu Gly Arg Glu Glu Met Ala Arg Thr
65                  70                  75                  80

Val Ala Glu Gln Thr Arg Leu Leu Ala Tyr Ser Asn Pro Phe Cys Asp
                 85                  90                  95

Met Ala Asn Pro Arg Ala Ile Glu Leu Cys Arg Lys Leu Ala Glu Leu
                100                 105                 110

Ala Pro Gly Asp Leu Asp His Val Phe Leu Thr Thr Gly Gly Ser Thr
             115                 120                 125

Ala Val Asp Thr Ala Ile Arg Leu Met His Tyr Tyr Gln Asn Cys Arg
         130                 135                 140

Gly Lys Arg Ala Lys Lys His Val Ile Thr Arg Ile Asn Ala Tyr His
145                 150                 155                 160

Gly Ser Thr Phe Leu Gly Met Ser Leu Gly Gly Lys Ser Ala Asp Arg
                165                 170                 175

Pro Ala Glu Phe Asp Phe Leu Asp Glu Arg Ile His His Leu Ala Cys
             180                 185                 190

Pro Tyr Tyr Tyr Arg Ala Pro Glu Gly Leu Gly Glu Ala Glu Phe Leu
         195                 200                 205

Asp Gly Leu Val Asp Glu Phe Glu Arg Lys Ile Leu Glu Leu Gly Ala
     210                 215                 220

Asp Arg Val Gly Ala Phe Ile Ser Glu Pro Val Phe Gly Ser Gly Gly
225                 230                 235                 240

Val Ile Val Pro Pro Ala Gly Tyr His Arg Arg Met Trp Glu Leu Cys
                245                 250                 255

Gln Arg Tyr Asp Val Leu Tyr Ile Ser Asp Glu Val Val Thr Ser Phe
             260                 265                 270

Gly Arg Leu Gly His Phe Phe Ala Ser Gln Ala Val Phe Gly Val Gln
         275                 280                 285

Pro Asp Ile Ile Leu Thr Ala Lys Gly Leu Thr Ser Gly Tyr Gln Pro
     290                 295                 300

Leu Gly Ala Cys Ile Phe Ser Arg Arg Ile Trp Glu Val Ile Ala Glu
305                 310                 315                 320

Pro Asp Lys Gly Arg Cys Phe Ser His Gly Phe Thr Tyr Ser Gly His
                325                 330                 335

Pro Val Ala Cys Ala Ala Ala Leu Lys Asn Ile Glu Ile Ile Glu Arg
             340                 345                 350

Glu Gly Leu Leu Ala His Ala Asp Glu Val Gly Arg Tyr Phe Glu Glu
         355                 360                 365

Arg Leu Gln Ser Leu Arg Asp Leu Pro Ile Val Gly Asp Val Arg Gly
     370                 375                 380

Met Arg Phe Met Ala Cys Val Glu Phe Val Ala Asp Lys Ala Ser Lys
385                 390                 395                 400

Ala Leu Phe Pro Glu Ser Leu Asn Ile Gly Glu Trp Val His Leu Arg
                405                 410                 415

Ala Gln Lys Arg Gly Leu Leu Val Arg Pro Ile Val His Leu Asn Val
             420                 425                 430

Met Ser Pro Pro Leu Ile Leu Thr Arg Glu Gln Val Asp Thr Val Val
         435                 440                 445

Arg Val Leu Arg Glu Ser Ile Glu Glu Thr Val Glu Asp Leu Val Arg
    450                 455                 460

Ala Gly His Arg
465

<210> SEQ ID NO 9
<211> LENGTH: 454
<212> TYPE: PRT
<213> ORGANISM: Pseudomonas syringae

<400> SEQUENCE: 9

Met Ser Ala Asn Asn Pro Gln Thr Leu Glu Trp Gln Ala Leu Ser Ser
  1               5                  10                  15

Glu His His Leu Ala Pro Phe Ser Asp Tyr Lys Gln Leu Lys Glu Lys
                 20                  25                  30

Gly Pro Arg Ile Ile Thr Arg Ala Glu Gly Val Tyr Leu Trp Asp Ser
             35                  40                  45

Glu Gly Asn Lys Ile Leu Asp Gly Met Ser Gly Leu Trp Cys Val Ala
         50                  55                  60

Ile Gly Tyr Gly Arg Glu Glu Leu Ala Asp Ala Ala Ser Lys Gln Met
 65                  70                  75                  80

Arg Glu Leu Pro Tyr Tyr Asn Leu Phe Phe Gln Thr Ala His Pro Pro
                 85                  90                  95

Val Leu Glu Leu Ala Lys Ala Ile Ser Asp Ile Ala Pro Glu Gly Met
            100                 105                 110

Asn His Val Phe Phe Thr Gly Ser Gly Ser Glu Gly Asn Asp Thr Met
            115                 120                 125

Leu Arg Met Val Arg His Tyr Trp Ala Leu Lys Gly Gln Pro Asn Lys
        130                 135                 140

Lys Thr Ile Ile Ser Arg Val Asn Gly Tyr His Gly Ser Thr Val Ala
145                 150                 155                 160

Gly Ala Ser Leu Gly Gly Met Thr Tyr Met His Glu Gln Gly Asp Leu
                165                 170                 175

Pro Ile Pro Gly Val Val His Ile Pro Gln Pro Tyr Trp Phe Gly Glu
            180                 185                 190

Gly Gly Asp Met Thr Pro Asp Glu Phe Gly Ile Trp Ala Ala Glu Gln
        195                 200                 205

Leu Glu Lys Lys Ile Leu Glu Leu Gly Val Glu Asn Val Gly Ala Phe
    210                 215                 220

Ile Ala Glu Pro Ile Gln Gly Ala Gly Gly Val Ile Val Pro Pro Asp
225                 230                 235                 240

Ser Tyr Trp Pro Lys Ile Lys Glu Ile Leu Ser Arg Tyr Asp Ile Leu
                245                 250                 255

Phe Ala Ala Asp Glu Val Ile Cys Gly Phe Gly Arg Thr Ser Glu Trp
            260                 265                 270

Phe Gly Ser Asp Phe Tyr Gly Leu Arg Pro Asp Met Met Thr Ile Ala
        275                 280                 285

Lys Gly Leu Thr Ser Gly Tyr Val Pro Met Gly Gly Leu Ile Val Arg
    290                 295                 300

Asp Glu Ile Val Ala Val Leu Asn Glu Gly Gly Asp Phe Asn His Gly
305                 310                 315                 320

Phe Thr Tyr Ser Gly His Pro Val Ala Ala Ala Val Ala Leu Glu Asn
                325                 330                 335

Ile Arg Ile Leu Arg Glu Glu Lys Ile Val Glu Arg Val Arg Ser Glu
            340                 345                 350

```
Thr Ala Pro Tyr Leu Gln Lys Arg Leu Arg Glu Leu Ser Asp His Pro
            355                 360                 365

Leu Val Gly Glu Val Arg Gly Val Gly Leu Leu Gly Ala Ile Glu Leu
    370                 375                 380

Val Lys Asp Lys Thr Thr Arg Glu Arg Tyr Thr Asp Lys Gly Ala Gly
385                 390                 395                 400

Met Ile Cys Arg Thr Phe Cys Phe Asp Asn Gly Leu Ile Met Arg Ala
                405                 410                 415

Val Gly Asp Thr Met Ile Ile Ala Pro Pro Leu Val Ile Ser Phe Ala
                420                 425                 430

Gln Ile Asp Glu Leu Val Glu Lys Ala Arg Thr Cys Leu Asp Leu Thr
            435                 440                 445

Leu Ala Val Leu Gln Gly
    450
```

<210> SEQ ID NO 10
<211> LENGTH: 467
<212> TYPE: PRT
<213> ORGANISM: Rhodobacter sphaeroides

<400> SEQUENCE: 10

```
Met Thr Arg Asn Asp Ala Thr Asn Ala Ala Gly Ala Val Gly Ala Ala
1               5                   10                  15

Met Arg Asp His Ile Leu Leu Pro Ala Gln Glu Met Ala Lys Leu Gly
                20                  25                  30

Lys Ser Ala Gln Pro Val Leu Thr His Ala Glu Gly Ile Tyr Val His
            35                  40                  45

Thr Glu Asp Gly Arg Arg Leu Ile Asp Gly Pro Ala Gly Met Trp Cys
        50                  55                  60

Ala Gln Val Gly Tyr Gly Arg Arg Glu Ile Val Asp Ala Met Ala His
65                  70                  75                  80

Gln Ala Met Val Leu Pro Tyr Ala Ser Pro Trp Tyr Met Ala Thr Ser
                85                  90                  95

Pro Ala Ala Arg Leu Ala Glu Lys Ile Ala Thr Leu Thr Pro Gly Asp
                100                 105                 110

Leu Asn Arg Ile Phe Phe Thr Thr Gly Gly Ser Thr Ala Val Asp Ser
            115                 120                 125

Ala Leu Arg Phe Ser Glu Phe Tyr Asn Asn Val Leu Gly Arg Pro Gln
        130                 135                 140

Lys Lys Arg Ile Ile Val Arg Tyr Asp Gly Tyr His Gly Ser Thr Ala
145                 150                 155                 160

Leu Thr Ala Ala Cys Thr Gly Arg Thr Gly Asn Trp Pro Asn Phe Asp
                165                 170                 175

Ile Ala Gln Asp Arg Ile Ser Phe Leu Ser Ser Pro Asn Pro Arg His
                180                 185                 190

Ala Gly Asn Arg Ser Gln Glu Ala Phe Leu Asp Leu Val Gln Glu
            195                 200                 205

Phe Glu Asp Arg Ile Glu Ser Leu Gly Pro Asp Thr Ile Ala Ala Phe
        210                 215                 220

Leu Ala Glu Pro Ile Leu Ala Ser Gly Gly Val Ile Ile Pro Pro Ala
225                 230                 235                 240

Gly Tyr His Ala Arg Phe Lys Ala Ile Cys Glu Lys His Asp Ile Leu
                245                 250                 255

Tyr Ile Ser Asp Glu Val Val Thr Gly Phe Gly Arg Cys Gly Glu Trp
```

```
                    260                 265                 270
        Phe Ala Ser Glu Lys Val Phe Gly Val Val Pro Asp Ile Ile Thr Phe
                275                 280                 285

Ala Lys Gly Val Thr Ser Gly Tyr Val Pro Leu Gly Gly Leu Ala Ile
                290                 295                 300

Ser Glu Ala Val Leu Ala Arg Ile Ser Gly Glu Asn Ala Lys Gly Ser
        305                 310                 315                 320

Trp Phe Thr Asn Gly Tyr Thr Tyr Ser Asn Gln Pro Val Ala Cys Ala
                        325                 330                 335

Ala Ala Leu Ala Asn Ile Glu Leu Met Glu Arg Glu Gly Ile Val Asp
                        340                 345                 350

Gln Ala Arg Glu Met Ala Asp Tyr Phe Ala Ala Leu Ala Ser Leu
                        355                 360                 365

Arg Asp Leu Pro Gly Val Ala Glu Thr Arg Ser Val Gly Leu Val Gly
                        370                 375                 380

Cys Val Gln Cys Leu Leu Asp Pro Thr Arg Ala Asp Gly Thr Ala Glu
        385                 390                 395                 400

Asp Lys Ala Phe Thr Leu Lys Ile Asp Glu Arg Cys Phe Glu Leu Gly
                        405                 410                 415

Leu Ile Val Arg Pro Leu Gly Asp Leu Cys Val Ile Ser Pro Pro Leu
                        420                 425                 430

Ile Ile Ser Arg Ala Gln Ile Asp Glu Met Val Ala Ile Met Arg Gln
                        435                 440                 445

Ala Ile Thr Glu Val Ser Ala Ala His Gly Leu Thr Ala Lys Glu Pro
                        450                 455                 460

Ala Ala Val
        465

<210> SEQ ID NO 11
<211> LENGTH: 459
<212> TYPE: PRT
<213> ORGANISM: Escherichia coli

<400> SEQUENCE: 11

Met Asn Arg Leu Pro Ser Ser Ala Ser Ala Leu Ala Cys Ser Ala His
        1               5                   10                  15

Ala Leu Asn Leu Ile Glu Lys Arg Thr Leu Asp His Glu Glu Met Lys
                        20                  25                  30

Ala Leu Asn Arg Glu Val Ile Glu Tyr Phe Lys Glu His Val Asn Pro
                35                  40                  45

Gly Phe Leu Glu Tyr Arg Lys Ser Val Thr Ala Gly Gly Asp Tyr Gly
                50                  55                  60

Ala Val Glu Trp Gln Ala Gly Ser Leu Asn Thr Leu Val Asp Thr Gln
        65                  70                  75                  80

Gly Gln Glu Phe Ile Asp Cys Leu Gly Gly Phe Gly Ile Phe Asn Val
                        85                  90                  95

Gly His Arg Asn Pro Val Val Ser Ala Val Gln Asn Gln Leu Ala
                        100                 105                 110

Lys Gln Pro Leu His Ser Gln Glu Leu Leu Asp Pro Leu Arg Ala Met
                        115                 120                 125

Leu Ala Lys Thr Leu Ala Ala Leu Thr Pro Gly Lys Leu Lys Tyr Ser
                130                 135                 140

Phe Phe Cys Asn Ser Gly Thr Glu Ser Val Glu Ala Ala Leu Lys Leu
        145                 150                 155                 160
```

```
Ala Lys Ala Tyr Gln Ser Pro Arg Gly Lys Phe Thr Phe Ile Ala Thr
                165                 170                 175

Ser Gly Ala Phe His Gly Lys Ser Leu Gly Ala Leu Ser Ala Thr Ala
            180                 185                 190

Lys Ser Thr Phe Arg Lys Pro Phe Met Pro Leu Leu Pro Gly Phe Arg
        195                 200                 205

His Val Pro Phe Gly Asn Ile Glu Ala Met Arg Thr Ala Leu Asn Glu
    210                 215                 220

Cys Lys Lys Thr Gly Asp Asp Val Ala Val Ile Leu Glu Pro Ile
225                 230                 235                 240

Gln Gly Glu Gly Gly Val Ile Leu Pro Pro Gly Tyr Leu Thr Ala
                245                 250                 255

Val Arg Lys Leu Cys Asp Glu Phe Gly Ala Leu Met Ile Leu Asp Glu
        260                 265                 270

Val Gln Thr Gly Met Gly Arg Thr Gly Lys Met Phe Ala Cys Glu His
            275                 280                 285

Glu Asn Val Gln Pro Asp Ile Leu Cys Leu Ala Lys Ala Leu Gly Gly
    290                 295                 300

Gly Val Met Pro Ile Gly Ala Thr Ile Ala Thr Glu Glu Val Phe Ser
305                 310                 315                 320

Val Leu Phe Asp Asn Pro Phe Leu His Thr Thr Phe Gly Gly Asn
                325                 330                 335

Pro Leu Ala Cys Ala Ala Ala Leu Ala Thr Ile Asn Val Leu Leu Glu
            340                 345                 350

Gln Asn Leu Pro Ala Gln Ala Glu Gln Lys Gly Asp Met Leu Leu Asp
        355                 360                 365

Gly Phe Arg Gln Leu Ala Arg Glu Tyr Pro Asp Leu Val Gln Glu Ala
    370                 375                 380

Arg Gly Lys Gly Met Leu Met Ala Ile Glu Phe Val Asp Asn Glu Ile
385                 390                 395                 400

Gly Tyr Asn Phe Ala Ser Glu Met Phe Arg Gln Arg Val Leu Val Ala
                405                 410                 415

Gly Thr Leu Asn Asn Ala Lys Thr Ile Arg Ile Glu Pro Pro Leu Thr
            420                 425                 430

Leu Thr Ile Glu Gln Cys Glu Leu Val Ile Lys Ala Ala Arg Lys Ala
        435                 440                 445

Leu Ala Ala Met Arg Val Ser Val Glu Glu Ala
    450                 455
```

<210> SEQ ID NO 12
<211> LENGTH: 453
<212> TYPE: PRT
<213> ORGANISM: Vibrio fluvialis

<400> SEQUENCE: 12

```
Met Asn Lys Pro Gln Ser Trp Glu Ala Arg Ala Glu Thr Tyr Ser Leu
1               5                   10                  15

Tyr Gly Phe Thr Asp Met Pro Ser Leu His Gln Arg Gly Thr Val Val
                20                  25                  30

Val Thr His Gly Glu Gly Pro Tyr Ile Val Asp Val Asn Gly Arg Arg
            35                  40                  45

Tyr Leu Asp Ala Asn Ser Gly Leu Trp Asn Met Val Ala Gly Phe Asp
        50                  55                  60

His Lys Gly Leu Ile Asp Ala Ala Lys Ala Gln Tyr Glu Arg Phe Pro
65                  70                  75                  80
```

-continued

```
Gly Tyr His Ala Phe Phe Gly Arg Met Ser Asp Gln Thr Val Met Leu
                 85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Val His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Arg Glu Gly Ala Asp Thr Ile Ala Gly Phe Phe Ala Glu Pro
210                 215                 220

Val Met Gly Ala Gly Gly Val Ile Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Met Gly Ala Val Ile Leu Gly Pro Glu Leu Ser
290                 295                 300

Lys Arg Leu Glu Thr Ala Ile Glu Ala Ile Glu Glu Phe Pro His Gly
305                 310                 315                 320

Phe Thr Ala Ser Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
370                 375                 380

Lys Asp Lys Ala Ser Lys Thr Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450
```

<210> SEQ ID NO 13
<211> LENGTH: 224
<212> TYPE: PRT
<213> ORGANISM: Bacillus subtilis

```
<400> SEQUENCE: 13

Met Lys Ile Tyr Gly Ile Tyr Met Asp Arg Pro Leu Ser Gln Glu Glu
  1               5                  10                  15

Asn Glu Arg Phe Met Ser Phe Ile Ser Pro Glu Lys Arg Glu Lys Cys
             20                  25                  30

Arg Arg Phe Tyr His Lys Glu Asp Ala His Arg Thr Leu Leu Gly Asp
         35                  40                  45

Val Leu Val Arg Ser Val Ile Ser Arg Gln Tyr Gln Leu Asp Lys Ser
 50                  55                  60

Asp Ile Arg Phe Ser Thr Gln Glu Tyr Gly Lys Pro Cys Ile Pro Asp
 65                  70                  75                  80

Leu Pro Asp Ala His Phe Asn Ile Ser His Ser Gly Arg Trp Val Ile
                 85                  90                  95

Cys Ala Phe Asp Ser Gln Pro Ile Gly Ile Asp Ile Glu Lys Thr Lys
             100                 105                 110

Pro Ile Ser Leu Glu Ile Ala Lys Arg Phe Phe Ser Lys Thr Glu Tyr
         115                 120                 125

Ser Asp Leu Leu Ala Lys Asp Lys Asp Glu Gln Thr Asp Tyr Phe Tyr
130                 135                 140

His Leu Trp Ser Met Lys Glu Ser Phe Ile Lys Gln Glu Gly Lys Gly
145                 150                 155                 160

Leu Ser Leu Pro Leu Asp Ser Phe Ser Val Arg Leu His Gln Asp Gly
                165                 170                 175

Gln Val Ser Ile Glu Leu Pro Asp Ser His Ser Pro Cys Tyr Ile Lys
            180                 185                 190

Thr Tyr Glu Val Asp Pro Gly Tyr Lys Met Ala Val Cys Ala Ala His
        195                 200                 205

Pro Asp Phe Pro Glu Asp Ile Thr Met Val Ser Tyr Glu Glu Leu Leu
210                 215                 220

<210> SEQ ID NO 14
<211> LENGTH: 222
<212> TYPE: PRT
<213> ORGANISM: Nocardia sp. NRRL 5646

<400> SEQUENCE: 14

Met Ile Glu Thr Ile Leu Pro Ala Gly Val Glu Ser Ala Glu Leu Leu
  1               5                  10                  15

Glu Tyr Pro Glu Asp Leu Lys Ala His Pro Ala Glu Glu His Leu Ile
             20                  25                  30

Ala Lys Ser Val Glu Lys Arg Arg Asp Phe Ile Gly Ala Arg His
         35                  40                  45

Cys Ala Arg Leu Ala Leu Ala Glu Leu Gly Pro Pro Val Ala Ile
 50                  55                  60

Gly Lys Gly Glu Arg Gly Ala Pro Ile Trp Pro Arg Gly Val Val Gly
 65                  70                  75                  80

Ser Leu Thr His Cys Asp Gly Tyr Arg Ala Ala Val Ala His Lys
                 85                  90                  95

Met Arg Phe Arg Ser Ile Gly Ile Asp Ala Glu Pro His Ala Thr Leu
             100                 105                 110

Pro Glu Gly Val Leu Asp Ser Val Ser Leu Pro Pro Glu Arg Glu Trp
         115                 120                 125

Leu Lys Thr Thr Asp Ser Ala Leu His Leu Asp Arg Leu Leu Phe Cys
130                 135                 140
```

```
Ala Lys Glu Ala Thr Tyr Lys Ala Trp Trp Pro Leu Thr Ala Arg Trp
145                 150                 155                 160

Leu Gly Phe Glu Glu Ala His Ile Thr Phe Glu Ile Glu Asp Gly Ser
            165                 170                 175

Ala Asp Ser Gly Asn Gly Thr Phe His Ser Glu Leu Leu Val Pro Gly
        180                 185                 190

Gln Thr Asn Asp Gly Gly Thr Pro Leu Leu Ser Phe Asp Gly Arg Trp
        195                 200                 205

Leu Ile Ala Asp Gly Phe Ile Leu Thr Ala Ile Ala Tyr Ala
        210                 215                 220

<210> SEQ ID NO 15
<211> LENGTH: 272
<212> TYPE: PRT
<213> ORGANISM: Pseudomonas fluorescens

<400> SEQUENCE: 15

Met Ser Thr Phe Val Ala Lys Asp Gly Thr Gln Ile Tyr Phe Lys Asp
1               5                   10                  15

Trp Gly Ser Gly Lys Pro Val Leu Phe Ser His Gly Trp Leu Leu Asp
            20                  25                  30

Ala Asp Met Trp Glu Tyr Gln Met Glu Tyr Leu Ser Ser Arg Gly Tyr
        35                  40                  45

Arg Thr Ile Ala Phe Asp Arg Arg Gly Phe Gly Arg Ser Asp Gln Pro
    50                  55                  60

Trp Thr Gly Asn Asp Tyr Asp Thr Phe Ala Asp Asp Ile Ala Gln Leu
65                  70                  75                  80

Ile Glu His Leu Asp Leu Lys Glu Val Thr Leu Val Gly Phe Ser Met
                85                  90                  95

Gly Gly Gly Asp Val Ala Arg Tyr Ile Ala Arg His Gly Ser Ala Arg
            100                 105                 110

Val Ala Gly Leu Val Leu Leu Gly Ala Val Thr Pro Leu Phe Gly Gln
        115                 120                 125

Lys Pro Asp Tyr Pro Gln Gly Val Pro Leu Asp Val Phe Ala Arg Phe
    130                 135                 140

Lys Thr Glu Leu Leu Lys Asp Arg Ala Gln Phe Ile Ser Asp Phe Asn
145                 150                 155                 160

Ala Pro Phe Tyr Gly Ile Asn Lys Gly Gln Val Val Ser Gln Gly Val
                165                 170                 175

Gln Thr Gln Thr Leu Gln Ile Ala Leu Leu Ala Ser Leu Lys Ala Thr
            180                 185                 190

Val Asp Cys Val Thr Ala Phe Ala Glu Thr Asp Phe Arg Pro Asp Met
        195                 200                 205

Ala Lys Ile Asp Val Pro Thr Leu Val Ile His Gly Asp Gly Asp Gln
    210                 215                 220

Ile Val Pro Phe Glu Thr Thr Gly Lys Val Ala Ala Glu Leu Ile Lys
225                 230                 235                 240

Gly Ala Glu Leu Lys Val Tyr Lys Asp Ala Pro His Gly Phe Ala Val
                245                 250                 255

Thr His Ala Gln Gln Leu Asn Glu Asp Leu Leu Ala Phe Leu Lys Arg
            260                 265                 270

<210> SEQ ID NO 16
<211> LENGTH: 401
<212> TYPE: PRT
<213> ORGANISM: Escherichia coli
```

<400> SEQUENCE: 16

Met Arg Glu Ala Phe Ile Cys Asp Gly Ile Arg Thr Pro Ile Gly Arg
1               5                   10                  15

Tyr Gly Gly Ala Leu Ser Ser Val Arg Ala Asp Asp Leu Ala Ala Ile
            20                  25                  30

Pro Leu Arg Glu Leu Leu Val Arg Asn Pro Arg Leu Asp Ala Glu Cys
        35                  40                  45

Ile Asp Asp Val Ile Leu Gly Cys Ala Asn Gln Ala Gly Glu Asp Asn
50                  55                  60

Arg Asn Val Ala Arg Met Ala Thr Leu Leu Ala Gly Leu Pro Gln Ser
65                  70                  75                  80

Val Ser Gly Thr Thr Ile Asn Arg Leu Cys Gly Ser Gly Leu Asp Ala
                85                  90                  95

Leu Gly Phe Ala Ala Arg Ala Ile Lys Ala Gly Asp Gly Asp Leu Leu
            100                 105                 110

Ile Ala Gly Gly Val Glu Ser Met Ser Arg Ala Pro Phe Val Met Gly
            115                 120                 125

Lys Ala Ala Ser Ala Phe Ser Arg Gln Ala Glu Met Phe Asp Thr Thr
130                 135                 140

Ile Gly Trp Arg Phe Val Asn Pro Leu Met Ala Gln Gln Phe Gly Thr
145                 150                 155                 160

Asp Ser Met Pro Glu Thr Ala Glu Asn Val Ala Glu Leu Leu Lys Ile
                165                 170                 175

Ser Arg Glu Asp Gln Asp Ser Phe Ala Leu Arg Ser Gln Gln Arg Thr
            180                 185                 190

Ala Lys Ala Gln Ser Ser Gly Ile Leu Ala Glu Glu Ile Val Pro Val
            195                 200                 205

Val Leu Lys Asn Lys Lys Gly Val Val Thr Glu Ile Gln His Asp Glu
210                 215                 220

His Leu Arg Pro Glu Thr Thr Leu Glu Gln Leu Arg Gly Leu Lys Ala
225                 230                 235                 240

Pro Phe Arg Ala Asn Gly Val Ile Thr Ala Gly Asn Ala Ser Gly Val
                245                 250                 255

Asn Asp Gly Ala Ala Ala Leu Ile Ile Ala Ser Glu Gln Met Ala Ala
            260                 265                 270

Ala Gln Gly Leu Thr Pro Arg Ala Arg Ile Val Ala Met Ala Thr Ala
            275                 280                 285

Gly Val Glu Pro Arg Leu Met Gly Leu Gly Pro Val Pro Ala Thr Arg
290                 295                 300

Arg Val Leu Glu Arg Ala Gly Leu Ser Ile His Asp Met Asp Val Ile
305                 310                 315                 320

Glu Leu Asn Glu Ala Phe Ala Ala Gln Ala Leu Gly Val Leu Arg Glu
                325                 330                 335

Leu Gly Leu Pro Asp Asp Ala Pro His Val Asn Pro Asn Gly Gly Ala
            340                 345                 350

Ile Ala Leu Gly His Pro Leu Gly Met Ser Gly Ala Arg Leu Ala Leu
            355                 360                 365

Ala Ala Ser His Glu Leu His Arg Arg Asn Gly Arg Tyr Ala Leu Cys
370                 375                 380

Thr Met Cys Ile Gly Val Gly Gln Gly Ile Ala Met Ile Leu Glu Arg
385                 390                 395                 400

Val

<210> SEQ ID NO 17
<211> LENGTH: 451
<212> TYPE: PRT
<213> ORGANISM: Saccharomyces cerevisiae

<400> SEQUENCE: 17

```
Met Ser Glu Val Ser Lys Trp Pro Ala Ile Asn Pro Phe His Trp Gly
1               5                   10                  15

Tyr Asn Gly Thr Val Ser His Ile Val Gly Glu Asn Gly Ser Ile Lys
            20                  25                  30

Leu His Leu Lys Asp Asn Lys Glu Gln Val Asp Phe Asp Glu Phe Ala
        35                  40                  45

Asn Lys Tyr Val Pro Thr Leu Lys Asn Gly Ala Gln Phe Lys Leu Ser
    50                  55                  60

Pro Tyr Leu Phe Thr Gly Ile Leu Gln Thr Leu Tyr Leu Gly Ala Ala
65                  70                  75                  80

Asp Phe Ser Lys Lys Phe Pro Val Phe Tyr Gly Arg Glu Ile Val Lys
                85                  90                  95

Phe Ser Asp Gly Gly Val Cys Thr Ala Asp Trp Leu Ile Asp Ser Trp
            100                 105                 110

Lys Lys Asp Tyr Glu Phe Asp Gln Ser Thr Thr Ser Phe Asp Lys Lys
        115                 120                 125

Lys Phe Asp Lys Asp Glu Lys Ala Thr His Pro Glu Gly Trp Pro Arg
    130                 135                 140

Leu Gln Pro Arg Thr Arg Tyr Leu Lys Asp Asn Glu Leu Glu Glu Leu
145                 150                 155                 160

Arg Glu Val Asp Leu Pro Leu Val Val Ile Leu His Gly Leu Ala Gly
                165                 170                 175

Gly Ser His Glu Pro Ile Ile Arg Ser Leu Ala Glu Asn Leu Ser Arg
            180                 185                 190

Ser Gly Arg Phe Gln Val Val Leu Asn Thr Arg Gly Cys Ala Arg
        195                 200                 205

Ser Lys Ile Thr Thr Arg Asn Leu Phe Thr Ala Tyr His Thr Met Asp
    210                 215                 220

Ile Arg Glu Phe Leu Gln Arg Glu Lys Gln Arg His Pro Asp Arg Lys
225                 230                 235                 240

Leu Tyr Ala Val Gly Cys Ser Phe Gly Ala Thr Met Leu Ala Asn Tyr
                245                 250                 255

Leu Gly Glu Glu Gly Asp Lys Ser Pro Leu Ser Ala Ala Ala Thr Leu
            260                 265                 270

Cys Asn Pro Trp Asp Leu Leu Leu Ser Ala Ile Arg Met Ser Gln Asp
        275                 280                 285

Trp Trp Ser Arg Thr Leu Phe Ser Lys Asn Ile Ala Gln Phe Leu Thr
    290                 295                 300

Arg Thr Val Gln Val Asn Met Gly Glu Leu Gly Val Pro Asn Gly Ser
305                 310                 315                 320

Leu Pro Asp His Pro Thr Val Lys Asn Pro Ser Phe Tyr Met Phe
                325                 330                 335

Thr Pro Glu Asn Leu Ile Lys Ala Lys Ser Phe Lys Ser Thr Arg Glu
            340                 345                 350

Phe Asp Glu Val Tyr Thr Ala Pro Ala Leu Gly Phe Pro Asn Ala Met
        355                 360                 365

Glu Tyr Tyr Lys Ala Ala Ser Ser Ile Asn Arg Val Asp Thr Ile Arg
```

Val Pro Thr Leu Val Ile Asn Ser Arg Asp Asp Pro Val Val Gly Pro
385                 390                 395                 400

Asp Gln Pro Tyr Ser Ile Val Glu Lys Asn Pro Arg Ile Leu Tyr Cys
            405                 410                 415

Arg Thr Asp Leu Gly Gly His Leu Ala Tyr Leu Asp Lys Asp Asn Asn
            420                 425                 430

Ser Trp Ala Thr Lys Ala Ile Ala Glu Phe Phe Thr Lys Phe Asp Glu
        435                 440                 445

Leu Val Val
        450

<210> SEQ ID NO 18
<211> LENGTH: 256
<212> TYPE: PRT
<213> ORGANISM: Escherichia coli

<400> SEQUENCE: 18

Met Asn Asn Ile Trp Trp Gln Thr Lys Gly Gln Gly Asn Val His Leu
1               5                   10                  15

Val Leu Leu His Gly Trp Gly Leu Asn Ala Glu Val Trp Arg Cys Ile
            20                  25                  30

Asp Glu Glu Leu Ser Ser His Phe Thr Leu His Leu Val Asp Leu Pro
        35                  40                  45

Gly Phe Gly Arg Ser Arg Gly Phe Gly Ala Leu Ser Leu Ala Asp Met
    50                  55                  60

Ala Glu Ala Val Leu Gln Gln Ala Pro Asp Lys Ala Ile Trp Leu Gly
65                  70                  75                  80

Trp Ser Leu Gly Gly Leu Val Ala Ser Gln Ile Ala Leu Thr His Pro
                85                  90                  95

Glu Arg Val Gln Ala Leu Val Thr Val Ala Ser Ser Pro Cys Phe Ser
            100                 105                 110

Ala Arg Asp Glu Trp Pro Gly Ile Lys Pro Asp Val Leu Ala Gly Phe
        115                 120                 125

Gln Gln Gln Leu Ser Asp Asp Phe Gln Arg Thr Val Glu Arg Phe Leu
    130                 135                 140

Ala Leu Gln Thr Met Gly Thr Glu Thr Ala Arg Gln Asp Ala Arg Ala
145                 150                 155                 160

Leu Lys Lys Thr Val Leu Ala Leu Pro Met Pro Glu Val Asp Val Leu
                165                 170                 175

Asn Gly Gly Leu Glu Ile Leu Lys Thr Val Asp Leu Arg Gln Pro Leu
            180                 185                 190

Gln Asn Val Ser Met Pro Phe Leu Arg Leu Tyr Gly Tyr Leu Asp Gly
        195                 200                 205

Leu Val Pro Arg Lys Val Val Pro Met Leu Asp Lys Leu Trp Pro His
    210                 215                 220

Ser Glu Ser Tyr Ile Phe Ala Lys Ala Ala His Ala Pro Phe Ile Ser
225                 230                 235                 240

His Pro Ala Glu Phe Cys His Leu Leu Val Ala Leu Lys Gln Arg Val
                245                 250                 255

<210> SEQ ID NO 19
<211> LENGTH: 438
<212> TYPE: PRT
<213> ORGANISM: Clostridium a

```
<400> SEQUENCE: 19

Met Asp Trp Lys Lys Ile Tyr Glu Asp Arg Thr Cys Thr Ala Asp Glu
  1               5                  10                  15

Ala Val Lys Ser Ile Lys Ser Gly Asp Arg Val Leu Phe Ala His Cys
             20                  25                  30

Val Ala Glu Pro Pro Val Leu Val Glu Ala Met Val Ala Asn Ala Ala
         35                  40                  45

Ala Tyr Lys Asn Val Thr Val Ser His Met Val Thr Leu Gly Lys Gly
     50                  55                  60

Glu Tyr Ser Lys Pro Glu Tyr Lys Glu Asn Phe Thr Phe Glu Gly Trp
 65                  70                  75                  80

Phe Thr Ser Pro Ser Thr Arg Gly Ser Ile Ala Glu Gly His Gly Gln
                 85                  90                  95

Phe Val Pro Val Phe Phe His Glu Val Pro Ser Leu Ile Arg Lys Asp
            100                 105                 110

Ile Phe His Val Asp Val Phe Met Val Met Val Ser Pro Pro Asp His
        115                 120                 125

Asn Gly Phe Cys Cys Val Gly Val Ser Ser Asp Tyr Thr Met Gln Ala
    130                 135                 140

Ile Lys Ser Ala Lys Ile Val Leu Ala Glu Val Asn Asp Gln Val Pro
145                 150                 155                 160

Val Val Tyr Gly Asp Thr Phe Val His Val Ser Glu Ile Asp Lys Phe
                165                 170                 175

Val Glu Thr Ser His Pro Leu Pro Glu Ile Gly Leu Pro Lys Ile Gly
            180                 185                 190

Glu Val Glu Ala Ala Ile Gly Lys His Cys Ala Ser Leu Ile Glu Asp
        195                 200                 205

Gly Ser Thr Leu Gln Leu Gly Ile Gly Ala Ile Pro Asp Ala Val Leu
    210                 215                 220

Ser Gln Leu Lys Asp Lys Lys His Leu Gly Ile His Ser Glu Met Ile
225                 230                 235                 240

Ser Asp Gly Val Val Asp Leu Tyr Glu Ala Gly Val Ile Asp Cys Ser
                245                 250                 255

Gln Lys Ser Ile Asp Lys Gly Lys Met Ala Ile Thr Phe Leu Met Gly
            260                 265                 270

Thr Lys Arg Leu Tyr Asp Phe Ala Ala Asn Asn Pro Lys Val Glu Leu
        275                 280                 285

Lys Pro Val Asp Tyr Ile Asn His Pro Ser Val Val Ala Gln Cys Ser
    290                 295                 300

Lys Met Val Cys Ile Asn Ala Cys Leu Gln Val Asp Phe Met Gly Gln
305                 310                 315                 320

Ile Val Ser Asp Ser Ile Gly Thr Lys Gln Phe Ser Gly Val Gly Gly
                325                 330                 335

Gln Val Asp Phe Val Arg Gly Ala Ser Met Ser Ile Asp Gly Lys Gly
            340                 345                 350

Lys Ala Ile Ile Ala Met Pro Ser Val Ala Lys Lys Asp Gly Ser
    355                 360                 365

Met Ile Ser Lys Ile Val Pro Phe Ile Asp His Gly Ala Ala Val Thr
370                 375                 380

Thr Ser Arg Asn Asp Ala Asp Tyr Val Val Thr Glu Tyr Gly Ile Ala
        385                 390                 395                 400

Glu Met Lys Gly Lys Ser Leu Gln Asp Arg Ala Arg Ala Leu Ile Asn
            405                 410                 415
```

```
Ile Ala His Pro Asp Phe Lys Asp Glu Leu Lys Ala Glu Phe Glu Lys
            420                 425                 430

Arg Phe Asn Ala Ala Phe
            435

<210> SEQ ID NO 20
<211> LENGTH: 550
<212> TYPE: PRT
<213> ORGANISM: Salmonella typhimurium

<400> SEQUENCE: 20

Met Gln Asn Pro Tyr Thr Val Ala Asp Tyr Leu Leu Asp Arg Leu Ala
 1               5                  10                  15

Gly Cys Gly Ile Gly His Leu Phe Gly Val Pro Gly Asp Tyr Asn Leu
             20                  25                  30

Gln Phe Leu Asp His Val Ile Asp His Pro Thr Leu Arg Trp Val Gly
         35                  40                  45

Cys Ala Asn Glu Leu Asn Ala Ala Tyr Ala Ala Asp Gly Tyr Ala Arg
     50                  55                  60

Met Ser Gly Ala Gly Ala Leu Leu Thr Thr Phe Gly Val Gly Glu Leu
 65                  70                  75                  80

Ser Ala Ile Asn Gly Ile Ala Gly Ser Tyr Ala Glu Tyr Val Pro Val
                 85                  90                  95

Leu His Ile Val Gly Ala Pro Cys Ser Ala Ala Gln Arg Gly Glu
            100                 105                 110

Leu Met His His Thr Leu Gly Asp Gly Asp Phe Arg His Phe Tyr Arg
            115                 120                 125

Met Ser Gln Ala Ile Ser Ala Ala Ser Ala Ile Leu Asp Glu Gln Asn
130                 135                 140

Ala Cys Phe Glu Ile Asp Arg Val Leu Gly Glu Met Leu Ala Ala Arg
145                 150                 155                 160

Arg Pro Gly Tyr Ile Met Leu Pro Ala Asp Val Ala Lys Lys Thr Ala
                165                 170                 175

Ile Pro Pro Thr Gln Ala Leu Ala Leu Pro Val His Glu Ala Gln Ser
            180                 185                 190

Gly Val Glu Thr Ala Phe Arg Tyr His Ala Arg Gln Cys Leu Met Asn
        195                 200                 205

Ser Arg Arg Ile Ala Leu Leu Ala Asp Phe Leu Ala Gly Arg Phe Gly
    210                 215                 220

Leu Arg Pro Leu Leu Gln Arg Trp Met Ala Glu Thr Pro Ile Ala His
225                 230                 235                 240

Ala Thr Leu Leu Met Gly Lys Gly Leu Phe Asp Glu Gln His Pro Asn
                245                 250                 255

Phe Val Gly Thr Tyr Ser Ala Gly Ala Ser Ser Lys Glu Val Arg Gln
            260                 265                 270

Ala Ile Glu Asp Ala Asp Arg Val Ile Cys Val Gly Thr Arg Phe Val
        275                 280                 285

Asp Thr Leu Thr Ala Gly Phe Thr Gln Gln Leu Pro Ala Glu Arg Thr
    290                 295                 300

Leu Glu Ile Gln Pro Tyr Ala Ser Arg Ile Gly Glu Thr Trp Phe Asn
305                 310                 315                 320

Leu Pro Met Ala Gln Ala Val Ser Thr Leu Arg Glu Leu Cys Leu Glu
                325                 330                 335

Cys Ala Phe Ala Pro Pro Pro Thr Arg Ser Ala Gly Gln Pro Val Arg
```

```
            340                 345                 350
Ile Asp Lys Gly Glu Leu Thr Gln Glu Ser Phe Trp Gln Thr Leu Gln
            355                 360                 365

Gln Tyr Leu Lys Pro Gly Asp Ile Ile Leu Val Asp Gln Gly Thr Ala
            370                 375                 380

Ala Phe Gly Ala Ala Ala Leu Ser Leu Pro Asp Gly Ala Glu Val Val
385                 390                 395                 400

Leu Gln Pro Leu Trp Gly Ser Ile Gly Tyr Ser Leu Pro Ala Ala Phe
                405                 410                 415

Gly Ala Gln Thr Ala Cys Pro Asp Arg Arg Val Ile Leu Ile Ile Gly
                420                 425                 430

Asp Gly Ala Ala Gln Leu Thr Ile Gln Glu Met Gly Ser Met Leu Arg
                435                 440                 445

Asp Gly Gln Ala Pro Val Ile Leu Leu Leu Asn Asn Asp Gly Tyr Thr
                450                 455                 460

Val Glu Arg Ala Ile His Gly Ala Ala Gln Arg Tyr Asn Asp Ile Ala
465                 470                 475                 480

Ser Trp Asn Trp Thr Gln Ile Pro Pro Ala Leu Asn Ala Ala Gln Gln
                485                 490                 495

Ala Glu Cys Trp Arg Val Thr Gln Ala Ile Gln Leu Ala Glu Val Leu
                500                 505                 510

Glu Arg Leu Ala Arg Pro Gln Arg Leu Ser Phe Ile Glu Val Met Leu
                515                 520                 525

Pro Lys Ala Asp Leu Pro Glu Leu Leu Arg Thr Val Thr Arg Ala Leu
                530                 535                 540

Glu Ala Arg Asn Gly Gly
545                 550

<210> SEQ ID NO 21
<211> LENGTH: 1227
<212> TYPE: PRT
<213> ORGANISM: Mycobacterium smegmatis

<400> SEQUENCE: 21

Met Ser Ser Ser Pro Ser Pro Phe Gly Gln Asn Glu Trp Leu Val Glu
1               5                   10                  15

Glu Met Tyr Arg Lys Phe Arg Asp Asp Pro Ser Ser Val Asp Pro Ser
                20                  25                  30

Trp His Glu Phe Leu Val Asp Tyr Ser Pro Glu Pro Thr Thr Asp Ser
                35                  40                  45

Ala Ser Asn Gly Arg Thr Thr Thr Ala Ala Pro Val Thr Pro Pro Thr
50                  55                  60

Pro Ala Pro Ala Pro Ala Pro Glu Pro Lys Ala Pro Lys Pro Ala
65                  70                  75                  80

Ala Lys Thr Glu Ala Lys Pro Ala Lys Pro Ala Lys Ser Ala Thr Pro
                85                  90                  95

Ala Lys Gly Asp Glu Ser Gln Ile Leu Arg Gly Ala Ala Ala Ala Val
                100                 105                 110

Val Lys Asn Met Asn Ala Ser Leu Glu Val Pro Thr Ala Thr Ser Val
                115                 120                 125

Arg Ala Ile Pro Ala Lys Leu Met Ile Asp Asn Arg Val Val Ile Asn
                130                 135                 140

Asn His Leu Lys Arg Thr Arg Gly Gly Lys Ile Ser Phe Thr His Leu
145                 150                 155                 160
```

```
Leu Gly Tyr Ala Ile Val Gln Ala Val Lys Phe Pro Asn Met Asn
                165                 170                 175

Arg His Phe Ala Val Val Asp Gly Lys Pro Thr Ala Ile Thr Pro Ala
                180                 185                 190

His Thr Asn Leu Gly Leu Ala Ile Asp Leu Gln Gly Lys Asp Gly Asn
                195                 200                 205

Arg Ser Leu Val Val Ala Ala Ile Lys Arg Cys Glu Thr Met Arg Phe
            210                 215                 220

Gly Gln Phe Ile Ala Ala Tyr Glu Asp Ile Val Arg Arg Ala Arg Asp
225                 230                 235                 240

Gly Lys Leu Thr Ala Glu Asp Phe Ser Gly Val Thr Ile Ser Leu Thr
                245                 250                 255

Asn Pro Gly Thr Leu Gly Thr Val His Ser Val Pro Arg Leu Met Gln
                260                 265                 270

Gly Gln Gly Ala Ile Ile Gly Ala Gly Ala Met Glu Tyr Pro Ala Glu
                275                 280                 285

Phe Gln Gly Ala Ser Glu Glu Arg Ile Ala Asp Leu Gly Ile Gly Lys
                290                 295                 300

Leu Ile Thr Leu Thr Ser Thr Tyr Asp His Arg Ile Ile Gln Gly Ala
305                 310                 315                 320

Glu Ser Gly Asp Phe Leu Arg Thr Ile His Gln Leu Leu Asp Asp
                325                 330                 335

Asp Phe Phe Asp Glu Ile Phe Arg Glu Leu Gly Ile Pro Tyr Glu Pro
                340                 345                 350

Val Arg Trp Arg Thr Asp Asn Pro Asp Ser Ile Glu Asp Lys Asn Ala
                355                 360                 365

Arg Val Ile Glu Leu Ile Ala Ala Tyr Arg Asn Arg Gly His Leu Met
            370                 375                 380

Ala Asp Ile Asp Pro Leu Arg Leu Asp Asn Thr Arg Phe Arg Ser His
385                 390                 395                 400

Pro Asp Leu Asp Val Asn Ser His Gly Leu Thr Leu Trp Asp Leu Asp
                405                 410                 415

Arg Glu Phe Lys Val Asp Gly Phe Ala Gly Val Gln Arg Lys Lys Leu
                420                 425                 430

Arg Asp Ile Leu Ser Val Leu Arg Asp Ala Tyr Cys Arg His Val Gly
            435                 440                 445

Val Glu Tyr Thr His Ile Leu Glu Pro Glu Gln Gln Arg Trp Ile Gln
                450                 455                 460

Glu Arg Val Glu Thr Lys His Asp Lys Pro Thr Val Ala Glu Gln Lys
465                 470                 475                 480

Tyr Ile Leu Ser Lys Leu Asn Ala Ala Glu Ala Phe Glu Thr Phe Leu
                485                 490                 495

Gln Thr Lys Tyr Val Gly Gln Lys Arg Phe Ser Leu Glu Gly Ala Glu
                500                 505                 510

Thr Val Ile Pro Met Met Asp Ala Val Ile Asp Gln Cys Ala Glu His
                515                 520                 525

Gly Leu Asp Glu Val Val Ile Ala Met Pro His Arg Gly Arg Leu Asn
            530                 535                 540

Val Leu Ala Asn Ile Val Gly Lys Pro Tyr Ser Gln Ile Phe Ser Glu
545                 550                 555                 560

Phe Glu Gly Asn Leu Asn Pro Ser Gln Ala His Gly Ser Gly Asp Val
                565                 570                 575

Lys Tyr His Leu Gly Ala Thr Gly Thr Tyr Ile Gln Met Phe Gly Asp
```

```
            580             585             590
Asn Asp Ile Glu Val Ser Leu Thr Ala Asn Pro Ser His Leu Glu Ala
        595             600             605
Val Asp Pro Val Leu Glu Gly Leu Val Arg Ala Lys Gln Asp Leu Leu
    610             615             620
Asp Thr Gly Glu Glu Gly Ser Asp Asn Arg Phe Ser Val Val Pro Leu
625             630             635             640
Met Leu His Gly Asp Ala Ala Phe Ala Gly Gln Gly Val Val Ala Glu
            645             650             655
Thr Leu Asn Leu Ala Leu Leu Arg Gly Tyr Arg Thr Gly Gly Thr Ile
        660             665             670
His Ile Val Val Asn Asn Gln Ile Gly Phe Thr Thr Ala Pro Thr Asp
    675             680             685
Ser Arg Ser Ser Glu Tyr Cys Thr Asp Val Ala Lys Met Ile Gly Ala
    690             695             700
Pro Ile Phe His Val Asn Gly Asp Asp Pro Glu Ala Cys Ala Trp Val
705             710             715             720
Ala Arg Leu Ala Val Asp Phe Arg Gln Ala Phe Lys Lys Asp Val Val
            725             730             735
Ile Asp Met Leu Cys Tyr Arg Arg Gly His Asn Glu Gly Asp Asp
            740             745             750
Pro Ser Met Thr Gln Pro Tyr Met Tyr Asp Val Ile Asp Thr Lys Arg
        755             760             765
Gly Ser Arg Lys Ala Tyr Thr Glu Ala Leu Ile Gly Arg Gly Asp Ile
    770             775             780
Ser Met Lys Glu Ala Glu Asp Ala Leu Arg Asp Tyr Gln Gly Gln Leu
785             790             795             800
Glu Arg Val Phe Asn Glu Val Arg Glu Leu Glu Lys His Glu Ile Glu
            805             810             815
Pro Ser Glu Ser Val Glu Ala Asp Gln Gln Ile Pro Ser Lys Leu Ala
        820             825             830
Thr Ala Val Asp Lys Ala Met Leu Gln Arg Ile Gly Asp Ala His Leu
    835             840             845
Ala Leu Pro Glu Gly Phe Thr Val His Pro Arg Val Arg Pro Val Leu
    850             855             860
Glu Lys Arg Arg Glu Met Ala Tyr Glu Gly Arg Ile Asp Trp Ala Phe
865             870             875             880
Ala Glu Leu Leu Ala Leu Gly Ser Leu Ile Ala Glu Gly Lys Leu Val
            885             890             895
Arg Leu Ser Gly Gln Asp Thr Gln Arg Gly Thr Phe Thr Gln Arg His
        900             905             910
Ala Val Ile Val Asp Arg Lys Thr Gly Glu Glu Phe Thr Pro Leu Gln
    915             920             925
Leu Leu Ala Thr Asn Pro Asp Gly Thr Pro Thr Gly Gly Lys Phe Leu
    930             935             940
Val Tyr Asn Ser Ala Leu Ser Glu Phe Ala Ala Val Gly Phe Glu Tyr
945             950             955             960
Gly Tyr Ser Val Gly Asn Pro Asp Ala Met Val Leu Trp Glu Ala Gln
            965             970             975
Phe Gly Asp Phe Val Asn Gly Ala Gln Ser Ile Ile Asp Glu Phe Ile
            980             985             990
Ser Ser Gly Glu Ala Lys Trp Gly Gln Leu Ser Asp Val Val Leu Leu
        995             1000            1005
```

```
Leu Pro His Gly His Glu Gly Gln Gly Pro Asp His Thr Ser Gly Arg
    1010                1015                1020

Ile Glu Arg Phe Leu Gln Leu Trp Ala Glu Gly Ser Met Thr Ile Ala
1025                1030                1035                1040

Met Pro Ser Thr Pro Ala Asn Tyr Phe His Leu Leu Arg Arg His Gly
                1045                1050                1055

Lys Asp Gly Ile Gln Arg Pro Leu Ile Val Phe Thr Pro Lys Ser Met
            1060                1065                1070

Leu Arg Asn Lys Ala Ala Val Ser Asp Ile Arg Asp Phe Thr Glu Ser
        1075                1080                1085

Lys Phe Arg Ser Val Leu Glu Glu Pro Met Tyr Thr Asp Gly Glu Gly
    1090                1095                1100

Asp Arg Asn Lys Val Thr Arg Leu Leu Leu Thr Ser Gly Lys Ile Tyr
1105                1110                1115                1120

Tyr Glu Leu Ala Ala Arg Lys Ala Lys Glu Asn Arg Glu Asp Val Ala
                1125                1130                1135

Ile Val Arg Ile Glu Gln Leu Ala Pro Leu Pro Arg Arg Arg Leu Ala
            1140                1145                1150

Glu Thr Leu Asp Arg Tyr Pro Asn Val Lys Glu Lys Phe Trp Val Gln
        1155                1160                1165

Glu Glu Pro Ala Asn Gln Gly Ala Trp Pro Ser Phe Gly Leu Thr Leu
    1170                1175                1180

Pro Glu Ile Leu Pro Asp His Phe Thr Gly Leu Lys Arg Ile Ser Arg
1185                1190                1195                1200

Arg Ala Met Ser Ala Pro Ser Ser Gly Ser Ser Lys Val His Ala Val
                1205                1210                1215

Glu Gln Gln Glu Ile Leu Asp Thr Ala Phe Gly
        1220                1225

<210> SEQ ID NO 22
<211> LENGTH: 548
<212> TYPE: PRT
<213> ORGANISM: Lactococcus lactis subsp. lactis

<400> SEQUENCE: 22

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
                20                  25                  30

Asp Gln Ile Ile Ser Arg Lys Asp Met Lys Trp Val Gly Asn Ala Asn
            35                  40                  45

Glu Leu Asn Ala Ser Tyr Met Ala Asp Gly Tyr Ala Arg Thr Lys Lys
        50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
                100                 105                 110

His Thr Leu Ala Asp Gly Asp Phe Lys His Phe Met Lys Met His Glu
            115                 120                 125

Pro Val Thr Ala Ala Arg Thr Leu Leu Thr Ala Glu Asn Ala Thr Val
        130                 135                 140

Glu Ile Asp Arg Val Leu Ser Ala Leu Leu Lys Glu Arg Lys Pro Val
```

```
            145                 150                 155                 160
        Tyr Ile Asn Leu Pro Val Asp Val Ala Ala Lys Ala Glu Lys Pro
                            165                 170                 175

Ser Leu Pro Leu Lys Lys Glu Asn Pro Thr Ser Asn Thr Ser Asp Gln
                        180                 185                 190

Glu Ile Leu Asn Lys Ile Gln Glu Ser Leu Lys Asn Ala Lys Lys Pro
                    195                 200                 205

Ile Val Ile Thr Gly His Glu Ile Ile Ser Phe Gly Leu Glu Asn Thr
            210                 215                 220

Val Thr Gln Phe Ile Ser Lys Thr Lys Leu Pro Ile Thr Thr Leu Asn
        225                 230                 235                 240

Phe Gly Lys Ser Ser Val Asp Glu Thr Leu Pro Ser Phe Leu Gly Ile
                            245                 250                 255

Tyr Asn Gly Lys Leu Ser Glu Pro Asn Leu Lys Glu Phe Val Glu Ser
                        260                 265                 270

Ala Asp Phe Ile Leu Met Leu Gly Val Lys Leu Thr Asp Ser Ser Thr
                    275                 280                 285

Gly Ala Phe Thr His His Leu Asn Glu Asn Lys Met Ile Ser Leu Asn
            290                 295                 300

Ile Asp Glu Gly Lys Ile Phe Asn Glu Ser Ile Gln Asn Phe Asp Phe
        305                 310                 315                 320

Glu Ser Leu Ile Ser Ser Leu Leu Asp Leu Ser Gly Ile Glu Tyr Lys
                            325                 330                 335

Gly Lys Tyr Ile Asp Lys Lys Gln Glu Asp Phe Val Pro Ser Asn Ala
                        340                 345                 350

Leu Leu Ser Gln Asp Arg Leu Trp Gln Ala Val Glu Asn Leu Thr Gln
                    355                 360                 365

Ser Asn Glu Thr Ile Val Ala Glu Gln Gly Thr Ser Phe Phe Gly Ala
            370                 375                 380

Ser Ser Ile Phe Leu Lys Pro Lys Ser His Phe Ile Gly Gln Pro Leu
        385                 390                 395                 400

Trp Gly Ser Ile Gly Tyr Thr Phe Pro Ala Ala Leu Gly Ser Gln Ile
                            405                 410                 415

Ala Asp Lys Glu Ser Arg His Leu Leu Phe Ile Gly Asp Gly Ser Leu
                        420                 425                 430

Gln Leu Thr Val Gln Glu Leu Gly Leu Ala Ile Arg Glu Lys Ile Asn
                    435                 440                 445

Pro Ile Cys Phe Ile Ile Asn Asn Asp Gly Tyr Thr Val Glu Arg Glu
            450                 455                 460

Ile His Gly Pro Asn Gln Ser Tyr Asn Asp Ile Pro Met Trp Asn Tyr
        465                 470                 475                 480

Ser Lys Leu Pro Glu Ser Phe Gly Ala Thr Glu Glu Arg Val Val Ser
                            485                 490                 495

Lys Ile Val Arg Thr Glu Asn Glu Phe Val Ser Val Met Lys Glu Ala
                        500                 505                 510

Gln Ala Asp Pro Asn Arg Met Tyr Trp Ile Glu Leu Val Leu Ala Lys
                    515                 520                 525

Glu Asp Ala Pro Lys Val Leu Lys Lys Met Gly Lys Leu Phe Ala Glu
            530                 535                 540

Gln Asn Lys Ser
        545

<210> SEQ ID NO 23
```

<211> LENGTH: 397
<212> TYPE: PRT
<213> ORGANISM: Treponema denticola

<400> SEQUENCE: 23

```
Met Ile Val Lys Pro Met Val Arg Asn Asn Ile Cys Leu Asn Ala His
  1               5                  10                  15

Pro Gln Gly Cys Lys Lys Gly Val Glu Asp Gln Ile Glu Tyr Thr Lys
             20                  25                  30

Lys Arg Ile Thr Ala Glu Val Lys Ala Gly Ala Lys Ala Pro Lys Asn
         35                  40                  45

Val Leu Val Leu Gly Cys Ser Asn Gly Tyr Gly Leu Ala Ser Arg Ile
 50                  55                  60

Thr Ala Ala Phe Gly Tyr Gly Ala Ala Thr Ile Gly Val Ser Phe Glu
 65                  70                  75                  80

Lys Ala Gly Ser Glu Thr Lys Tyr Gly Thr Pro Gly Trp Tyr Asn Asn
                 85                  90                  95

Leu Ala Phe Asp Glu Ala Ala Lys Arg Glu Gly Leu Tyr Ser Val Thr
            100                 105                 110

Ile Asp Gly Asp Ala Phe Ser Asp Glu Ile Lys Ala Gln Val Ile Glu
        115                 120                 125

Glu Ala Lys Lys Lys Gly Ile Lys Phe Asp Leu Ile Val Tyr Ser Leu
130                 135                 140

Ala Ser Pro Val Arg Thr Asp Pro Asp Thr Gly Ile Met His Lys Ser
145                 150                 155                 160

Val Leu Lys Pro Phe Gly Lys Thr Phe Thr Gly Lys Thr Val Asp Pro
                165                 170                 175

Phe Thr Gly Glu Leu Lys Glu Ile Ser Ala Glu Pro Ala Asn Asp Glu
            180                 185                 190

Glu Ala Ala Ala Thr Val Lys Val Met Gly Gly Glu Asp Trp Glu Arg
        195                 200                 205

Trp Ile Lys Gln Leu Ser Lys Glu Gly Leu Leu Glu Glu Gly Cys Ile
210                 215                 220

Thr Leu Ala Tyr Ser Tyr Ile Gly Pro Glu Ala Thr Gln Ala Leu Tyr
225                 230                 235                 240

Arg Lys Gly Thr Ile Gly Lys Ala Lys Glu His Leu Glu Ala Thr Ala
                245                 250                 255

His Arg Leu Asn Lys Glu Asn Pro Ser Ile Arg Ala Phe Val Ser Val
            260                 265                 270

Asn Lys Gly Leu Val Thr Arg Ala Ser Ala Val Ile Pro Val Ile Pro
        275                 280                 285

Leu Tyr Leu Ala Ser Leu Phe Lys Val Met Lys Glu Lys Gly Asn His
290                 295                 300

Glu Gly Cys Ile Glu Gln Ile Thr Arg Leu Tyr Ala Glu Arg Leu Tyr
305                 310                 315                 320

Arg Lys Asp Gly Thr Ile Pro Val Asp Glu Asn Arg Ile Arg Ile
                325                 330                 335

Asp Asp Trp Glu Leu Glu Glu Asp Val Gln Lys Ala Val Ser Ala Leu
            340                 345                 350

Met Glu Lys Val Thr Gly Glu Asn Ala Glu Ser Leu Thr Asp Leu Ala
        355                 360                 365

Gly Tyr Arg His Asp Phe Leu Ala Ser Asn Gly Phe Asp Val Glu Gly
370                 375                 380

Ile Asn Tyr Glu Ala Glu Val Glu Arg Phe Asp Arg Ile
```

385             390             395

<210> SEQ ID NO 24
<211> LENGTH: 539
<212> TYPE: PRT
<213> ORGANISM: Euglena gracilis

<400> SEQUENCE: 24

Met Ser Cys Pro Ala Ser Pro Ser Ala Ala Val Val Ser Ala Gly Ala
1               5                   10                  15

Leu Cys Leu Cys Val Ala Thr Val Leu Leu Ala Thr Gly Ser Asn Pro
            20                  25                  30

Thr Ala Leu Ser Thr Ala Ser Thr Arg Ser Pro Thr Ser Leu Val Arg
        35                  40                  45

Gly Val Asp Arg Gly Leu Met Arg Pro Thr Ala Ala Ala Leu Thr
    50                  55                  60

Thr Met Arg Glu Val Pro Gln Met Ala Glu Gly Phe Ser Gly Glu Ala
65                  70                  75                  80

Thr Ser Ala Trp Ala Ala Gly Pro Gln Trp Ala Ala Pro Leu Val
                85                  90                  95

Ala Ala Ala Ser Ser Ala Leu Ala Leu Trp Trp Trp Ala Arg Arg
            100                 105                 110

Ser Val Arg Arg Pro Leu Ala Ala Leu Ala Glu Leu Pro Thr Ala Val
        115                 120                 125

Thr His Leu Ala Pro Pro Met Ala Met Phe Thr Thr Thr Ala Lys Val
    130                 135                 140

Ile Gln Pro Lys Ile Arg Gly Phe Ile Cys Thr Thr Thr His Pro Ile
145                 150                 155                 160

Gly Cys Glu Lys Arg Val Gln Glu Glu Ile Ala Tyr Ala Arg Ala His
                165                 170                 175

Pro Pro Thr Ser Pro Gly Pro Lys Arg Val Leu Val Ile Gly Cys Ser
            180                 185                 190

Thr Gly Tyr Gly Leu Ser Thr Arg Ile Thr Ala Ala Phe Gly Tyr Gln
        195                 200                 205

Ala Ala Thr Leu Gly Val Phe Leu Ala Gly Pro Pro Thr Lys Gly Arg
    210                 215                 220

Pro Ala Ala Ala Gly Trp Tyr Asn Thr Val Ala Phe Glu Lys Ala Ala
225                 230                 235                 240

Leu Glu Ala Gly Leu Tyr Ala Arg Ser Leu Asn Gly Asp Ala Phe Asp
                245                 250                 255

Ser Thr Thr Lys Ala Arg Thr Val Glu Ala Ile Lys Arg Asp Leu Gly
            260                 265                 270

Thr Val Asp Leu Val Val Tyr Ser Ile Ala Ala Pro Lys Arg Thr Asp
        275                 280                 285

Pro Ala Thr Gly Val Leu His Lys Ala Cys Leu Lys Pro Ile Gly Ala
    290                 295                 300

Thr Tyr Thr Asn Arg Thr Val Asn Thr Asp Lys Ala Glu Val Thr Asp
305                 310                 315                 320

Val Ser Ile Glu Pro Ala Ser Pro Glu Glu Ile Ala Asp Thr Val Lys
                325                 330                 335

Val Met Gly Gly Glu Asp Trp Glu Leu Trp Ile Gln Ala Leu Ser Glu
            340                 345                 350

Ala Gly Val Leu Ala Glu Gly Ala Lys Thr Val Ala Tyr Ser Tyr Ile
        355                 360                 365

Gly Pro Glu Met Thr Trp Pro Val Tyr Trp Ser Gly Thr Ile Gly Glu
370                 375                 380

Ala Lys Lys Asp Val Glu Lys Ala Ala Lys Arg Ile Thr Gln Gln Tyr
385                 390                 395                 400

Gly Cys Pro Ala Tyr Pro Val Val Ala Lys Ala Leu Val Thr Gln Ala
                405                 410                 415

Ser Ser Ala Ile Pro Val Val Pro Leu Tyr Ile Cys Leu Leu Tyr Arg
                420                 425                 430

Val Met Lys Glu Lys Gly Thr His Glu Gly Cys Ile Glu Gln Met Val
            435                 440                 445

Arg Leu Leu Thr Thr Lys Leu Tyr Pro Glu Asn Gly Ala Pro Ile Val
450                 455                 460

Asp Glu Ala Gly Arg Val Arg Val Asp Asp Trp Glu Met Ala Glu Asp
465                 470                 475                 480

Val Gln Gln Ala Val Lys Asp Leu Trp Ser Gln Val Ser Thr Ala Asn
                485                 490                 495

Leu Lys Asp Ile Ser Asp Phe Ala Gly Tyr Gln Thr Glu Phe Leu Arg
                500                 505                 510

Leu Phe Gly Phe Gly Ile Asp Gly Val Asp Tyr Asp Gln Pro Val Asp
            515                 520                 525

Val Glu Ala Asp Leu Pro Ser Ala Ala Gln Gln
530                 535

<210> SEQ ID NO 25
<211> LENGTH: 404
<212> TYPE: PRT
<213> ORGANISM: Sphaerochaeta pleomorpha

<400> SEQUENCE: 25

Met Ile Ile Thr Lys Lys Val Leu Arg Asn Val Ser Leu Thr Ala His
1               5                   10                  15

Pro Gln Gly Cys Ala Gln Tyr Val Gln Asp Gln Ile Asp Trp Val Gln
                20                  25                  30

Ala His Ala His Ala Ser Leu Asp Ser Arg Tyr Gln Lys Cys Asp Asp
            35                  40                  45

Leu Lys Leu Pro Arg Arg Ile Leu Val Leu Gly Gly Ser Thr Gly Tyr
50                  55                  60

Gly Leu Ser Ser Arg Ile Val Gly Ala Phe Gly Ser Gly Ser Asp Thr
65                  70                  75                  80

Ile Asn Val Ser Phe Glu Arg Glu Pro Ser Gln Thr Lys Thr Ala Thr
                85                  90                  95

Pro Gly Trp Tyr Asn Thr Met Ala Phe Glu Lys Arg Ala Lys Glu Ala
                100                 105                 110

Gly Leu Lys Ala Glu Ser Ile Phe Gly Asp Ala Phe Ser Asp Glu Thr
            115                 120                 125

Lys Gln Lys Thr Gly Ala Leu Ile Lys Ser Leu Phe Gly Gln Val Asp
130                 135                 140

Leu Val Ile Tyr Ser Leu Ala Ser Pro Leu Arg Thr Asp Pro Lys Thr
145                 150                 155                 160

Gly Thr Thr Tyr Arg Ser Val Leu Lys Pro Leu Gly Lys Pro Phe Ser
                165                 170                 175

Ala Leu Ser Val Asp Met Asp Cys Asp Val Val Lys Met Ala Thr Ile
                180                 185                 190

Glu Pro Ala Glu Gly Thr Gln Ala Glu Glu Thr Val His Val Met Gly
            195                 200                 205

Gly Glu Asp Trp Ala Leu Trp Ile Glu Tyr Leu Met Gln Glu Asn Leu
210                 215                 220

Leu Ala Glu Gly Ala Met Thr Val Ser Tyr Ser Tyr Ile Gly Pro Lys
225                 230                 235                 240

Ile Thr Tyr Pro Val Tyr Arg Glu Gly Thr Ile Gly Lys Ala Lys Glu
                245                 250                 255

Asp Leu Glu Lys Thr Ala Ala Glu Leu Thr Lys Lys Leu Gln Gln Ile
            260                 265                 270

Gln Gly Lys Ala Tyr Val Ser Val Asn Lys Ala Leu Val Thr Arg Ala
        275                 280                 285

Ser Ala Val Ile Pro Val Pro Leu Tyr Met Ala Ile Leu Tyr Gln
290                 295                 300

Val Met Lys Glu Arg Asp Leu His Glu His Cys Thr Glu Gln Ile Tyr
305                 310                 315                 320

Arg Leu Phe Thr Glu Lys Leu Phe Ser Gly Lys Gln Ile Pro Thr Asp
                325                 330                 335

Asp Glu Gly Arg Val Arg Val Asp Asp Trp Glu Met Gln Asp Asp Ile
            340                 345                 350

Gln Ala Glu Val Glu Arg Arg Trp Ala Leu Gln Lys Gly Gly Glu Pro
        355                 360                 365

Leu Lys Asp Ala Asp Ile Glu Gly Val Arg Lys Glu Tyr Asp Gln Ile
370                 375                 380

His Gly Phe Gly Phe Asp Ser Ile Asp Tyr Glu Lys Asp Val Asp Pro
385                 390                 395                 400

Arg Asp Ile Tyr

<210> SEQ ID NO 26
<211> LENGTH: 397
<212> TYPE: PRT
<213> ORGANISM: Burkholderia mallei

<400> SEQUENCE: 26

Met Ile Ile Lys Pro Arg Val Arg Gly Phe Ile Cys Val Thr Thr His
1               5                   10                  15

Pro Ala Gly Cys Ala Ala Ser Val Arg Glu Gln Ile Ala Tyr Val Ala
            20                  25                  30

Arg Arg Gly Pro Ile Glu Arg Gly Pro Lys Lys Val Leu Val Ile Gly
        35                  40                  45

Ala Ser Thr Gly Tyr Gly Leu Ala Ala Arg Ile Ala Ala Ala Phe Gly
    50                  55                  60

Val Gly Ala Ala Thr Leu Gly Val Phe Phe Glu Arg Ala Pro Ala Asp
65                  70                  75                  80

Ala Lys Pro Gly Thr Ala Gly Trp Tyr Asn Ser Ala Ala Phe His Asp
                85                  90                  95

Glu Ala Ala Ala Arg Gly Leu Gln Ala Thr Ser Val Asn Gly Asp Ala
            100                 105                 110

Phe Ser Asp Glu Ile Lys His Lys Thr Ile Asp Ala Ile Arg Arg Asp
        115                 120                 125

Leu Gly Gln Val Asp Leu Val Val Tyr Ser Val Ala Ala Pro Arg Arg
    130                 135                 140

Thr His Pro Lys Thr Gly Val Thr His Gln Ser Thr Leu Lys Pro Ile
145                 150                 155                 160

Gly His Ala Val Arg Leu Arg Gly Ile Asp Thr Asp Asn Glu Ala Ile
                165                 170                 175

Lys Glu Thr Leu Leu Gln Pro Ala Thr Pro Asp Glu Ile Ala Asp Thr
180 185 190

Val Ala Val Met Gly Gly Glu Asp Trp Arg Met Trp Ile Asp Ala Leu
195 200 205

Asp Ala Ala Gly Val Leu Ala Asp Gly Ala Lys Thr Thr Ala Phe Thr
210 215 220

Tyr Leu Gly Glu Gln Val Thr His Asp Ile Tyr Trp Asn Gly Ser Ile
225 230 235 240

Gly Glu Ala Lys Lys Asp Leu Asp Arg Thr Val Leu Ala Leu Arg Gly
245 250 255

Lys Leu Ala Ala Arg Gly Gly Asp Ala Arg Val Ser Val Leu Lys Ala
260 265 270

Val Val Thr Gln Ala Ser Ser Ala Ile Pro Met Met Pro Leu Tyr Leu
275 280 285

Ser Leu Leu Phe Lys Val Met Lys Ala Arg Gly Thr His Glu Gly Cys
290 295 300

Ile Glu Gln Val Asp Gly Leu Leu Arg Asp Ser Leu Tyr Ser Ala Gln
305 310 315 320

Pro His Val Asp Ala Glu Gly Arg Leu Arg Ala Asp Arg Leu Glu Leu
325 330 335

Asp Pro Ala Val Gln Ala Arg Val Leu Glu Leu Trp Asp Gln Val Thr
340 345 350

Asp Asp Asn Leu Tyr Thr Leu Thr Asp Phe Ala Gly Tyr Lys Ala Glu
355 360 365

Phe Leu Arg Leu Phe Gly Phe Gly Ile Asp Gly Val Asp Tyr Asp Ala
370 375 380

Pro Val Glu Pro Asn Val Arg Ile Pro Asn Leu Ile Glu
385 390 395

<210> SEQ ID NO 27
<211> LENGTH: 402
<212> TYPE: PRT
<213> ORGANISM: Xanthomonas oryzae pv. oryzae

<400> SEQUENCE: 27

Met Ile Ile His Pro Lys Val Arg Gly Phe Ile Cys Thr Thr Thr His
1 5 10 15

Pro Leu Gly Cys Glu Arg Asn Val Leu Glu Gln Ile Ala Ala Thr Arg
20 25 30

Ala Arg Gly Val Arg Asn Asp Gly Pro Lys Lys Val Leu Val Ile Gly
35 40 45

Ala Ser Ser Gly Tyr Gly Leu Ala Ser Arg Ile Thr Ala Ala Phe Gly
50 55 60

Phe Gly Ala Asp Thr Leu Gly Val Phe Phe Glu Lys Pro Gly Thr Ala
65 70 75 80

Ser Lys Ala Gly Thr Ala Gly Trp Tyr Asn Ser Ala Ala Phe Asp Lys
85 90 95

His Ala Lys Ala Ala Gly Leu Tyr Ser Lys Ser Ile Asn Gly Asp Ala
100 105 110

Phe Ser Asp Ala Ala Arg Ala Gln Val Ile Glu Leu Ile Lys Thr Glu
115 120 125

Met Gly Gly Gln Val Asp Leu Val Val Tyr Ser Leu Ala Ser Pro Val
130 135 140

Arg Lys Leu Pro Gly Ser Gly Glu Val Lys Arg Ser Ala Leu Lys Pro

```
            145                 150                 155                 160
Ile Gly Gln Thr Tyr Thr Ala Thr Ala Ile Asp Thr Asn Lys Asp Thr
                    165                 170                 175

Ile Ile Gln Ala Ser Ile Glu Pro Ala Ser Ala Gln Glu Ile Glu Glu
                180                 185                 190

Thr Ile Thr Val Met Gly Gly Gln Asp Trp Glu Leu Trp Ile Asp Ala
            195                 200                 205

Leu Glu Gly Ala Gly Val Leu Ala Asp Gly Ala Arg Ser Val Ala Phe
        210                 215                 220

Ser Tyr Ile Gly Thr Glu Ile Thr Trp Pro Ile Tyr Trp His Gly Ala
225                 230                 235                 240

Leu Gly Lys Ala Lys Val Asp Leu Asp Arg Thr Ala Gln Arg Leu Asn
                245                 250                 255

Ala Arg Leu Ala Lys His Gly Gly Ala Asn Val Ala Val Leu Lys
                260                 265                 270

Ser Val Val Thr Gln Ala Ser Ala Ala Ile Pro Val Met Pro Leu Tyr
                275                 280                 285

Ile Ser Met Val Tyr Lys Ile Met Lys Glu Lys Gly Leu His Glu Gly
            290                 295                 300

Thr Ile Glu Gln Leu Asp Arg Leu Phe Arg Glu Arg Leu Tyr Arg Gln
305                 310                 315                 320

Asp Gly Gln Pro Ala Glu Val Asp Glu Gln Asn Arg Leu Arg Leu Asp
                325                 330                 335

Asp Trp Glu Leu Arg Asp Asp Val Gln Asp Ala Cys Lys Ala Leu Trp
            340                 345                 350

Pro Gln Val Thr Thr Glu Asn Leu Phe Glu Leu Thr Asp Tyr Ala Gly
                355                 360                 365

Tyr Lys His Glu Phe Leu Lys Leu Phe Gly Phe Arg Thr Asp Val
            370                 375                 380

Asp Tyr Asp Ala Asp Val Ala Thr Asp Val Ala Phe Asp Cys Ile Glu
385                 390                 395                 400

Leu Ala

<210> SEQ ID NO 28
<211> LENGTH: 396
<212> TYPE: PRT
<213> ORGANISM: Flavobacterium johnsoniae

<400> SEQUENCE: 28

Met Ile Ile Glu Pro Arg Met Arg Gly Phe Ile Cys Leu Thr Ala His
1               5                   10                  15

Pro Ala Gly Cys Glu Gln Asn Val Lys Asn Gln Ile Glu Tyr Ile Lys
            20                  25                  30

Ser Lys Gly Ala Ile Ala Gly Ala Lys Lys Val Leu Val Ile Gly Ala
        35                  40                  45

Ser Thr Gly Phe Gly Leu Ala Ser Arg Ile Thr Ser Ala Phe Gly Ser
    50                  55                  60

Asp Ala Ala Thr Ile Gly Val Phe Phe Glu Lys Pro Val Glu Gly
65                  70                  75                  80

Lys Thr Ala Ser Pro Gly Trp Tyr Asn Ser Ala Phe Glu Lys Glu
                85                  90                  95

Ala His Lys Ala Gly Leu Tyr Ala Lys Ser Ile Asn Gly Asp Ala Phe
            100                 105                 110

Ser Asn Glu Ile Lys Arg Glu Thr Leu Asp Leu Ile Lys Ala Asp Leu
```

```
                115                 120                 125
Gly Gln Val Asp Leu Val Ile Tyr Ser Leu Ala Ser Pro Val Arg Thr
    130                 135                 140

Asn Pro Asn Thr Gly Val Thr His Arg Ser Val Leu Lys Pro Ile Gly
145                 150                 155                 160

Gln Thr Phe Thr Asn Lys Thr Val Asp Phe His Thr Gly Asn Val Ser
                165                 170                 175

Glu Val Ser Ile Ala Pro Ala Asn Glu Glu Asp Ile Glu Asn Thr Val
                180                 185                 190

Ala Val Met Gly Gly Glu Asp Trp Ala Met Trp Ile Asp Ala Leu Lys
        195                 200                 205

Asn Glu Asn Leu Leu Ala Glu Gly Ala Thr Thr Ile Ala Tyr Ser Tyr
    210                 215                 220

Ile Gly Pro Glu Leu Thr Glu Ala Val Tyr Arg Lys Gly Thr Ile Gly
225                 230                 235                 240

Arg Ala Lys Asp His Leu Glu Ala Thr Ala Phe Thr Ile Thr Asp Thr
                245                 250                 255

Leu Lys Ser Leu Gly Gly Lys Ala Tyr Val Ser Val Asn Lys Ala Leu
                260                 265                 270

Val Thr Gln Ala Ser Ser Ala Ile Pro Val Ile Pro Leu Tyr Ile Ser
        275                 280                 285

Leu Leu Tyr Lys Ile Met Lys Glu Glu Gly Ile His Glu Gly Cys Ile
    290                 295                 300

Glu Gln Ile Gln Arg Leu Phe Gln Asp Arg Leu Tyr Asn Gly Ser Glu
305                 310                 315                 320

Val Pro Val Asp Glu Lys Gly Arg Ile Arg Ile Asp Asp Trp Glu Met
                325                 330                 335

Arg Glu Asp Val Gln Ala Lys Val Ala Ala Leu Trp Lys Glu Ala Thr
                340                 345                 350

Thr Glu Thr Leu Pro Ser Ile Gly Asp Leu Ala Gly Tyr Arg Asn Asp
        355                 360                 365

Phe Leu Asn Leu Phe Gly Phe Glu Phe Ala Gly Val Asp Tyr Lys Ala
    370                 375                 380

Asp Thr Asn Glu Val Val Asn Ile Glu Ser Ile Lys
385                 390                 395
```